United States Patent
Guerin et al.

(10) Patent No.: US 8,937,077 B2
(45) Date of Patent: Jan. 20, 2015

(54) BICYCLIC DIAMINES AS JANUS KINASE INHIBITORS

(75) Inventors: David Joseph Guerin, Natick, MA (US); Jason D. Brubaker, Cambridge, MA (US); Michelle Martinez, Medford, MA (US); Joon O. Jung, Newton, MA (US); Neville J. Anthony, Northborough, MA (US); Mark E. Scott, Andover, MA (US); Carolyn Michele Cammarano, Worcester, MA (US); Dawn Marie Mampreian Hoffman, Boston, MA (US); Hyun Chong Woo, Natick, MA (US); Christopher J. Dinsmore, Newton, MA (US); Philip Jones, Houston, TX (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 23 days.

(21) Appl. No.: 13/880,767

(22) PCT Filed: Oct. 17, 2011

(86) PCT No.: PCT/US2011/056498

§ 371 (c)(1),
(2), (4) Date: Apr. 22, 2013

(87) PCT Pub. No.: WO2012/054364

PCT Pub. Date: Apr. 26, 2012

(65) Prior Publication Data

US 2013/0225577 A1    Aug. 29, 2013

Related U.S. Application Data

(60) Provisional application No. 61/405,921, filed on Oct. 22, 2010.

(51) Int. Cl.
| | | |
|---|---|---|
| *A01N 43/90* | (2006.01) | |
| *A61K 31/519* | (2006.01) | |
| *C07D 487/00* | (2006.01) | |
| *C07D 471/04* | (2006.01) | |
| *C07D 519/00* | (2006.01) | |

(52) U.S. Cl.
CPC ............ *C07D 471/04* (2013.01); *A61K 31/519* (2013.01); *C07D 519/00* (2013.01)
USPC ........................................ 514/265.1; 544/280

(58) Field of Classification Search
None
See application file for complete search history.

(56) References Cited

U.S. PATENT DOCUMENTS 7,593,820 B2    9/2009    Wilks et al.

FOREIGN PATENT DOCUMENTS

| WO | 2006069080 A2 | 6/2006 |
| WO | 2009054941 A1 | 4/2009 |

OTHER PUBLICATIONS

WO2012054364—International Search Report.

*Primary Examiner* — Jeffrey H Murray
(74) *Attorney, Agent, or Firm* — Patricia A. Shatynski; Laura Ginkel

(57) ABSTRACT

The instant invention provides compounds of formula I which are Jak inhibitors, and as such are useful for the treatment of Jak-mediated diseases such as rheumatoid arthritis, asthma, COPD and cancer.

14 Claims, No Drawings

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: peptide substrate

<400> SEQUENCE: 1

Glu Gln Glu Asp Glu Pro Glu Gly Asp Tyr Phe Glu Trp Leu Trp
 1               5                  10                  15

BICYCLIC DIAMINES AS JANUS KINASE INHIBITORS

CROSS REFERENCE TO RELATED APPLICATIONS

This application is a U.S. National Phase application under 35 U.S.C. §371 of PCT Application No. PCT/US2011/056498, filed Oct. 17, 2011 which claims priority under 35 U.S.C. §119(e) from U.S. Provisional Application Ser. No. 61/405,921, filed Oct. 22, 2010.

BACKGROUND OF THE INVENTION

Studies of interferon (IFN)-induced receptor mediated gene expression led to the initial discovery of a Janus kinase (Jak) signaling pathway, which has been shown to be a common signaling pathway used by many cytokines and growth factors. The mammalian Jak family of intracellular tyrosine kinases, has four members; Jak1, Jak2, Jak3 and Tyk2. Jaks range in size from 120 to 140 kDa and contain seven conserved Jak homology (JH) domains which define this kinase super family.

Prototypically, the binding of a cytokine to its cell surface receptor results in receptor dimerization and subsequent activation/phosphorylation of Jak tyrosine kinases which are constitutively associated with the receptor. Specific tyrosine residues on the receptor are then phosphorylated by activated Jaks and serve as docking sites for a family of latent cytoplasmic transcription factors known as Signal Transducers and Activators of Transcription (STATS). STATS are phosphorylated by Jaks, dimerize, then translocate to the nucleus where they bind specific DNA elements and activate gene transcription.

Many pro-inflammatory cytokines (IL-6, IL-12, IL-15, IL-23, GM-CSF and IFN-γ) which are implicated in autoimmune diseases mediate their activity through the jak kinases. As a consequence, these enzymes have long been considered attractive drug targets. The essential role of Jaks in mediating the biological effects of cytokines has been confirmed by natural mutations in humans and targeted disruption in mice. Humans with a genetic loss of Jak3 have a severe combined immunodefiency (SCID) phenotype due to a developmental block in T and NK cell development and nonfunctional B-cells. Humans lacking Tyk2 are susceptible to microbial infection, have a Th2 bias with Hyper-IgE syndrome and defective cytokine signaling (IL-6, 10, 12 and 23). Signaling can be restored by transfection of the wild type kinase.

Animal KO models of the Jak family of kinases have demonstrated significant phenotypes. Jak1 KO animals exhibit defective responses to class 2 cytokines (IL-10 family), those utilizing the common gamma chain $\gamma_c$ (IL-2, IL-4 etc) and gp 130 receptor subunits (IL-6, LIF, OSM), resulting in perinatal lethality due to developmental, neurological and lymphoid defects. Jak2 KO mice exhibit defective erythropoiesis caused by a block in EPO signaling, resulting in embryonic lethality. Jak3 KO mice are viable but exhibit a SCID phenotype with nonfunctional T-cells and a lack of B and NK-cells (similar to human mutation). Tyk2 KO animals manifest modest viral susceptibility, reduced IL-12 responses, resistance to arthritis and enhanced Th2 cell-mediated allergic inflammation.

A considerable body of literature has accumulated that link the Jak/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of Jaks. The invention also provides a method for the treatment and prevention of Jak-mediated diseases and disorders using the novel compounds, as well as pharmaceutical compositions containing the compounds.

DETAILED DESCRIPTION OF THE INVENTION

The present invention provides compounds of formula I:

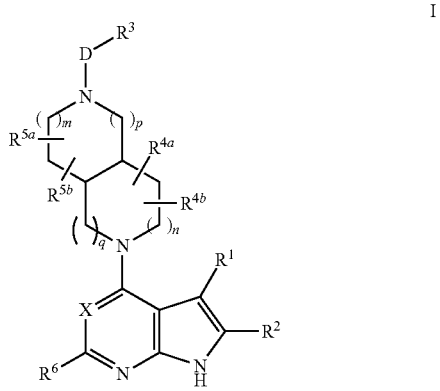

or a pharmaceutically acceptable salt thereof; wherein:

X is N or CH;

m and n are each independently 1, 2 or 3;

p and q are each independently 0 or 1;

D is a bond, —C(O)—, —C(O)NR$^b$—, —C(O)O— or —SO$_2$—;

R$^1$ and R$^2$ are independently H, halogen or C$_{1-3}$alkyl;

R$^3$ is selected from the group consisting of (1) hydrogen, (2) C$_{1-6}$alkyl, (3) C$_{2-10}$alkenyl, (4) C$_{2-10}$alkynyl, (5) -L-C$_{3-10}$cycloalkyl, (6) -L-aryl, (7) -L-heteroaryl, (8) -L-heterocyclyl, wherein alkyl, alkenyl and alkynyl are optionally substituted with 1 to 5 groups independently selected from R$^x$; cycloalkyl and heterocycly are optionally substituted with 1 to 5 groups independently selected from R$^y$; and aryl and heteroaryl are optionally substituted with 1 to 5 groups independently selected from R$^z$;

L is a bond, C$_{1-6}$alkylene, C$_{2-6}$alkenylene, C$_{2-6}$alkynylene, arylene, heteroarylene, C$_{3-10}$cycloalkylene or heterocyclyene; wherein alkylene, alkenylene and alkynylene are optionally substituted with 1 to 5 groups independently selected from R$^x$, aryl and heteroaryl (aryl and heteroaryl being optionally substituted with 1 to 3 groups independently selected from R$^z$); cycloalkylene or heterocyclyene are optionally substituted with 1 to 5 groups independently selected from R$^y$; and arylene and heteroarylene are optionally substituted with 1 to 5 groups independently selected from R$^z$;

R$^{4a}$, R$^{4b}$, R$^{5a}$ and R$^{5b}$ and are each independently selected from the group consisting of (1) hydrogen, (2) OR$^a$, (3) cyano, (4) halogen, (5) C$_{1-6}$alkyl, (6) C$_{2-10}$alkenyl, (7) C(O)R$^a$, (8) CO$_2$R$^a$, (9) NR$^b$R$^c$, and (10) CONR$^b$R$^c$, wherein alkyl, alkenyl and alkylcarbonyl are optionally substituted with 1 to 5 groups independently selected from $R^x$;

$R^6$ is H or $NHR^b$;

$R^a$ is selected from the group consisting of H, $C_{1-6}$alkyl, $C_{1-6}$haloalkyl, $C_{2-6}$hydroxyalkyl, $C_{2-6}(C_{1-3}$alkoxy)alkyl, $C_{2-6}$cyanoalkyl, $C_{2-6}$-aminoalkyl, $C_{2-6}$(monoC$_{1-3}$alkyl-amino)alkyl, $C_{2-6}$(diC$_{1-3}$alkylamino)alkyl, $C_{3-6}$cycloalkyl, aryl, heteroaryl and heterocyclyl;

$R^b$ and $R^c$ are each independently selected from H, $C_{1-6}$alkyl, $C_{1-6}$haloalkyl, $C_{3-6}$cycloalkyl, $C_{2-6}$cyanoalkyl, $C_{2-6}$hydroxyalkyl, $C_{2-6}$-aminoalkyl, —COR$^a$, aryl and heteroaryl; or $R^b$, $R^c$ and the nitrogen atom to which they are attached together form a 4- to 7-membered ring optionally having an additional heteroatom selected from NR$^d$, O and S(O)r, wherein said ring being optionally substituted with 1 to 4 groups independently selected from halogen, cyano and $C_{1-6}$cyanoalkyl;

r is 0, 1 or 2, $R^d$ is selected from the group consisting of (1) H, (2) $C_{1-6}$alkyl, (3) C(O)C$_{1-6}$alkyl, $R^x$ is selected from the group consisting of (1) oxo, (2) OR$^a$, (3) cyano, (4) halogen, (5) NR$^b$R$^c$, (6) CO$_2$R$^a$, (7) CONR$^b$R$^c$; (8) —COR$^a$, (9) —C$_{0-6}$alkylaryl, (10)—C$_{0-6}$ alkylheteroaryl, and (11) S(O)$_r$R$^a$;

$R^y$ is selected from the group consisting of (1) a member of R$^z$, and (2) oxo;

$R^z$ is selected from the group consisting of (1) OR$^a$, (2) cyano, (3) halogen, (4) COR$^a$, (5) CO$_2$R$^a$, (6) nitro, (7) NR$^b$R$^c$, and (8) CONR$^b$R$^c$; (9) $C_{1-6}$alkyl, (10) $C_{1-6}$haloalkyl, (11) $C_{1-6}$hydroxyalkyl, (12) $C_{1-6}$cyanoalkyl, (13) $C_{1-6}(C_{1-3}$alkoxy)alkyl, (14) $C_{1-6}$aminoalkyl, (15) $C_{1-6}$ mono($C_{1-3}$alkylamino)alkyl, (16) $C_{1-6}$di($C_{1-3}$alkylamino)alkyl, (17) $C_{2-6}$alkenyl, (18) $C_{2-6}$alkynyl, (19) —SO$_2$NR$^b$R$^c$, (20) —NR$^b$SO$_2$C$_{1-6}$alkyl, (21) —NR$^b$SO$_2$aryl (22)—C$_{0-6}$alkylNC(O)(OC$_{1-6}$ alkyl).

In one embodiment of compounds of formula I are compounds of formula Ia wherein the variables are as defined in formula I:

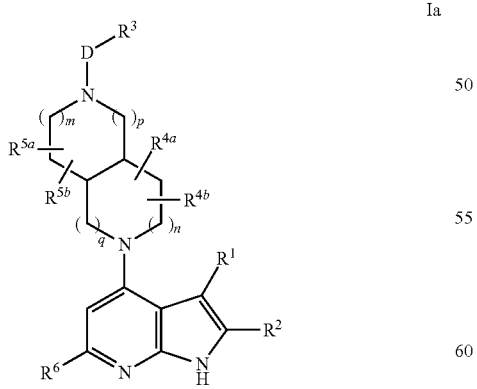

Ia and pharmaceutically acceptable salts thereof.

In another embodiment of compounds of formula I are compounds of formula Ib wherein the variables are as defined in formula I:

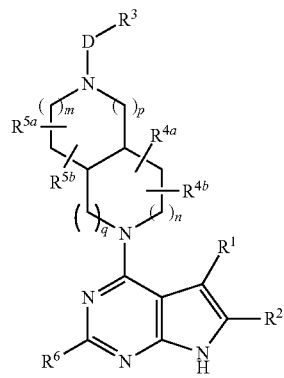

Ib and pharmaceutically acceptable salts thereof.

In another embodiment of compounds of formula I are compounds of formula Ic wherein the variables are as defined in formula I:

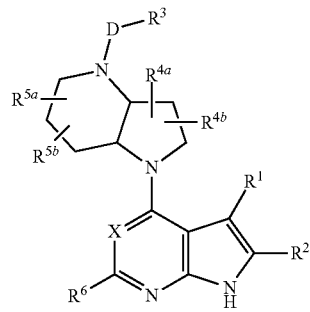

Ic and pharmaceutically acceptable salts thereof.

In another embodiment of compounds of formula I are compounds of formula Id wherein the variables are as defined in formula I:

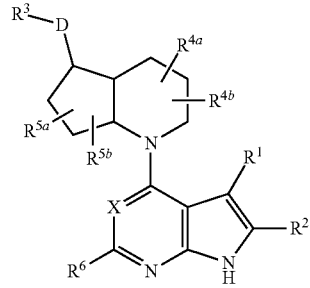

Id and pharmaceutically acceptable salts thereof.

In yet another embodiment of the present invention is a compound of formula Ig:

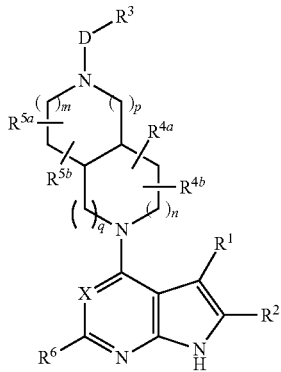

or a pharmaceutically acceptable salt thereof; wherein:
X is N or CH;
m and n are each independently 1, 2 or 3;
p and q are each independently 0 or 1;
D is a bond, —C(O)—, —C(O)NR$^b$—, —C(O)O— or —SO$_2$—;
R$^1$ and R$^2$ are independently H, halogen or C$_{1-3}$alkyl;
R$^3$ is selected from the group consisting of (1) hydrogen, (2) C$_{1-6}$alkyl, (3) C$_{2-10}$alkenyl, (4) C$_{2-10}$alkynyl, (5) -L-C$_{3-10}$cycloalkyl, (6)-L-aryl, (7)-L-heteroaryl, (8)-L-heterocyclyl, wherein alkyl, alkenyl and alkynyl are optionally substituted with 1 to 5 groups independently selected from R$^x$; cycloalkyl and heterocycly are optionally substituted with 1 to 5 groups independently selected from R$^y$; and aryl and heteroaryl are optionally substituted with 1 to 5 groups independently selected from R$^z$;
L is a bond, C$_{1-6}$alkylene, C$_{2-6}$alkenylene, C$_{2-6}$alkynylene, arylene, heteroarylene, C$_{3-10}$cycloalkylene or heterocyclyene; wherein alkylene, alkenylene and alkynylene are optionally substituted with 1 to 5 groups independently selected from R$^x$, aryl and heteroaryl (aryl and heteroaryl being optionally substituted with 1 to 3 groups independently selected from R$^z$); cycloalkylene or heterocyclyene are optionally substituted with 1 to 5 groups independently selected from R$^y$; and arylene and heteroarylene are optionally substituted with 1 to 5 groups independently selected from R$^z$;
R$^{4a}$, R$^{4b}$, R$^{5a}$ and R$^{5b}$ and are each independently selected from the group consisting of (1) hydrogen, (2) OR$^a$, (3) cyano, (4) halogen, (5) C$_{1-6}$alkyl, (6) C$_{2-10}$alkenyl, (7) C(O)R$^a$, (8) CO$_2$R$^a$, (9) NR$^b$R$^c$, and (10) CONR$^b$R$^c$, wherein alkyl, alkenyl and alkylcarbonyl are optionally substituted with 1 to 5 groups independently selected from R$^x$;
R$^6$ is H or NHR$^b$;
R$^a$ is selected from the group consisting of H, C$_{1-6}$alkyl, C$_{1-6}$haloalkyl, C$_{2-6}$hydroxyalkyl, C$_{2-6}$(C$_{1-3}$alkoxy)alkyl, C$_{2-6}$cyanoalkyl, C$_{2-6}$-aminoalkyl, C$_{2-6}$(monoC$_{1-3}$alkyl-amino)alkyl, C$_{2-6}$(diC$_{1-3}$alkylamino)alkyl, C$_{3-6}$cycloalkyl, aryl, heteroaryl and heterocyclyl;
R$^b$ and R$^c$ are each independently selected from H, C$_{1-6}$alkyl, C$_{1-6}$haloalkyl, C$_{3-6}$cycloalkyl, C$_{2-6}$cyanoalkyl, C$_{2-6}$hydroxyalkyl, C$_{2-6}$-aminoalkyl, —COR$^a$, aryl and heteroaryl; or R$^b$, R$^c$ and the nitrogen atom to which they are attached together form a 4- to 7-membered ring optionally having an additional heteroatom selected from NR$^d$, O and S(O)$_r$, wherein said ring being optionally substituted with 1 to 4 groups independently selected from halogen, cyano and C$_{1-6}$cyanoalkyl;
r is 0, 1 or 2,
R$^d$ is selected from the group consisting of (1) H, (2) C$_{1-6}$alkyl, (3) C(O)C$_{1-6}$alkyl,
R$^x$ is selected from the group consisting of (1) oxo, (2) OR$^a$, (3) cyano, (4) halogen, (5) NR$^b$R$^c$, (6) CO$_2$R$^a$, (7) CONR$^b$R$^c$; (8) —COR$^a$ and (9) S(O)$_r$R$^a$;
R$^y$ is selected from the group consisting of (1) a member of R$^z$, and (2) oxo;
R$^z$ is selected from the group consisting of (1) OR$^a$, (2) cyano, (3) halogen, (4) COR$^a$, (5) CO$_2$R$^a$, (6) nitro, (7) NR$^b$R$^c$, and (8) CONR$^b$R$^c$; (9) C$_{1-6}$alkyl, (10) C$_{1-6}$haloalkyl, (11) C$_{1-6}$hydroxyalkyl, (12) C$_{1-6}$cyanoalkyl, (13) C$_{1-6}$(C$_{1-3}$alkoxy)alkyl, (14) C$_{1-6}$ aminoalkyl, (15) C$_{1-6}$ mono(C$_{1-3}$alkylamino)alkyl, (16) C$_{1-6}$di(C$_{1-3}$alkylamino)alkyl, (17) C$_{2-6}$alkenyl, (18) C$_{2-6}$alkynyl, (19) —SO$_2$NR$^b$R$^c$, (20) —NR$^b$SO$_2$C$_{1-6}$alkyl and (21) —NR$^b$SO$_2$aryl.

In another embodiment of formula I are compounds encompassed within formula Ia, Ib, Ic or Id wherein R$^6$ is H, and all other variables are as defined in formula I.

In another embodiment of formula I are compounds encompassed within formula Ia, Ib, Ic or Id wherein R$^1$ and R$^2$ are each independently H or methyl, and all other variables are as defined in formula I. In one subset thereof each of R$^1$ and R$^2$ is H.

In another embodiment of formula I are compounds encompassed within formula Ia, Ib, Ic or Id wherein R$^{4a}$, R$^{4b}$, R$^{5a}$ and R$^{5b}$ are each independently H or methyl, and all other variables are as defined in formula I. In one subset thereof each of R$^{4a}$, R$^{4b}$, R$^{5a}$ and R$^{5b}$ is H.

In another embodiment of compounds of formula I are compounds of formula Ie wherein the variables are as defined in formula I:

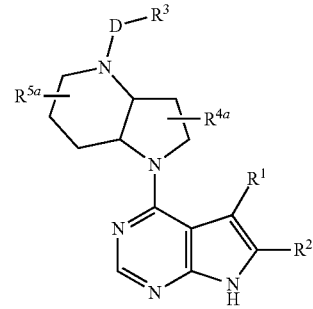

and pharmaceutically acceptable salts thereof.

In another embodiment of formula I are compounds encompassed within formula Ia, Ib, Ic, Id, Ie, or Ig wherein D is —C(O)O—, and all other variables are as defined in formula I. In one subset thereof R$^1$, R$^2$, R$^{4a}$, R$^{4b}$, R$^{5a}$ and R$^{5b}$ are each independently H or methyl. In another subset thereof each of R$^1$, R$^2$, R$^{4a}$, R$^{4b}$, R$^{5a}$ and R$^{5b}$ is H.

In another embodiment of formula I are compounds encompassed within formula Ia, Ib, Ic, Id, Ie or Ig wherein D is —C(O)—, and all other variables are as defined in formula I. In one subset thereof R$^1$, R$^2$, R$^{4a}$, R$^{4b}$, R$^{5a}$ and R$^{5b}$ are each independently H or methyl. In another subset thereof each of $R^1$, $R^2$, $R^{4a}$, $R^{4b}$, $R^{5a}$ and $R^{5b}$ is H.

In another embodiment of formula I are compounds encompassed within formula Ia, Ib, Ic, Id, Ie, or Ig wherein D is —C(O)NH—, and all other variables are as defined in formula I. In one subset thereof $R^1$, $R^2$, $R^{4a}$, $R^{4b}$, $R^{5a}$ and $R^{5b}$ are each independently H or methyl. In another subset thereof each of $R^1$, $R^2$, $R^{4a}$, $R^{4b}$, $R^{5a}$ and $R^{5b}$ is H.

In another embodiment of formula I are compounds encompassed within formula Ia, Ib, Ic, Id, Ie, or Ig wherein D is —SO$_2$—, and all other variables are as defined in formula I. In one subset thereof $R^1$, $R^2$, $R^{4a}$, $R^{4b}$, $R^{5a}$ and $R^{5b}$ are each independently H or methyl. In another subset thereof each of $R^1$, $R^2$, $R^{4a}$, $R^{4b}$, $R^{5a}$ and $R^{5b}$ is H.

In another embodiment of formula I are compounds encompassed within formula Ia, Ib, Ic, Id, Ie, or Ig wherein D is —CONR$^a$—, and all other variables are as defined in formula I. In one subset thereof $R^1$, $R^2$, $R^{4a}$, $R^{4b}$, $R^{5a}$ and $R^{5b}$ are each independently H or methyl. In another subset thereof each of $R^1$, $R^2$, $R^{4a}$, $R^{4b}$, $R^{5a}$ and $R^{5b}$ is H.

In another embodiment of formula I are compounds encompassed within formula Ia, Ib, Ic, Id, Ie or Ig wherein $R^3$ is (1) $C_{1-6}$alkyl, (2)-L-$C_{3-10}$cycloalkyl, (3)-L-aryl, (4)-L-heteroaryl, (5) -L-heterocyclyl, wherein alkyl is optionally substituted with 1 to 5 groups independently selected from $R^x$; cycloalkyl and heterocyclyl are optionally substituted with 1 to 5 groups independently selected from. $R^y$; and aryl and heteroaryl are optionally substituted with 1 to 5 groups independently selected from $R^z$; L is a bond, $C_{1-6}$alkylene, arylene, heteroarylene, cycloalkylene or heterocyclyene; wherein alkylene is optionally substituted with 1 to 5 groups independently selected from $R^x$, aryl and heteroaryl (aryl and heteroaryl being optionally substituted with 1 to 3 groups independently selected from $R^z$); cycloalkylene or heterocyclyene are optionally substituted with 1 to 5 groups independently selected from $R^y$; and arylene and heteroarylene are optionally substituted with 1 to 5 groups independently selected from $R^z$; and all other variables are as defined in formula I. In one subset thereof $R^1$, $R^2$, $R^{4a}R^{4b}$, $R^{5a}$ and $R^{5b}$ are each independently H or methyl. In another subset thereof each of $R^1$, $R^2$, $R^{4a}$, $R^{4b}$, $R^{5a}$ and $R^{5b}$ is H.

Representative compounds of the instant invention include, but are not limited to, the following compounds and their pharmaceutically acceptable salts:

benzyl 1-(7H-pyrrolo[2,3-d]pyrimidin-4-yl)octahydro-4H-pyrrolo[3,2-b]pyridine-4-carboxylate;

[3aS,7aS]-4-(octahydro-1H-pyrrolo[3,2-b]pyridin-1-yl)-7H-pyrrolo[2,3-d]pyrimidine;

[3aR,7aR]-4-(octahydro-1H-pyrrolo[3,2-b]pyridin-1-yl)-7H-pyrrolo[2,3-d]pyrimidine;

pyridin-3-ylmethyl 1-(7H-pyrrolo[2,3-d]pyrimidin-4-yl)octahydro-4H-pyrrolo[3,2-b]-pyridine-4-carboxylate;

4-fluorobenzyl 1-(7H-pyrrolo[2,3-d]pyrimidin-4-yl)octahydro-4H-pyrrolo[3,2-b]-pyridine-4-carboxylate;

butyl 1-(7H-pyrrolo[2,3-d]pyrimidin-4-yl)octahydro-4H-pyrrolo[3,2-b]pyridine-4-carboxylate;

3-methoxybenzyl 1-(7H-pyrrolo[2,3-d]pyrimidin-4-yl)octahydro-4H-pyrrolo[3,2-b]-pyridine-4-carboxylate;

3-pyridin-3-ylpropyl 1-(7H-pyrrolo[2,3-d]pyrimidin-4-yl)octahydro-4H-pyrrolo[3,2-b]-pyridine-4-carboxylate;

4-chlorobenzyl 1-(7H-pyrrolo[2,3-d]pyrimidin-4-yl)octahydro-4H-pyrrolo[3,2-b]-pyridine-4-carboxylate;

3-phenylpropyl 1-(7H-pyrrolo[2,3-d]pyrimidin-4-yl)octahydro-4H-pyrrolo[3,2-b]-pyridine-4-carboxylate;

2-phenylethyl 1-(7H-pyrrolo[2,3-d]pyrimidin-4-yl)octahydro-4H-pyrrolo[3,2-b]-pyridine-4-carboxylate;

3-fluorobenzyl 1-(7H-pyrrolo[2,3-d]pyrimidin-4-yl)octahydro-4H-pyrrolo[3,2-b]-pyridine-4-carboxylate;

tetrahydro-2H-pyran-4-yl 1-(7H-pyrrolo[2,3-d]pyrimidin-4-yl)octahydro-4H-pyrrolo[3,2-b]pyridine-4-carboxylate;

2,3-dihydro-1H-inden-2-yl 1-(7H-pyrrolo[2,3-d]pyrimidin-4-yl)octahydro-4H-pyrrolo[3,2-b]pyridine-4-carboxylate;

pyridin-2-ylmethyl 1-(7H-pyrrolo[2,3-d]pyrimidin-4-yl)octahydro-4H-pyrrolo[3,2-b]-pyridine-4-carboxylate;

pyridin-4-ylmethyl 1-(7H-pyrrolo[2,3-d]pyrimidin-4-yl)octahydro-4H-pyrrolo[3,2-b]-pyridine-4-carboxylate;

4-methoxybenzyl 1-(7H-pyrrolo[2,3-d]pyrimidin-4-yl)octahydro-4H-pyrrolo[3,2-b]-pyridine-4-carboxylate;

naphthalen-2-ylmethyl 1-(7H-pyrrolo[2,3-d]pyrimidin-4-yl)octahydro-4H-pyrrolo[3,2-b]pyridine-4-carboxylate;

3-methylbenzyl 1-(7H-pyrrolo[2,3-d]pyrimidin-4-yl)octahydro-4H-pyrrolo[3,2-b]-pyridine-4-carboxylate;

4-methylbenzyl 1-(7H-pyrrolo[2,3-d]pyrimidin-4-yl)octahydro-4H-pyrrolo[3,2-b]-pyridine-4-carboxylate;

pyrazin-2-ylmethyl 1-(7H-pyrrolo[2,3-d]pyrimidin-4-yl)octahydro-4H-pyrrolo[3,2-b]-pyridine-4-carboxylate;

pyridin-3-ylmethyl (3aR,7aR)-1-(7H-pyrrolo[2,3-d]pyrimidin-4-yl)octahydro-4H-pyrrolo[3,2-b]pyridine-4-carboxylate;

3-(methoxycarbonyl)benzyl (3aR,7aR)-1-(7H-pyrrolo[2,3-d]pyrimidin-4-yl)octahydro-4H-pyrrolo[3,2-b]pyridine-4-carboxylate;

2-[4-(methoxycarbonyl)phenyl]ethyl (3aR,7aR)-1-(7H-pyrrolo[2,3-d]pyrimidin-4-yl)octahydro-4H-pyrrolo[3,2-b]pyridine-4-carboxylate;

3-[4-(methoxycarbonyl)phenyl]propyl (3aR,7aR)-1-(7H-pyrrolo[2,3-d]pyrimidin-4-yl)octahydro-4H-pyrrolo[3,2-b]pyridine-4-carboxylate;

(1R)-1-phenylethyl 1-(7H-pyrrolo[2,3-d]pyrimidin-4-yl)octahydro-4H-pyrrolo[3,2-b]-pyridine-4-carboxylate;

(1S)-1-phenylethyl 1-(7H-pyrrolo[2,3-d]pyrimidin-4-yl)octahydro-4H-pyrrolo[3,2-b]-pyridine-4-carboxylate;

4-(methoxycarbonyl)benzyl 1-(7H-pyrrolo[2,3-d]pyrimidin-4-yl)octahydro-4H-pyrrolo[3,2-b]pyridine-4-carboxylate;

3-(methoxyeaxbonyl)phenyl 1-(7H-pyrrolo[2,3-d]pyrimidin-4-yl)octahydro-4H-pyrrolo[3,2-b]pyridine-4-carboxylate;

2-(1,1-dioxidothiomorpholin-4-yl)ethyl (3 aR,7 aR)-1-(7H-pyrrolo[2,3-d]pyrimidin-4-yl)octahydro-4H-pyrrolo[3,2-b]pyridine-4-carboxylate;

2-(2,3-dihydro-1-benzofuran-5-yl)ethyl (3aR,7aR)-1-(7H-pyrrolo[2,3-d]pyrimidin-4-yl)octahydro-4H-pyrrolo[3,2-b]pyridine-4-carboxylate;

2-[2-(methoxycarbonyl)cyclopropyl]ethyl (3aR,7aR)-1-(7H-pyrrolo[2,3-d]pyrimidin-4-yl)octahydro-4H-pyrrolo[3,2-b]pyridine-4-carboxylate;

2-fluoroethyl (3aR,7aR)-1-(7H-pyrrolo[2,3-d]pyrimidin-4-yl)octahydro-4H-pyrrolo[3,2-b]pyridine-4-carboxylate;

cyclopropylmethyl (3aR,7aR)-1-(7H-pyrrolo[2,3-d]pyrimidin-4-yl)octahydro-4H-pyrrolo[3,2-b]pyridine-4-carboxylate;

cyclohexyl (3aR,7aR)-1-(7H-pyrrolo[2,3-d]pyrimidin-4-yl)octahydro-4H-pyrrolo[3,2-b]pyridine-4-carboxylate;

2-fluorobenzyl (3aR,7aR)-1-(7H-pyrrolo[2,3-d]pyrimidin-4-yl)octahydro-4H-pyrrolo[3,2-b]pyridine-4-carboxylate;

2-naphthalen-1-ylethyl (3aR,7aR)-1-(7H-pyrrolo[2,3-d]pyrimidin-4-yl)octahydro-4H-pyrrolo[3,2-b]pyridine-4-carboxylate;

2-methoxyethyl (3aR,7aR)-1-(7H-pyrrolo[2,3-d]pyrimidin-4-yl)octahydro-4H-pyrrolo[3,2-b]pyridine-4-carboxylate;

2-(2-oxopyrrolidin-1-yl)ethyl (3aR,7aR)-1-(7H-pyrrolo[2,3-d]pyrimidin-4-yl)octahydro-4H-pyrrolo[3,2-b]pyridine-4-carboxylate;

2-pyridin-2-ylethyl (3aR,7 aR)-1-(7H-pyrrolo[2,3-d]pyrimidin-4-yl)octahydro-4H-pyrrolo[3,2-b]pyridine-4-carboxylate;

2-(dimethylamino)ethyl(3aR,7aR)-1-(7H-pyrrolo[2,3-d]pyrimidin-4-yl)octahydro-4H-pyrrolo[3,2-b]pyridine-4-carboxylate;

2-morpholin-4-ylethyl (3aR,7aR)-1-(7H-pyrrolo[2,3-d]pyrimidin-4-yl)octahydro-4H-pyrrolo[3,2-b]pyridine-4-carboxylate;

2-pyrrolidin-1-ylethyl (3aR,7aR)-1-(7H-pyrrolo[2,3-d]pyrimidin-4-yl)octahydro-4H-pyrrolo[3,2-b]pyridine-4-carboxylate;

2-(4-methylpiperazin-1-yl)ethyl(3aR,7aR)-1-(7H-pyrrolo[2,3-d]pyrimidin-4-yl)octahydro-4H-pyrrolo[3,2-b]pyridine-4-carboxylate;

(1-methylpiperidin-4-yl)methyl (3 aR,7 aR)-1-(7H-pyrrolo[2,3-d]pyrimidin-4-yl)octahydro-4H-pyrrolo[3,2-b]pyridine-4-carboxylate;

2-(2,2,2-trifluoroethoxy)ethyl (3aR,7aR)-1-(7H-pyrrolo[2,3-d]pyrimidin-4-yl)octahydro-4H-pyrrolo[3,2-b]pyridine-4-carboxylate;

2-(3,5-difluorophenyl)ethyl (3aR,7aR)-1-(7H-pyrrolo[2,3-d]pyrimidin-4-yl)octahydro-4H-pyrrolo[3,2-b]pyridine-4-carboxylate;

2-(1H-indol-1-yl)ethyl (3aR,7aR)-1-(7H-pyrrolo[2,3-d]pyrimidin-4-yl)octahydro-4H-pyrrolo[3,2-b]pyridine-4-carboxylate;

cyclohexylmethyl (3aR,7aR)-1-(7H-pyrrolo[2,3-d]pyrimidin-4-yl)octahydro-4H-pyrrolo[3,2-b]pyridine-4-carboxylate;

3-phenylpropyl (3aR,7aR)-1-(7H-pyrrolo[2,3-d]pyrimidin-4-yl)octahydro-4H-pyrrolo[3,2-b]pyridine-4-carboxylate;

3-pyridin-3-ylpropyl (3 aR,7 aR)-1-(7H-pyrrolo[2,3-d]pyrimidin-4-yl)octahydro-4H-pyrrolo[3,2-b]pyridine-4-carboxylate;

4-(methoxycarbonyl)benzyl (3aR,7aR)-1-(7H-pyrrolo[2,3-d]pyrimidin-4-yl)octahydro-4H-pyrrolo[3,2-b]pyridine-4-carboxylate;

4-(methoxycarbonyl)benzyl (3aS,7aS)-1-(7H-pyrrolo[2,3-d]pyrimidin-4-yl)octahydro-4H-pyrrolo[3,2-b]pyridine-4-carboxylate;

4-[({[(3aR,7aR)-1-(7H-pyrrolo[2,3-d]pyrimidin-4-yl)octahydro-4H-pyrrolo[3,2-b]pyridine-4-yl]carbonyl}oxy)methyl]benzoic acid;

4-(dimethylcarbamoyl)benzyl (3aR,7aR)-1-(7H-pyrrolo[2,3-d]pyrimidin-4-yl)octahydro-4H-pyrrolo[3,2-b]pyridine-4-carboxylate;

4-carbamoylbenzyl (3aR,7aR)-1-(7H-pyrrolo[2,3-d]pyrimidin-4-yl)octahydro-4H-pyrrolo[3,2-b]pyridine-4-carboxylate;

4-(methylcarbamoyl)benzyl (3aR,7aR)-1-(7H-pyrrolo[2,3-d]pyrimidin-4-yl)octahydro-4H-pyrrolo[3,2-b]pyridine-4-carboxylate;

4-{[2-(dimethylamino)ethyl]carbamoyl}benzyl (3aR,7aR)-1-(7H-pyrrolo[2,3-d]pyrimidin-4-yl)octahydro-4H-pyrrolo[3,2-b]pyridine-4-carboxylate;

4-{[2-(dimethylamino)ethyl](methyl)carbamoyl}benzyl (3aR,7aR)-1-(7H-pyrrolo[2,3-d]pyrimidin-4-yl)octahydro-4H-pyrrolo[3,2-b]pyridine-4-carboxylate;

4-{[(tert-butoxycarbonyl)amino]methyl}benzyl (3 aR, 7aR)-1-(7H-pyrrolo[2,3-d]pyrimidin-4-yl)octahydro-4-pyrrolo[3,2-b]pyridine-4-carboxylate;

(1S)-1-phenylethyl (3aR,7 aR)-1-(7H-pyrrolo[2,3-d]pyrimidin-4-yl)octahydro-4-pyrrolo[3,2-b]pyridine-4-carboxylate;

(1R and 1S)-3-(morpholin-4-yl)-1-phenylpropyl (3aR,7aR)-1-(7H-pyrrolo[2,3-d]pyrimidin-4-yl)octahydro-4-pyrrolo[3,2-b]pyridine-4-carboxylate;

4-(aminomethyl)benzyl(3aR,7aR)-1-(7H-pyrrolo[2,3-d]pyrimidin-4-yl)octahydro-4H-pyrrolo[3,2-b]pyridine-4-carboxylate;

4-(hydroxymethyl)benzyl (3aR,7aR)-1-(7H-pyrrolo[2,3-d]pyrimidin-4-yl)octahydro-4H-pyrrolo[3,2-b]pyridine-4-carboxylate;

tert-butyl (3 aR,7 aR)-1-(7H-pyrrolo[2,3-d]pyrimidin-4-yl)octahydro-4H-pyrrolo[3,2-b]pyridin-4-carboxylate;

3-oxo-3-[(3aR,7aR)-1-(7H-pyrrolo[2,3-d]pyrimidin-4-yl)octahydro-4H-pyrrolo[3,2-b]pyridin-4-yl]propanenitrile;

methyl 4-{3-[(3aR,7aR)-1-(7H-pyrrolo[2,3-d]pyrimidin-4-yl)octahydro-4H-pyrrolo[3,2-b]pyridin-4-yl]propyl}benzoate;

4-{3-[(3aR,7aR)-1-(7H-pyrrolo[2,3-d]pyrimidin-4-yl)octahydro-4H-pyrrolo[3,2-b]pyridin-4-yl]propyl}benzoic acid;

benzyl 1-(6-methyl-7H-pyrrolo[2,3-d]pyrimidin-4-yl)octahydro-4H-pyrrolo[3,2-b]-pyridine-4-carboxylate;

benzyl 4-(7H-pyrrolo[2,3-d]pyrimidin-4-yl)octahydro-1H-pyrrolo[3,2-b]pyridine-1-carboxylate;

2-hydroxy-1-[1-(7H-pyrrolo[2,3-d]pyrimidin-4-yl)octahydro-4H-pyrrolo[3,2-b]pyridine-4-yl]ethanone;

(2S)-3,3,3-trifluoro-2-methoxy-2-phenyl-1-[(3aR,7aR)-1-(7H-pyrrolo[2,3-d]pyrimidin-4-yl)octahydro-4H-pyrrolo[3,2-b]pyridine-4-yl]propan-1-one;

(2R)-3,3,3-trifluoro-2-methoxy-2-phenyl-1-[(3aR,7 aR)-1-(7H-pyrrolo[2,3-d]pyrimidin-4-yl)octahydro-4H-pyrrolo[3,2-b]pyridine-4-yl]propan-1-one;

benzyl 7-methyl-1-(7H-pyrrolo[2,3-d]pyrimidin-4-yl)octahydro-4H-pyrrolo[3,2-b]-pyridine-4-carboxylate;

4-(4-benzyl-7-methyloctahydro-1H-pyrrolo[3,2-b]pyridin-1-yl)-7H-pyrrolo[2,3-d]-pyrimidine;

3-[7-methyl-1-(7H-pyrrolo[2,3-d]pyrimidin-4-yl)octahydro-4H-pyrrolo[3,2-b]pyridin-4-yl]-3-oxopropanenitrile;

methyl 4-[({[(3aR,7aR)-1-(7H-pyrrolo[2,3-d]pyrimidin-4-yl)octahydro-4H-pyrrolo[3,2-b]pyridine-4-yl]carbonyl}amino)methyl]benzoate;

methyl 4-[(methyl{[(3aR,7aR)-1-(7H-pyrrolo[2,3-d]pyrimidin-4-yl)octahydro-4H-pyrrolo[3,2-b]pyridin-4-yl]carbonyl}amino)methyl]benzoate;

4-[({[(3aR,7aR)-1-(7H-pyrrolo[2,3-d]pyrimidin-4-yl)octahydro-4H-pyrrolo[3,2-b]-pyridin-4-yl]carbonyl}amino)methyl]benzoic acid;

methyl 4-{3-oxo-3-[(3aR,7aR)-1-(7H-pyrrolo[2,3-d]pyrimidin-4-yl)octahydro-4H-pyrrolo[3,2-b]pyridine-4-yl]propyl}benzoate;

4-{3-oxo-3-[(3aR,7aR)-1-(7H-pyrrolo[2,3-d]pyrimidin-4-yl)octahydro-4H-pyrrolo[3,2-b]pyridin-4-yl]propyl}benzoic acid;

4-[2-({[(3aR,7aR)-1-(7H-pyrrolo[2,3-d]pyrimidin-4-yl)octahydro-4H-pyrrolo[3,2-b]-pyridin-4-yl]carbonyl}oxy)ethyl]benzoic acid;

4-{4-[(4-morpholin-4-ylphenyl)carbonyl]octahydro-1H-pyrrolo[3,2-b]pyridin-1-yl}-7H-pyrrolo[2,3-d]pyrimidine;

4-(4-pentanoyloctahydro-1H-pyrrolo[3,2-b]pyridin-1-yl)-7H-pyrrolo[2,3-d]pyrimidine;

4-[4-(phenylcarbonyl)octahydro-1H-pyrrolo[3,2-b]pyridin-1-yl]-7H-pyrrolo[2,3-d]-pyrimidine;

4-{4-[(4-methoxyphenyl)acetyl]octahydro-1H-pyrrolo[3,2-b]pyridin-1-yl}-7H-pyrrolo[2,3-d]pyrimidine;

4-(4-{[4-(trifluoromethyl)phenyl]acetyl}octahydro-1H-pyrrolo[3,2-b]pyridin-1-yl)-7H-pyrrolo[2,3-d]pyrimidine;

4-(4-{[4-(4-methylpiperazin-1-yl)phenyl]carbonyl}octahydro-1H-pyrrolo[3,2-b]pyridin-1-yl)-7H-pyrrolo[2,3-d]pyrimidine;

4-[(3aR,7aR)-4-propanoyloctahydro-1H-pyrrolo[3,2-b]pyridin-1-yl]-7H-pyrrolo[2,3-d]-pyrimidine;

4-[(3aR,7aR)-4-(methoxyacetyl)octahydro-1H-pyrrolo[3,2-b]pyridin-1-yl]-7H-pyrrolo[2,3-d]pyrimidine;

4-[(3 aR,7aR)-4-(furan-2-ylcarbonyl)octahydro-1H-pyrrolo[3,2-b]pyridin-1-yl]-7H-pyrrolo[2,3-d]pyrimidine;

4-[(3aR,7aR)-4-(pyridin-3-ylcarbonyl)octahydro-1H-pyrrolo[3,2-b]pyridin-1-yl]-7H-pyrrolo[2,3-d]pyrimidine;

4-[(3aR,7aR)-4-(pyridin-2-ylcarbonyl)octahydro-1H-pyrrolo[3,2-b]pyridin-1-yl]-7H-pyrrolo[2,3-d]pyrimidine;

4-[(3aR,7aR)-4-(pyridin-4-ylcarbonyl)octahydro-1H-pyrrolo[3,2-b]pyridin-1-yl]-7H-pyrrolo[2,3-d]pyrimidine;

4-[(3aR,7aR)-4-(pyrazin-2-ylcarbonyl)octahydro-1H-pyrrolo[3,2-b]pyridin-1-yl]-7H-pyrrolo[2,3-d]pyrimidine;

4-{(3aR,7aR)-4[(5-methylisoxazol-3-yl)carbonyl]octahydro-1H-pyrrolo[3,2-b]pyridin-1-yl}-7H-pyrrolo[2,3-d]pyrimidine;

4-[(3aR,7aR)-4-(cyclohexylcarbonyl)octahydro-1H-pyrrolo[3,2-b]pyridin-1-yl]-7H-pyrrolo[2,3-d]pyrimidine;

1-{2-oxo-2-[(3aR,7aR)-1-(7H-pyrrolo[2,3-d]pyrimidin-4-yl)octahydro-4H-pyrrolo[3,2-b]pyridin-4-yl]ethyl}pyrrolidin-2-one;

4-{(3aR,7aR)-4-[(2-chlorophenyl)carbonyl]octahydro-1H-pyrrolo[3,2-b]pyridin-1-yl}-7H-pyrrolo[2,3-d]pyrimidine;

4-{(3aR,7aR)-4-[(3-chlorophenyl)carbonyl]octahydro-1H-pyrrolo[3,2-b]pyridin-1-yl}-7H-pyrrolo[2,3-d]pyrimidine;

4-[(3aR,7aR)-4-(1H-indol-2-ylcarbonyl)octahydro-1H-pyrrolo[3,2-b]pyridin-1-yl]-7H-pyrrolo[2,3-d]pyrimidine;

4-[(3aR,7aR)-4-(naphthalen-1-ylcarbonyl)octahydro-1H-pyrrolo[3,2-b]pyridin-1-yl]-7H-pyrrolo[2,3-d]pyrimidine;

4-{(3aR,7aR)-4-[(1-methyl-1H-indol-2-yl)carbonyl]octahydro-1H-pyrrolo[3,2-b]pyridin-1-yl}-7H-pyrrolo[2,3-d]pyrimidine;

4-{(3aR,7aR)-4-[(3-morpholin-4-ylphenyl)carbonyl]octahydro-1H-pyrrolo[3,2-b]pyridin-1-yl}-7H-pyrrolo[2,3-d]pyrimidine;

4-[(3aR,7aR)-4-(biphenyl-2-ylcarbonyl)octahydro-1H-pyrrolo[3,2-b]pyridin-1-yl]-7H-pyrrolo[2,3-d]pyrimidine;

4-[(3aR,7aR)-4-(diphenylacetyl)octahydro-1H-pyrrolo[3,2-b]pyridin-1-yl]-7H-pyrrolo[2,3-d]pyrimidine;

4-[(3aR,7aR)-4-(imidazo[1,2-a]pyridin-2-ylcarbonyl)octahydro-1H-pyrrolo[3,2-b]pyridin-1-yl]-7H-pyrrolo[2,3-d]pyrimidine;

4-[(3aR,7aR)-4-(naphthalen-2-ylcarbonyl)octahydro-1H-pyrrolo[3,2-b]pyridin-1-yl]-7H-pyrrolo[2,3-d]pyrimidine;

4-[(3aR,7aR)-4-(imidazo[1,2-a]pyrimidin-2-ylcarbonyl)octahydro-1H-pyrrolo[3,2-b]pyridin-1-yl]-7H-pyrrolo[2,3-d]pyrimidine;

4-[(3aR,7aR)-4-(thiophen-2-ylcarbonyl)octahydro-1H-pyrrolo[3,2-b]pyridin-1-yl]-7H-pyrrolo[2,3-d]pyrimidine;

4-{[(3aR,7aR)-1-(7H-pyrrolo[2,3-d]pyrimidin-4-yl)octahydro-4H-pyrrolo[3,2-b]pyridin-4-yl]carbonyl}benzonitrile;

4-[(3aR,7aR)-4-{[(1R,2S)-2-propylcyclopropyl]carbonyl}octahydro-1H-pyrrolo[3,2-b]pyridin-1-yl]-7H-pyrrolo[2,3-d]pyrimidine;

3-{[(3aR,7aR)-1-(7H-pyrrolo[2,3-d]pyrimidin-4-yl)octahydro-4H-pyrrolo[3,2-b]pyridin-4-yl]carbonyl}benzonitrile;

4-[(3aR,7aR)-4-(thiophen-3-ylcarbonyl)octahydro-1H-pyrrolo[3,2-b]pyridin-1-yl]-7H-pyrrolo[2,3-d]pyrimidine;

2-{[(3aR,7aR)-1-(7H-pyrrolo[2,3-d]pyrimidin-4-yl)octahydro-4H-pyrrolo[3,2-b]pyridin-4-yl]carbonyl}benzonitrile;

4-[(3aR,7aR)-4-(phenylcarbonyl)octahydro-1H-pyrrolo[3,2-b]pryidin-1-yl]-7H-pyrrolo[2,3-d]pyrimidine;

N,N-dimethyl-4-{[(3aR,7aR)-1-(7H-pyrrolo[2,3-d]pyrimidin-4-yl)octahydro-4H-pyrrolo[3,2-b]pyridin-4-yl]carbonyl}piperidine-1-carboxamide;

2-{2-oxo-2-[(3aR,7aR)-1-(7H-pyrrolo[2,3-d]pyrimidin-4-yl)octahydro-4H-pyrrolo[3,2-b]pyridin-4-yl]ethyl}-1,2,3,4-tetrahydroisoquinoline;

5-{[(3aR,7aR)-1-(7H-pyrrolo[2,3-d]pyrimidin-4-yl)octahydro-4H-pyrrolo[3,2-b]pyridin-4-yl]carbonyl}isoquinoline;

4-[(3aR,7aR)-4-(2,3-dihydro-1,4-benzodioxin-2-ylcarbonyl)octahydro-1H-pyrrolo[3,2-b]pyridin-1-yl]-7H-pyrrolo[2,3-d]pyrimidine;

8-{[(3aR,7aR)-1-(7H-pyrrolo[2,3-d]pyrimidin-4-yl)octahydro-4H-pyrrolo[3,2-b]pyridin-4-yl]carbonyl}isoquinoline;

4-{[(3aR,7aR)-1-(7H-pyrrolo[2,3-d]pyrimidin-4-yl)octahydro-4H-pyrrolo[3,2-b]pyridin-4-yl]carbonyl}isoquinoline;

4-{(3aR,7aR)-4-[(5-cyclopropyl-1,3-oxazol-4-yl)carbonyl]octahydro-1H-pyrrolo[3,2-b]pyridin-1-yl}-7H-pyrrolo[2,3-d]pyrimidine;

4-[(3aR,7aR)-4-(2-methyl-3-phenylpropanoyl)octahydro-1H-pyrrolo[3,2-b]pyridin-1-yl]-7H-pyrrolo[2,3-d]pyrimidine;

4-[(3aR,7aR)-4-(2-morpholin-4-ylpropanoyl)octahydro-1H-pyrrolo[3,2-b]pyridin-1-yl]7H-pyrrolo[2,3-d]pyrimidine;

3-{[(3aR,7aR)-1-(7H-pyrrolo[2,3-d]pyrimidin-4-yl)octahydro-4H-pyrrolo[3,2-b]pyridin-4-yl]carbonyl}quinoline;

4-[(3aR,7aR)-4-(1H-pyrrolo[3,2-c]pyridin-3-ylcarbonyl)octahydro-1H-pyrrolo[3,2-b]pyridin-1-yl]-7H-pyrrolo[2,3-d]pyrimidine;

2-oxo-1-phenyl-2-[(3aR,7aR)-1-(7H-pyrrolo[2,3-d]pyrimidin-4-yl)octahydro-4H-pyrrolo[3,2-b]pyridin-4-yl]ethanol;

1-{[(3aR,7aR)-1-(7H-pyrrolo[2,3-d]pyrimidin-4-yl)octahydro-4H-pyrrolo[3,2-b]pyridin-4-yl]carbonyl}isoquinoline;

4-[(3aR,7aR)-4-(6H-thieno[2,3-b]pyrrol-5-ylcarbonyl)octahydro-1H-pyrrolo[3,2-b]pryidin-1-yl]7H-pyrrolo[2,3-d]pyrimidine;

4-[(3aR,7aR)-4-(imidazo[1,2-a]pyrimidin-2-ylcarbonyl)octahydro-1H-pyrrolo[3,2-b]pyridin-1-yl]-7H-pyrrolo[2,3-d]pyrimidine;

4-{(3aR,7aR)-4-[(1-methyl-1H-pyrrolo[2,3-b]pyridin-5-yl)carbonyl]octahydro-1H-pyrrolo[3,2-b]pyridin-1-yl}-7H-pyrrolo[2,3-d]pyrimidine;

8-{[(3aR,7aR)-1-(7H-pyrrolo[2,3-d]pyrimidin-4-yl)octahydro-4H-pyrrolo[3,2-b]pyridin-4-yl]carbonyl}quinoline;

4-[(3aR,7aR)-4-(indolizin-2-ylcarbonyl)octahydro-1H-pyrrolo[3,2-b]pyridin-1-yl]-7H-pyrrolo[2,3-d]pyrimidine;

4-[(3aR,7aR)-4-(1H-benzimidazol-1-ylacetyl)octahydro-1H-pyrrolo[3,2-b]pyridin-1-yl]-7H-pyrrolo[2,3-d]pyrimidine;

4-[(3aR,7aR)-4-(2H-indazol-2-ylacetyl)octahydro-1H-pyrrolo[3,2-b]pyridin-1-yl]-7H-pyrrolo[2,3-d]pyrimidine;

4-{(3aR,7aR)-4-[3-(1-methylpiperidin-3-yl)propanoyl]octahydro-1H-pyrrolo[3,2-b]pyridin-1-yl}-7H-pyrrolo[2,3-d]pyrimidine;

(2S and 2R)-2-methyl-3-phenyl-1-[(3aR,7aR)-1-(7H-pyrrolo[2,3-d]pyrimidin-4-yl)octahydro-4H-pyrrolo[3,2-b]pyridine-4-yl]propan-1-one;

4-[(3aR,7aR)-4-{[3-(3-fluorophenyl)isoxazol-5-yl]carbonyl}octahydro-1H-pyrrolo[3,2b]pryidin-1-yl]-7H-pyrrolo[2,3-d]pyrimidine;

4-{(3aR,7aR)-4-[(1-methyl-1H-pyrrolo[2,3-b]pyridin-5-yl)carbonyl]octahydro-1H-pyrrolo[3,2-b]pyridin-1-yl}-7H-pyrrolo[2,3-d]pyrimidine;

4-{(3aR,7aR)-4-[(1-methyl-1H-indazol-5-yl)acetyl]octahydro-1H-pyrrolo[3,2-b]pyridin-1-yl}-7H-pyrrolo[2,3-d]pyrimidine;

4-{(3aR,7aR)-4-[(7-chloroimidazo[1,2-a]pyridin-2-yl)carbonyl]octahydro-1H-pyrrolo[3,2-b]pyridin-1-yl}-7H-pyrrolo[2,3-d]pyrimidine;

4-{[(3aR,7aR)-1-(7H-pyrrolo[2,3-d]pyrimidin-4-yl)octahydro-4H-pyrrolo[3,2-b]pyridin-4-yl]carbonyl}quinoline;

6-{[(3aR,7aR)-1-(7H-pyrrolo[2,3-d]pyrimidin-4-yl)octahydro-4H-pyrrolo[3,2-b]pyridin-4-yl]carbonyl}-2,3-dihydro-1H-isoindol-1-one;

benzyl 1-(1H-pyrrolo[2,3-b]pyridine-4-yl)octahydro-4H-pyrrolo[3,2-b]pyridine-4-carboxylate;

4-[4-(5-phenyl-1,3,4-oxadiazol-2-yl)octahydro-1H-pyrrolo[3,2-b]pyridin-1-yl]-7H-pyrrolo[2,3-d]pyrimidine;

4-{(3aR,7aR)-4-[(1-methylethyl)sulfonyl]octahydro-1H-pyrrolo[3,2-b]pyridin-1-yl}-7H-pyrrolo[2,3-d]pyrimidine;

4-{(3aR,7aR)-4-[(2-phenylethyl)sulfonyl]octahydro-1H-pyrrolo[3,2-b]pyridin-1-yl}-7H-pyrrolo[2,3-d]pyrimidine;

4-[(3aR,7aR)-4-(ethylsulfonyl)octahydro-1H-pyrrolo[3,2-b]pyridin-1-yl]-7H-pyrrolo[2,3-d]pyrimidine;

4-[(3aR,7aR)-4-(furan-2-ylsulfonyl)octahydro-1H-pyrrolo[3,2-b]pyridin-1-yl]-7H-pyrrolo[2,3-d]pyrimidine;

4-{(3aR,7aR)-4-[(trifluoromethyl)sulfonyl]octahydro-1H-pyrrolo[3,2-b]pyridin-1-yl}-7H-pyrrolo[2,3-d]pyrimidine;

4-[(3aR,7aR)-4-(phenylsulfonyl)octahydro-1H-pyrrolo[3,2-b]pyridin-1-yl]-7H-pyrrolo[2,3-d]pyrimidine; and 4-[(3aR,7aR)-4-(benzylsulfonyl)octahydro-1H-pyrrolo[3,2-b]pyridin-1-yl]-7H-pyrrolo[2,3-d]pyrimidine;

or a pharmaceutically acceptable salt thereof.

The invention also encompasses pharmaceutical compositions containing a compound of formula I, and methods for treatment or prevention of Jak mediated diseases using compounds of formula I.

The invention is described using the following definitions unless otherwise indicated.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

"Aryl" refers to a 6-10 membered monocyclic or bicyclic carbon only ring systems in which at least one ring is aromatic. In a bicyclic system, the point of attachment to the rest of the molecule may be on either ring. Examples of aryl include, but are not limited to, phenyl, tetrahydronaphthyl, indanyl, indennyl, dihydronaphthyl and naphthyl.

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Halogen" or "halo" includes F, Cl, Br, and I.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$haloallyl, for example, includes —$CF_3$, —$CF_2CF_3$, $CHFCH_3$, and the like.

"Heteroaryl" or "heteroaromatic" as used herein represents a 5-10 membered aromatic ring system containing one ring (monocyclic) or two fused rings (bicyclic), and 1-4 heteroatoms independently selected from O, S and N. For a bicyclic heteroaryl only one of the rings need to be hetero aromatic, the second ring may be a heteroaromatic or an aromatic, saturated, or partially unsatuated carbocycle, and the point(s) of attachment to the rest of the molecule may be on either ring. Examples of heteroaryl include, but are not limited to, furanyl, thienyl, pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

"Heterocycle" or "heterocyclic" represents a monocyclic or bicyclic 4-10 membered ring system in which at least one ring is non-aromatic (saturated or partially unsaturated) and containing at least one heteroatom selected from O, S and N.

In a bicyclic ring system, the second ring may be a heteroaryl, heterocycle or a saturated, partially unsaturated or aromatic carbocycle, and the point(s) of attachment to the rest of the molecule may be on either ring. Examples of heterocycle include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl and the like.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —$(CR^8R^9)_2$—, each occurrence of the two $R^8$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of formula I may be separated into their individual diastereoisomers by, e.g., fractional crystallization from suitable solvents, e.g., methylene chloride/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, any stereoisomer of a compound of this invention may be obtained by stereospecific synthesis using optically pure starting materials or reagents of known absolute configuration.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of the general formula I may be obtained by stereospecific synthesis using optically pure starting materials, intermediates or reagents of known configuration. Absolute stereochemistry may be determined by X-ray crystallography of crystalline products or crystalline intermediates which are derivatized, if necessary, with a reagent containing a stereogenic center of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, Ia, Ib, Ic, Id and Ie, subsets thereof, embodiments thereof, as well as specific compounds are meant to also include the pharmaceutically acceptable salts.

Furthermore, some of the crystalline forms for compounds of the present invention may exist as polymorphs and as such all fowls are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compound of formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as Jak1, Jak2 or Jak3. Such conditions and diseases include, but are not limited to:

(1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a Jak-mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a Jak-mediated diseases or disorder.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced fowl, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of Jak mediated diseases, compound of formula I may be co-administered with other therapeutic agents. Thus in another aspect the present invention provides pharmaceutical compositions for treating Jak mediated diseases comprising a therapeutically effective amount of a compound of formula I and one or more other therapeutic agents. In particular, for the treatment of the inflammatory diseases rheumatoid arthritis, psoriasis, inflammatory bowel disease, COPD, asthma and allergic rhinitis a compound of formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-l) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

Methods Of Synthesis

Compounds of formula I of the present invention can be prepared according to the synthetic routes outlined in the following schemes and by following the methods described herein. Abbreviations used herein include: Ac=acetyl; ACN=acetonitrile; HOAc, AcOH acetic acid; BOC, Boc=t-butoxycarbonyl; CAM=ceric ammonium molybdate; Cbz, CBZ=benzyloxycarbonyl; CDI=N,N'-carbonyldiimidazole; DABCO=1,4-diazabicyclo[2.2.2]octane; DBU=1,8-diazabicyclo[5.4.0]undec-7-ene; DCM=dichloromethane; DEPBT=3-(diethoxyphosphoryloxy)-1,2,3-benzotriazin-4 (3H)-one; DIEA, DIPEA=diisopropylethylamine; DMAP=4-dimethylaminopyridine; DMF=dimethylformamide; DMFDMA=dimethylformamide dimethylacetal; DMSO=dimethyl sulfoxide; DSC=disuccinyl carbonate; EI=electron impact; ES=electrospray; Et=ethyl; EtOAc=ethyl acetate; HOBT=1-hydroxybenzotriazole; HPLC=high pressure liquid chromatography; IPA=isopropyl alcohol; iPr=isopropyl; LC=liquid chromatography; LDA=lithium diisopropylamide; LRMS=low resolution mass spectra; Me=methyl; NMP=N-methylpyrrolidone; NPLC normal phase liquid chromatography; n-Pr=n-propyl; Ph=phenyl; RP=reversed-phase; RT, rt=room temperature; SEM=[2-(trimethylsily)ethoxy]methyl; TEA=triethylamine; TFA=trifluoroacetic acid; THF=tetrahydrofuran.

Compounds of formula I of the present invention can be prepared according to the synthetic routes outlined in the following schemes and by following the methods described herein. Starting materials are either commercially available, known in the literature or can be prepared using methodologies generally known in the art.

Scheme 1 depicts the construction of intermediate compounds of formulae 3 and 4. Mono-protected diamine 1 and protected pyrrolopyrimidine 2 are reacted together in the presence of a suitable base such as $Et_3N$ in a solvent such as DMF at or around 90° C. to afford 3 following the removal of the pyrrole nitrogen protecting group. Suitable amine protecting group PG1 is, for example, the CBZ group, and suitable PG2 is, for example, the SEM group. The SEM group may be removed with, for example, TFA in a solvent such as DCM, followed by ammonium hydroxide (or other suitable base) in a solvent such as ACN.

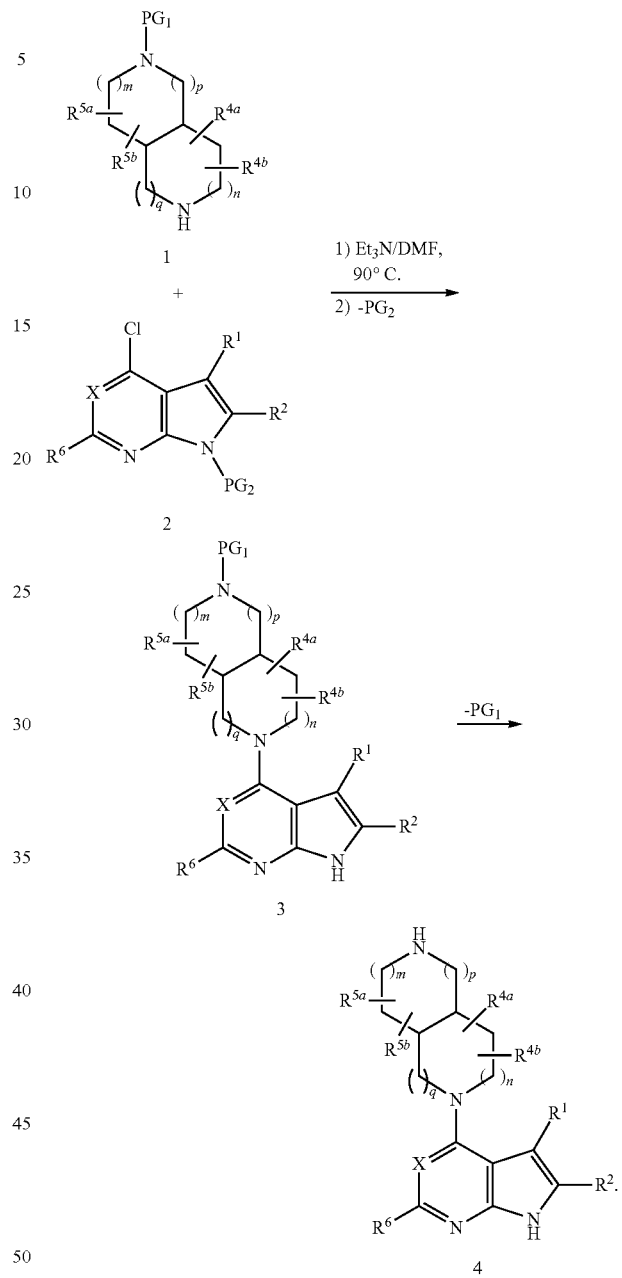

Scheme 2 depicts representative transformations of compound 4 into a compound of formula I. For the preparation of carbamate 5, an appropriately substituted alcohol is reacted with disuccinyl carbonate (DSC), triphosgene, N,N'-carbonyldiimidazole (CDI) or any other suitable activating reagents in the presence of a suitable base such as $Et_3N$ in a solvent such as ACN at ambient temperature to afford the mixed carbonate intermediate, which is then reacted with amine 4 to afford the product (adapted from Hamilton, G., L.; Backes, B. J. *Tetrahedron Lett.* 2006, 47, 967).

Amide 6 can be prepared from amine 4 with an appropriate acylating agent such as an acid chloride in the presence of a suitable base such as DIPEA or TEA in a solvent such as DCM at or around ambient temperature. Alternatively, 6 could be prepared from the corresponding amine 4 and carboxylic acid fragments via an amide coupling using DEBPT or other suitable coupling agent in the presence of TEA or another suitable base in DMF or another suitable solvent at ambient temperature. The α-cyanoacetamide 7 can be prepared by acylating amine 4 with a malonitrile ester and DBU in a suitable solvent such as NMP or 2-methyl-tetrahydrofuran, methanol, tert-butanol or the like at 40° C. (adapted from Price, K. E.; Larrivee-Aboussafy, C.; Lillie, B. M.; McLaughlin, R. W.; Mustakis, J.; Hettenbach, K. W.; Hawkins, J. M.; Vaidyanathan, R. Org. Lett. 2009, 11, 2003). The α-hydroxy-acetamide 8 can be prepared by acylating amine 4 with a 1,3-dioxolan-4-one in toluene/THF at reflux. Alternatively, both 7 and 8 could be prepared from amine 4 using the corresponding acid precursor using a suitable amide coupling reagent such as DEBPT in the presence of TEA or another suitable base in DMF.

The tertiary amine 9 can be prepared from amine 4 by reacting an activated heteroarenes or arenes (e.g., a bromo-heteroarene) in THF or dioxane or other similar solvents in the presence of DBU or another suitable base at 80° C. Amine 10 can be prepared by reacting amine 4 with either an appropriate aldehyde or ketone in a suitable solvent such as THF and in the presence of a suitable reducing agent such as $NaB(OAc)_3H$, or with a suitable electrophile such as benzyl bromide in a suitable solvent such as MeOH with or without a base. The urea 11 can be prepared by reacting amine 4 with a suitable isocyanate which can in turn be prepared from an appropriate amine and triphosgene or by reacting an appropriate amine with a suitable activating agent such as phosgene, CDI, DSC and the like, in a suitable solvent such as DCM, and a suitable base such as DIPEA.

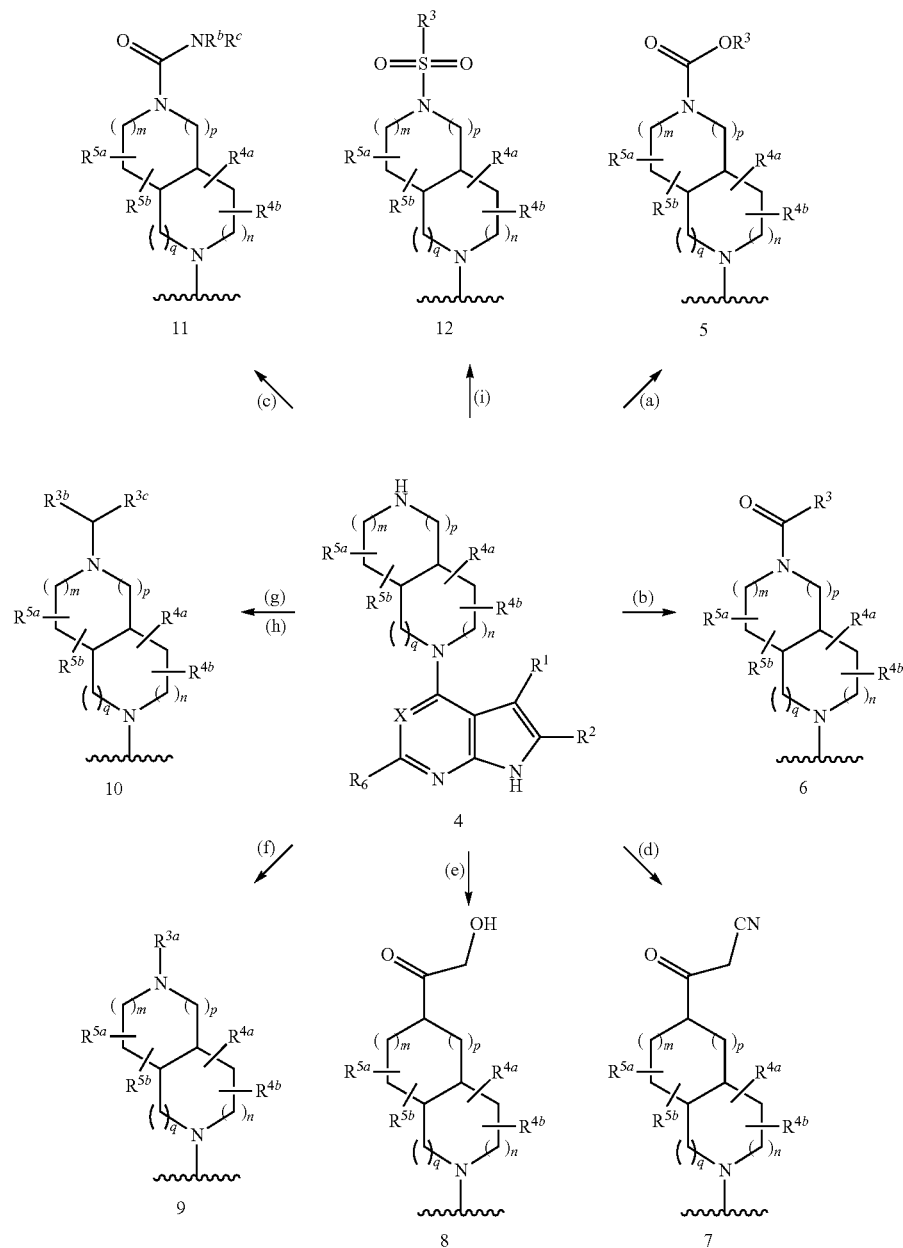

Scheme 2

-continued

R³ᵃ is an aryl or heteroaryl group; the group —CHR³ᵇR³ᶜ is a group within the definition of R³;
X is a suitable leaving group.
(a) i. product from R³OH, DSC or triphosgene or CDI; ii. TEA, ACN; (b) R³C(O)Cl, DIPEA, DCM; or R³CO₂H, DEPBT, TEA, DMF; (c) HNR^bR^c, triphosgene, DIPEA, DCM; (d) NCCH₂C(O)OMe, DBU, 2-MeTHF; or NCCH₂CO₂H, DEPBT, TEA, DMF; (e) 1,3-dioxolan-4-one, toluene/THF, reflux; or HOCH₂CO₂H, DEPBT, TEA, DMF; (f) R³ᵃ-X, DBU, THF/dioxane; (g) R³ᵇC(O)R³ᶜ, THF, NaB(OAc)₃H; (h) XCHR³ᶜR³ᵇ, MeOH, base; (i) ClSO₂R³, DIPEA, DCM.

Scheme 3 describes the synthetic route to access substitution at the 2-position of the pyrrolo-pyrimidine core. Pyrrolo-pyrimidine 13 (where R⁷ is a cleavable directing group such as SEM) is treated with an appropriate strong base such as LDA in a solvent such as THF at or around −78° C., and then subsequently reacted with a suitable electrophile (such as iodomethane) to afford the desired 2-substituted pyrrolo-pyrimidine 14. Subsequent steps are performed in analogy to that described in Schemes 1 and 2.

Scheme 3.

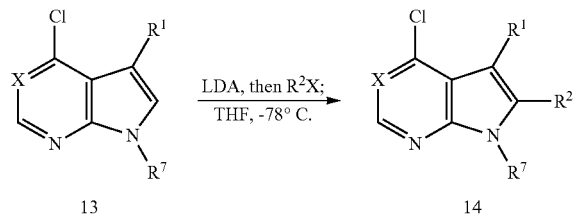

Compounds of formula I can be prepared according to the general procedures described in the Schemes and Examples herein, using appropriate materials. Representative compounds of the present invention are exemplified herein below. The compounds exemplified are not, however, to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature or described herein. Chiral analogs were prepared via incorporation of chiral reagents or obtained after chiral chromatography separation of a racemically generated analog. All temperatures are degrees Celsius unless otherwise noted. Mass spectra (MS) were measured either by electrospray ion-mass spectroscopy (ESMS) or by atmospheric pressure chemical ionization mass spectroscopy (APCI). Jak1 data were obtained using the in vitro assay described below.

Biological Assay

Jak Biochemical HTRF Assay Protocol

The ability of compounds to inhibit the activity of Jak1, Jak2, Jak3, and Tyk2 was measured using a recombinant purified GST-tagged catalytic domain for each enzyme (Invitrogen Jak1 #M4290, Jak2 #M4290, Jak3 #M4290, Tyk2 #M4290) in an HTRF format biochemical assay. The reactions employed a common peptide substrate, LCB-EQEDE-PEGDYFEWLW-NH2 (in-house). The basic assay protocol is as follows: First, 250 mL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 µL, of 1.11X enzyme and 1.11X substrate in 1X assay buffer (Invitrogen kinase buffer #PV3189, 2 mM DTT, 0.05% BSA) were added to the wells and shaken and then preincubated for 30 minutes at room temperature to allow compound binding to equilibrate. After equilibration, 2 µL of 10X ATP in 1X assay buffer was added to initiate the kinase reaction and the plates were shaken and then incubated at room temperature for 120 minutes. At the end of the incubation, 20 µL of 2X stop buffer (streptavidin-Dylight (Thermo #21845), Eu-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision ($\lambda_{ex}$=337 nm, $\lambda_{em}$=665 and 615 nm, TRF delay time=20 µs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate IC₅₀ values.

Final reaction conditions were:

| Enzyme | [E] (nM) | [S] (µM) | [ATP] (µM) | [Eu-pY20] (nM) | [SA-Dylight] (nM) |
|---|---|---|---|---|---|
| Jak1 | 1.405 | 0.75 | 31.8 | 9 | 312.5 |
| Jak2 | 0.052 | 0.75 | 8.5 | 9 | 312.5 |
| Jak3 | 0.031 | 0.75 | 2.9 | 9 | 312.5 |
| Tyk2 | 2.612 | 0.75 | 6.9 | 9 | 312.5 |

Compound concentrations tested were 1481, 494, 173, 49, 19, 6.2, 2.1, 0.74, 0.24, 0.074, and 0.012 nM, with 1.25% residual DMSO. Representative IC₅₀ values obtained using this protocol are 2, 11, 131, 26, 169, 31, 12, 39, 5, 30, 132, 7 and 14 nM for Examples 4, 3-32, 3-41, 12, 13, 16, 20, 23, 29-28, 29-36, 29-49, 32-2 and 32-4 respectively. For all other representative compounds, IC$_{50}$ values are provided as follows: ++++:≤1 nM; +++:>1 nM≤10 nM; ++: >10 nM≤100 nM; +:>100 nM≤1000 nM.

PREPARATION OF INTERMEDIATES

Intermediate 1a.

(3aS,7aS and 3aR,7aR) 4-benzyl 1-tert-butyl hexahydro-1H-pyrrolo[3,2-b]pyridine-1,4(2H)-dicarboxylate

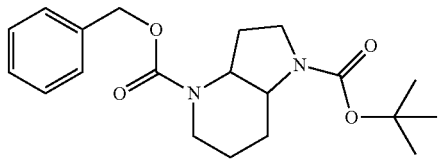 [SMILES: CC(C)(C)OC(=O)N1CCC2C1CCCN2C(=O)OCc1ccccc1]

Step 1: (E)-N N dimethyl-2-(3 nitropyridin-2-yl)ethenamine

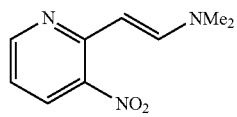

To a dry round-bottom flask purged with nitrogen was added 2-methyl-3-nitropyridine (0.1 kg, 0.7 mol), followed by dimethylformamide-dimethylacetal (1 L). The resulting reaction mixture was heated with stirring to 100-110° C. for approximately 8 hours. The reaction mixture was then cooled to 25-30° C., diluted with toluene (0.3 L), and ice water (0-5° C., 0.05 L) was added to the reaction mixture. The reaction was stirred for approximately 5 minutes and the layers were separated, and the aqueous layer was extracted with additional toluene (0.1 L). The combined organic washings were extracted with water (3×0.05 L). The organic layer was dried over sodium sulfate, filtered and concentrated in vacuo to afford a crude solid. To this solid was added hexanes (0.3 L), and the slurry was stirred for approximately 10 minutes. The solids were isolated by filtration, rinsing the filter cake with additional hexanes to afford the desired product as a red solid. The solids were dried under vacuum at 50-60° C.

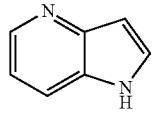

Step 2: 1H-pyrrolo[3,2-b]pyridine

To a dry round-bottom flask was added hydrazine hydrate (0.3 L), the product of Step 1 (0.1 kg, 0.5 mol), followed by water (0.3 L). A solution of FeCl$_3$ (0.01 kg, 0.06 mol) in MeOH (0.3 L) was prepared and added dropwise to the reaction mixture, maintaining the temperature between 25-70° C. The resulting reaction mixture was stirred at a temperature between 65-70° C. for approximately 12-15 hours before being cooled to 50-60° C. MeOH was then removed by distillation at 50-60° C. and the resulting aqueous mixture was cooled to 25-30° C. and extracted with DCM (0.3 L, then again using 0.1 L). The combined organic washings were dried over sodium sulfate, filtered and concentrated in vacuo to afford a crude material. To this crude material was added hexanes (0.3 L) and the slurry was stirred for 30 minutes. The solids were then filtered, rinsing the filter cake with additional hexanes (0.05 L) to afford the desired product after drying under vacuum at 50-60° C. LRMS (EI) calc'd for C$_7$H$_6$N$_2$ [M], 118. found 118. $^1$H NMR (500 MHz, DMSO-D$_6$) δ 11.28 (br s, 1H), 8.28 (d, 1 H), 7.74 (d, 1H), 7.61 (t, 1H), 7.06 (q, 1H), 6.52 (br s, 1H).

Step 3: tert-butyl 1H-pyrrolo[3,2-b]pyridine-1-carboxylate

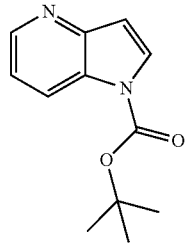 [SMILES: CC(C)(C)OC(=O)n1ccc2ncccc21]

To a stirred solution of the product of Step 2 (1.97 g, 16.7 mmol), and DMAP (2.04 g, 16.7 mmol) in DCM (30 mL) was added TEA (2.33 mL, 16.7 mmol), followed by Boc$_2$O (4.37 g, 20.0 mmol). The reaction mixture was stirred at room temperature for 16 hours. The reaction mixture was concentrated in vacuo, diluted with a minimal amount of DCM and purified directly by column chromatography on silica gel, eluting with EtOAc/hexane (7-60%) to give the desired product as a yellow oil that solidified under high vacuum. LRMS (ESI) calc'd for C$_{12}$H$_{15}$N$_2$O$_2$ [M+H]$^+$, 219; found 219. $^1$H NMR (500 MHz, DMSO-D$_6$) δ 8.47 (d, 1H), 8.29 (d, 1H), 7.97 (d, 1H), 7.32 (q, 1H), 6.82 (d, 1H), 1.62 (s, 9H).

Step 4: (3aS,7aS and 3aR,7aR) tert-butyl octahydro-1H-pyrrolo[3,2-b]pyridine-1-carboxylate (HOAc salt)

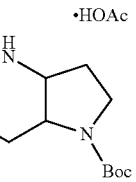

The product of Step 3 (2.66 g, 12.2 mmol) was added to a Parr shaker pressure vessel that was subsequently purged with nitrogen. Platinum (IV) oxide (0.277 g, 1.22 mmol) was added, followed by AcOH (27 mL). The vessel was placed on a Parr shaker apparatus and was sealed and evacuated and refilled with nitrogen 4 times (with shaking in between cycles). The vessel was then evacuated and refilled with hydrogen 4 times (with shaking in between cycles). The reaction was shaken under hydrogen pressure (approximately 60 psi; the vessel was recharged up to 60 psi as needed) for 48 hours. An additional amount of platinum (IV) oxide (0.277 g, 1.22 mmol) was added in order to drive the reaction to completion. After 24 hours, the reaction mixture was diluted with EtOAc (50 mL) and filtered through a Celite cartridge (Celite 545 Isolute®SPE column; Biotage, Inc.), rinsing the filter cake with additional EtOAc. The filtrate was concentrated in vacuo to a crude oil which was azeotroped with heptane several times until a constant weight was achieved, affording the desired product (HOAc salt). LRMS calc'd for $C_{12}H_{23}N_2O_2$ $[M+H]^+$, 227; found 227.

Step 5: (3aS-7aS and 3aR,7aR) 4-benzyl 1-tert-butyl hexahydro-1H-pyrrolo[3,2-b]pyridine-1,4(2H)-dicarboxylate The product of Step 4 (HOAc salt; 3.49 g, 12.2 mmol) was added to a flask, followed by THF (55 mL). Aqueous sodium carbonate (2M; 30.5 mL, 60.9 mmol) was added, and the resulting biphasic mixture was cooled to 0° C. Benzyl chloroformate (2.61 mL, 18.3 mmol) was added and the reaction mixture was allowed to stir while the bath naturally warmed to ambient temperature. After 30 minutes the reaction mixture was partitioned between EtOAc and water (100 mL each) and the layers were separated. The organic layer was then dried over sodium sulfate, filtered, and concentrated in vacuo to a crude oil that was purified by column chromatography on silica gel eluting with EtOAc/hexane (5-30%) (TLC was visualized with CAM staining) to afford the title product as a colorless oil. LRMS calc'd for $C_{20}H_{28}N_2O_4Na$ $[M+Na]^+$, 383; found 383. $^1H$ NMR (500 MHz, $CDCl_3$) δ 7.39-7.30 (br m, 5H), 5.15 (br s, 2H), 4.70-4.45 (br m, 1H), 4.15-3.95 (br m, 1H), 3.82-3.62 (br d, 1H), 3.50-3.21 (br m, 2H), 2.79 (br pentet, 1H), 2.30-1.90 (br m, 3H), 1.72-1.58 (br m, 1H), 1.45 (s, 9H), 1.40 (br m, 1H), 1.28-1.14 (br m, 1H).

Intermediate 2a.

4-chloro-7-{[2-(trimethylsilyl)ethoxy]methyl}-7H-pyrrolo[2,3-d]pyrimidine

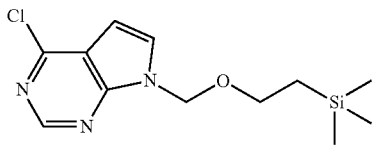 [SMILES: C[Si](C)(C)CCOCn1ccc2c(Cl)ncnc21]

To a stirred suspension of 4-chloro-7H-pyrrolo[2,3-d]pyrimidine (3.00 g, 19.5 mmol) in DMF (45 mL) was added SEM-Cl (5.20 mL, 29.3 mmol). The resulting mixture was placed under nitrogen and cooled to 0° C. in an ice bath. NaH (0.938 g of a 60% dispersion in mineral oil, 23.4 mmol) was added, the resulting yellow suspension was stirred at 0° C. for approximately 1 hour. The reaction was quenched with 10% aqueous NaCl (180 mL), and the resulting mixture was extracted with EtOAc (180 mL). The organic washings were washed with additional 10% aqueous NaCl (180 mL), dried over sodium sulfate, filtered, and concentrated in vacuo to a crude oil. The oil was purified by column chromatography on silica gel eluting with EtOAc/hexane (2-20%) to afford the title compound as an oil. LRMS calc'd for $C_{12}H_{19}ClN_3OSi$ $[M+H]^+$, 284; found 284. $^1H$ NMR (500 MHz, $CDCl_3$) δ 8.67 (s, 1H), 7.39 (d, 1H), 6.67 (d, 1H), 5.65 (s, 2H), 3.52 (t, 2H), 0.91 (t, 2H), 0.06 (s, 9H).

Example 1

(3aS,7aS and 3aR,7aR) benzyl 1-(7H-pyrrolo[2,3-d]pyrimidin-4-yl)octahydro-4H-pyrrolo[3,2-b]-pyridine-4-carboxylate

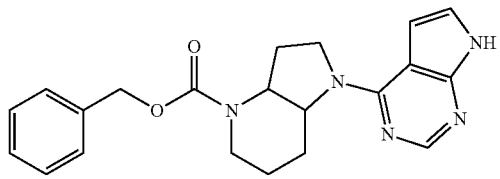 [SMILES: O=C(OCc1ccccc1)N1CCCC2C1CCN2c1ncnc2[nH]ccc12]

Step 1: (3aS,7aS and 3aR,7aR) benzyl octahydro-4H-pyrrolo[3,2-b]pyridine-4-carboxylate

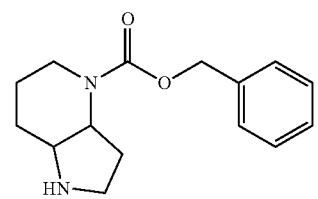 [SMILES: O=C(OCc1ccccc1)N1CCCC2NCCC21]

To a stirred solution of Intermediate 1a (2.38 g, 6.60 mmol) in DCM (24 mL) was added TFA (24 mL). The resulting solution was stirred at ambient temperature for 30 minutes. The reaction mixture was concentrated in vacuo to a crude oil that was then taken up into DCM and concentrated several times until a constant weight was achieved. This oil was dissolved in DCM (100 mL), then treated with 7.5% aqueous sodium bicarbonate (200 mL). The layers were separated, then the aqueous layer was extracted with 5% MeOH/DCM (3×100 mL). The combined organic washings were dried over sodium sulfate, filtered and concentrated in vacuo to afford the desired product as a crude oil. LRMS calc'd for $C_{15}H_{21}N_2O_2$ $[M+H]^+$, 261; found 261. $^1H$ NMR (500 MHz, $CDCl_3$) δ 7.38-7.30 (m, 5H), 5.14 (AB quartet, 2H), 4.58 (br q, 1H), 4.02 (br d, 1H), 3.18 (m, 2H), 3.06 (m, 1H), 2.80 (br t, 1H), 2.10-1.97 (br m, 1H), 1.73-1.66 (br m, 1H), 1.46-1.32 (br m, 2H).

Step 2: (3aS,7aS and 3aR,7aR) benzyl 1-(7-{[2-(trimethylsilyl)ethoxy]methyl}-7H-pyrrolo[2,3-d]pyrimidin-4-yl)octahydro-4H-pyrrolo[3,2-b]pyridine-4-carboxylate

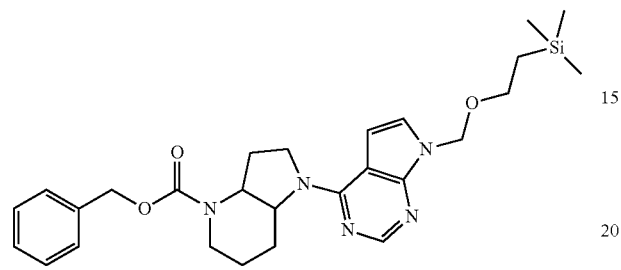

To a stirred solution of the product of Step 1 (1.72 g, 6.60 mmol) and Intermediate 2a (1.87 g, 6.60 mmol) in DMF (44 mL) was added TEA (2.76 mL, 19.8 mmol). The resulting solution was stirred at 90° C. for 6 hours, then cooled to ambient. The reaction mixture was partitioned between EtOAc (100 mL) and 10% aqueous sodium chloride (100 mL). The layers were separated, and the organic layer was washed with additional 10% aqueous sodium chloride (100 mL). The first aqueous layer was extracted with EtOAc (200 mL). The combined organic washings were dried over sodium sulfate, filtered, and silica gel was added to the filtrate. The resulting mixture was concentrated in vacuo to afford a crude solid that was purified by column chromatography on silica gel eluting with EtOAc/hexane (12-100%) to afford the desired product as a yellow foam. LRMS calc'd for $C_{27}H_{38}N_5O_3Si$ [M+H]$^+$, 508; found 508.

Step 3: (3aS,7aS and 3aR,7aR)benzyl 1-(7H-pyrrolo[2,3-d]pyrimidin-4-yl)octahydro-4H-pyrrolo[3,2-b]pyridine-4-carboxylate To a stirred solution of the product of Step 2 (2.77 g, 5.46 mmol) in DCM (28 mL) was added TFA (28 mL). The resulting solution was stirred for 1 hour at room temperature. Heptanes were then added, and the mixture was concentrated in vacuo, azeotroping with DCM and heptanes until a constant weight was achieved. The resulting oil was taken up into acetonitrile (28 mL), and ammonium hydroxide (28 mL) was added. The solution was stirred at ambient temperature for approximately 5 minutes, then the reaction mixture was scratched with a glass pipette in order to promote crystallization. The reaction mixture was stirred for approximately 19 hours before being heated at 50° C. for 1 hour. The reaction mixture was cooled, and diluted with water (28 mL). The solids were filtered and the filter cake was rinsed with water and dried under high vacuum until constant weight was achieved to afford the desired product as an off-white solid. LRMS calc'd for $C_{21}H_{24}N_5O_2$ [M+H]$^+$, 378; found 378. $^1$H NMR (500 MHz, DMSO-D$_6$) δ 11.6 (s, 1H), 8.06 (s, 1H), 7.40-7.28 (br m, 5H), 7.10 (s, 1H), 6.52 (s, 1H), 5.13-5.07 (m, 2H), 4.61 (br s, 1H), 4.32 (br s, 1H), 3.98-3.64 (br m, 3H), 2.98-2.80 (m, 1H), 2.36-2.12 (br m, 2H), 2.04 (br m, 1H), 1.64 (br m, 1H), 1.50-1.22 (br m, 2H). Jak1 activity: ++.

The product of Step 2 was separated into the two enantiomers using preparative HPLC: ChiralPak IA 50×250 mm column with 70:30 hexanes:ethanol mobile phase, 80 mL/min; retention times=19.2 minutes (95% ee enantiomer A) and 22.9 minutes (90% ee -enantiomer B). These separated enantiomers were then deprotected according to Step 3 above to provide two individual enantiomers of the title product. Enantiomer A Jak1 activity: +; Enantiomer B Jak1 activity: +++.

Example 2

(3aS,7aS) 4-(octahydro-1H-pyrrolo[3,2-b]pyridin-1-yl)-7H-pyrrolo[2,3-d]pyrimidine (enantiomer 1) and (3aR,7aR) 4-(octahydro-1H-pyrrolo[3,2-b]pyridin-1-yl)-7H-pyrrolo[2,3-d]pyrimidine (enantiomer 2)

enantiomer 1

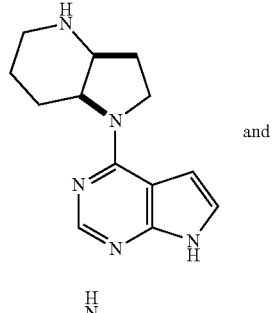

and enantiomer 2

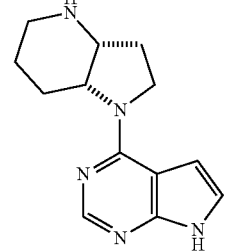

Step 1: (3aS,7aS and 3aR,7aR) 4-(octahydro-1H-pyrrolo[3,2-b]pyridin-1-yl)-7H-pyrrolo[2,3-d]pyrimidine HBr salt

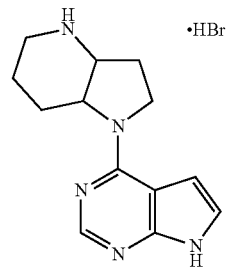 [SMILES: c1nc(N2CCC3NCCCC32)c2cc[nH]c2n1 ; Br]

A suspension of the racemic product of Example 1 (1.77 g, 4.69 mmol) in 33% HBr in acetic acid (30 mL) was stirred at ambient temperature for 2 hours. The reaction mixture was concentrated to a crude solid/liquid mixture. Ethanol (35 mL) was added, and the resulting suspension was stirred at ambient temperature. The solids were filtered, rinsing the filter cake with ethanol. The filtered solids were dried on the high vacuum until constant weight was achieved to afford the desired product (HBr salt) as a grey solid. LRMS calc'd for $C_{13}H_{18}N_5[M+H]^+$, 244; found 244. $^1H$ NMR (500 MHz, DMSO-$D_6$) δ 12.7 (br s, 1H), 9.21 (br s, 2H), 8.35 (s, 1H), 7.47 (s, 1H), 6.85 (s, 1H), 4.56 (br s, 1H), 4.30-3.76 (br m, 4H), 3.20-3.02 (br m, 2H), 2.60 (br pentet, 1H), 2.33-2.24 (br m, 1H), 2.22-2.14 (br m, 1H), 1.82-1.74 (br m, 1H), 1.74-1.52 (br m, 2H).

Step 2: 4-(octahydro-1H-pyrrolo[3,2-b]pyridin-1-yl)-7H-pyrrolo[2,3-d]pyrimidine (both enantiomers)

To the product of Step 1 (7.56 g, 18.7 mmol) was added water (100 mL). The solution was then sonicated and gently warmed to ensure complete dissolution of the starting material. To the light brown solution was added Biotage MP-carbonate resin (30 g, 3.34 mmol/g). The solution was swirled gently for 16 hours before being filtered through a thin pad of Celite which was rinsed with acetonitrile and water successively. The filtrate was concentrated in vacuo, azeotroped with toluene (twice), then azeotroped with methanol (twice). The resulting light brown solid was dissolved in methanol (40 mL) and separated by preparative SFC using a ChiralPak IA column (50×250 mm) with 35% modifier solution comprised of methanol with 0.2% diethylamine at 250 mL/min (enantiomer retention times=3.4 minutes {enantiomer 1} & 4.7 minutes {enantiomer 2}). Concentration of the separated enantiomer solutions gave 98.2% ee material for enantiomer 1 (retention time=3.4 minutes) and 94.6% ee for enantiomer 2 (retention time=4.7 minutes). LRMS calc'd for $C_{13}H_{18}N_5$ $[M+H]^+$, 244; found 244. $^1H$ NMR (500 MHz, $CD_3OD$) δ 8.05 (s, 1H), 7.06 (d, J=3.6Hz, 1H), 6.58 (d, J=3.5 Hz, 1H), 4.27 (m, 1H), 3.96 (m, 1H), 3.80 (m, 1H), 3.56 (m, 1H), 2.82-2.73 (m, 2H), 2.36 (m, 1H), 2.25 (m, 1H), 2.00 (m, 1H), 1.63-1.46 (m, 3H). Enantiomer 1 Jak1 activity: +; Enantiomer 2 Jak1 activity: +.

Example 3

Example 3-1: (3aS,7aS and 3aR,7aR) pyridin-3-ylmethyl 1-(7H-pyrrolo[2,3-d]pyrimidin-4-yl)octahydro-4H-pyrrolo[3,2-b]pyridine-4-carboxylate

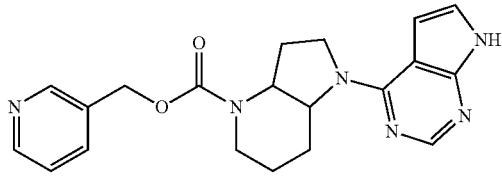 [SMILES: O=C(OCc1cccnc1)N1CCCC2C1CCN2c1ncnc2[nH]ccc12]

To a stirred solution of pyridin-3-ylmethanol (22 mg, 0.20 mmol) in acetonitrile (1 mL) was added TEA (0.028 mL, 0.20 mmol), followed by N,N'-disuccimidinyl carbonate (51 mg, 0.20 mmol). The resulting suspension was stirred at room temperature for 1.5 hours. In a separate vial, a stirred suspension of the product of Example 2, Step 1 (40 mg, 0.099 mmol) in DMSO (0.3 mL) was treated with TEA (0.041 mL, 0.30 mmol). The resulting solution was added to the solution of activated alcohol and it was stirred at ambient temperature for 30 minutes. A suspension fowled, which was diluted with water (1 mL). The suspension was filtered and the filter cake rinsed with water and dried under high vacuum until constant weight was achieved to afford the title product as an off-white solid. LRMS calc'd for $C_{20}H_{23}N_6O_2$ $[M+H]^+$, 379; found 379. $^1H$ NMR (500 MHz, DMSO-$D_6$) δ 11.6 (s, 1H), 8.60 (s, 1H), 8.51 (br m, 1H), 8.06 (s, 1H), 7.81 (br d, 1H), 7.39 (br s, 1H), 7.10 (s, 1H), 6.51 (br s, 1H), 5.14 (m, 2H), 4.60 (br s, 1H), 4.32 (br s, 1H), 4.00-3.62 (br m, 3H), 2.98-2.80 (br m, 1H), 2.40-2.12 (br s, 2H), 2.04 (br s, 1H), 1.64 (br t, 1H), 1.52-1.24 (br m, 2H). Jak1 activity: ++.

The following compounds below in Table 1 were prepared in analogy to the preparation of Example 3-1, by substituting pyridin-3-ylmethanol with the appropriately functionalized alcohol (between 1.35-2.00 equivalents of alcohol relative to the amine) and utilizing 1 equivalent of the N,N'-disuccimidinyl carbonate relative to the alcohol. Additionally, the 4-[(3aR,7aR)-octahydro-1H-pyrrolo[3,2-b]pyridin-1-yl]-7H-pyrrolo[2,3-d]pyrimidine enantiomer (enantiomer 2 as noted above in Example 2, Step 2) was used in place of its racemic HBr salt in instances denoted as "single enantiomer". It is to be understood that the term "single enantiomer" throughout, unless specifically noted to be otherwise, means the product is comprised of the desired enantiomer in enantiomeric excess of 90% or higher. DMSO/acetonitrile was typically used in examples where amine salts were employed in the reaction (as outlined above for 3-1), while only acetonitrile was required when the free amine base was used. Isolation of the final compounds were carried out either by direct filtration or by mass-triggered reverse-phase HPLC using a Waters X-bridge Prep C18 column (5 micron, 19×100 mm), eluting with an ACN/water gradient (with either 0.1% $NH_4OH$ as a basic modifier or 0.1% TFA as an acidic modifier).

TABLE 1

| Compound # | R³ | Exact Mass [M + H]+ | Jak1 Activity |
|---|---|---|---|
| 3-2 | (4-fluorobenzyl) racemate | Calc'd 396, found 396 | ++ |
| 3-3 | n-butyl racemate | Calc'd 344, found 344 | ++ |
| 3-4 | (3-methoxybenzyl) racemate | Calc'd 408, found 408 | ++ |
| 3-5 | (3-(pyridin-3-yl)propyl) racemate | Calc'd 407, found 407 | ++ |

TABLE 1-continued

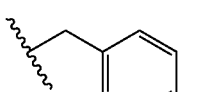

| Compound # | R³ | Exact Mass [M + H]+ | Jak1 Activity |
|---|---|---|---|
| 3-6 | 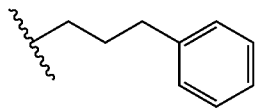 4-chlorobenzyl, racemate | Calc'd 412, found 412 | ++ |
| 3-7 | 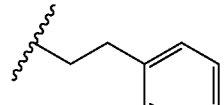 3-phenylpropyl, racemate | Calc'd 406, found 406 | ++ |
| 3-8 | 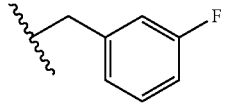 2-phenylethyl, racemate | Calc'd 392, found 392 | ++ |
| 3-9 | 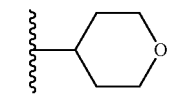 3-fluorobenzyl, racemate | Calc'd 396, found 396 | ++ |
| 3-10 | 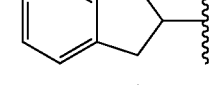 tetrahydropyran-4-yl, racemate | Calc'd 372, found 372 | ++ |
| 3-11 | 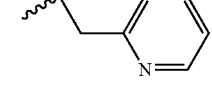 indan-2-yl, racemate | Calc'd 404, found 404 | ++ |
| 3-12 | 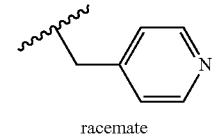 pyridin-2-ylmethyl, racemate | Calc'd 379, found 379 | ++ |
| 3-13 | 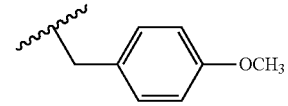 pyridin-4-ylmethyl, racemate | Calc'd 379, found 379 | ++ |

TABLE 1-continued

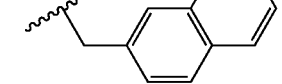

| Compound # | R³ | Exact Mass [M + H]+ | Jak1 Activity |
|---|---|---|---|
| 3-14 | 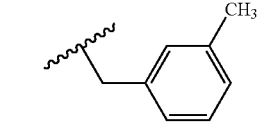 4-methoxybenzyl, racemate | Calc'd 408, found 408 | +++ |
| 3-15 | 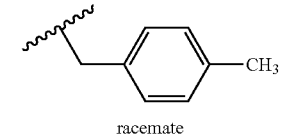 [SMILES: *Cc1ccc(C)cc1] naphthalen-2-ylmethyl, racemate | Calc'd 428, found 428 | ++ |
| 3-16 | 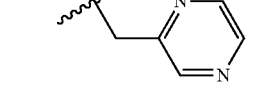 3-methylbenzyl, racemate | Calc'd 392, found 392 | ++ |
| 3-17 | 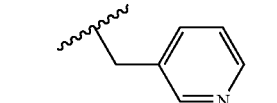 4-methylbenzyl, racemate | Calc'd 392, found 392 | ++ |
| 3-18 | 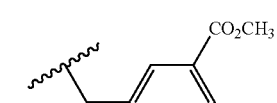 pyrazin-2-ylmethyl, racemate | Calc'd 380, found 380 | ++ |
| 3-19 | 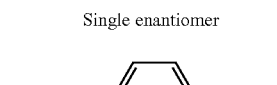 pyridin-3-ylmethyl, Single enantiomer | Calc'd 379, found 379 | + |
| 3-20 | methyl 3-(...)methylbenzoate, Single enantiomer | Calc'd 436, found 436 | + |
| 3-21 | methyl 4-(...)ethylbenzoate, Single enantiomer | Calc'd 450, found 450 | ++ |

TABLE 1-continued

Structure (shared for compounds 3-22 through 3-38): R³-O-C(=O)-N-[octahydropyrrolopyridine core]-N-[pyrrolo[2,3-d]pyrimidine]

| Compound # | R³ | Exact Mass [M + H]+ | Jak1 Activity |
|---|---|---|---|
| 3-22 | -CH₂CH₂CH₂-(4-CO₂CH₃-phenyl); Single enantiomer | Calc'd 464, found 464 | ++ |
| 3-23 | -CH(CH₃)-phenyl (wedge down); Mixture of diastereomers (racemic core material used) | Calc'd 392, found 392 | ++ |
| 3-24 | -CH(CH₃)-phenyl (wedge up); Mixture of diastereomers (racemic core material used) | Calc'd 392, found 392 | ++ |
| 3-25 | -CH₂-(4-CO₂CH₃-phenyl); racemate | Calc'd 436, found 436 | +++ |
| 3-26 | -CH₂-(3-CO₂CH₃-phenyl); racemate | Calc'd 422, found 422 | ++ |
| 3-27 | -CH₂CH₂-N(thiomorpholine-1,1-dioxide); Single enantiomer | Calc'd 449, found 449 | + |
| 3-28 | -CH₂-(2,3-dihydrobenzofuran-5-yl); Single enantiomer | Calc'd 434, found 434 | ++ |
| 3-29 | -CH₂CH₂-cyclopropyl-CO₂CH₃; Mixture of diastereomers (racemic cis/trans alcohol used) | Calc'd 414, found 414 | ++ |
| 3-30 | —CH₂CH₂F; Single enantiomer | Calc'd 334, found 334 | ++ |
| 3-31 | -CH₂-cyclopropyl; Single enantiomer | Calc'd 342, found 342 | ++ |
| 3-32 | -cyclohexyl; Single enantiomer | Calc'd 370, found 370 | ++ |
| 3-33 | -CH₂-(2-F-phenyl); Single enantiomer | Calc'd 396, found 396 | +++ |
| 3-34 | -CH₂-(naphthalen-1-yl); Single enantiomer | Calc'd 442, found 442 | + |
| 3-35 | —CH₂CH₂OCH₃; Single enantiomer | Calc'd 346, found 346 | ++ |
| 3-36 | -CH₂CH₂-N(2-oxopyrrolidin-1-yl); Single enantiomer | Calc'd 399, found 399 | + |
| 3-37 | -CH₂CH₂-(pyridin-2-yl); Single enantiomer | Calc'd 393, found 393 | ++ |
| 3-38 | —CH₂CH₂N(CH₃)₂; Single enantiomer | Calc'd 359, found 359 | + |

TABLE 1-continued

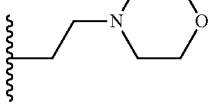

| Compound # | R³ | Exact Mass [M + H]+ | Jak1 Activity |
|---|---|---|---|
| 3-39 | (morpholinopropyl); Single enantiomer | Calc'd 401, found 401 | ++ |
| 3-40 | (pyrrolidinopropyl); Single enantiomer | Calc'd 385, found 385 | + |
| 3-41 | (4-methylpiperazinyl-propyl); Single enantiomer | Calc'd 414, found 414 | + |
| 3-42 | (1-methylpiperidin-4-ylmethyl); Single enantiomer | Calc'd 399, found 399 | + |
| 3-43 | —CH₂CH₂OCH₂CF₃; Single enantiomer | Calc'd 414, found 414 | ++ |
| 3-44 | (3,5-difluorophenethyl); Single enantiomer | Calc'd 428, found 428 | ++ |
| 3-45 | (indol-1-ylethyl); Single enantiomer | Calc'd 431, found 431 | ++ |
| 3-46 | (cyclohexylmethyl); Single enantiomer | Calc'd 384, found 384 | ++ |
| 3-47 | (3-phenylpropyl); Single enantiomer | Calc'd 406, found 406 | +++ |
| 3-48 | (3-(pyridin-3-yl)propyl); Single enantiomer | Calc'd 407, found 407 | ++ |

Example 4

4-(methoxycarbonyl)benzyl (3aR,7aR)-1-(7H-pyrrolo[2,3-d]pyrimidin-4-yl)octahydro-4H-pyrrolo[3,2-b]pyridine-4-carboxylate (TFA salt)

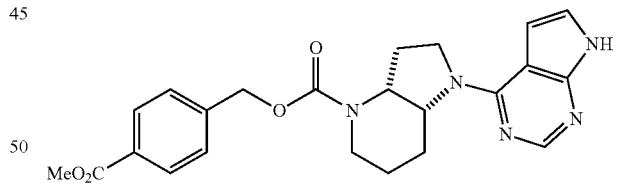

To a stirred solution of methyl 4-(hydroxymethyl)benzoate (10 mg, 0.062 mmol) in DCM (0.19 mL) was added DIPEA (0.022 mL, 0.12 mmol), followed by triphosgene (5.5 mg, 0.018 mmol) at 0° C. The resulting suspension was stirred for 2.5 hours at 0° C., and then enantiomer 2 of Example 2 (15 mg, 0.062 mmol) was added. The resulting reaction mixture was stirred for 18 hours at ambient temperature. The reaction mixture was concentrated in vacuo, dissolved in DMSO (2.0 mL) and purified by mass triggered reverse phase HPLC. Lyophilization of the desired fractions afforded the title product (TFA salt) as a white solid. LRMS calc'd for $C_{23}H_{26}N_5O_4$ [M+H]$^+$, 436; found 436. Jak1 activity: +++.

Example 5

4-(methoxycarbonyl)benzyl (3aS,7aS)-1-(7H-pyrrolo[2,3-d]pyrimidin-4-yl)octahydro-4H pyrrolo[3,2-b]pyridine-4-carboxylate (TFA salt)

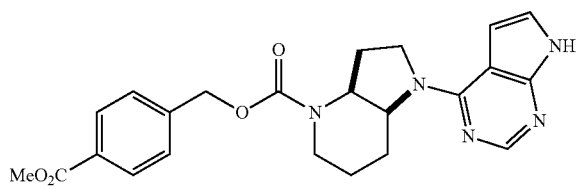

To a stirred solution of methyl 4-(hydroxymethyl)benzoate (41 mg, 0.25 mmol) in DCM (0.62 mL) was added DIPEA (0.072 mL, 0.41 mmol), followed by triphosgene (18 mg, 0.062 mmol) at 0° C. The resulting suspension was stirred for 2.5 hours at 0° C., and then enantiomer 1 of Example 2 (50 mg, 0.21 mmol) was added. The resulting reaction mixture was stirred for 3 hours at ambient temperature. The reaction mixture was partitioned between EtOAc (50 mL) and saturated sodium bicarbonate (50 mL). The layers were separated, and the organic layer was collected, dried over sodium sulfate, and concentrated in vacuo to afford a crude oil that was purified by reverse phase HPLC. Lyophilization of the product fractions afforded the title product (TFA salt) as a white solid. LRMS calc'd for $C_{23}H_{26}N_5O_4$ [M+M]$^+$, 436; found 436. Jak1 activity: +.

Example 6

4-[({[(3aR,7aR)-1-(7H-pyrrolo[2,3-d]pyrimidin-4-yl)octahydro-4H-pyrrolo[3,2-b]pyridine-4-yl]carbonyl}oxy)methyl]benzoic acid (TFA salt)

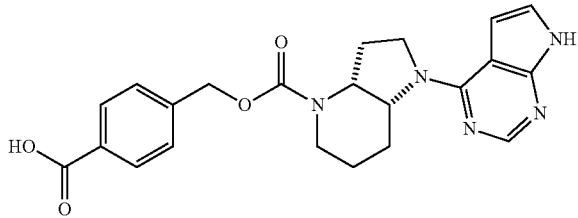

Step 1: 4-(methoxycarbonyl)benzyl (3aR,7aR)-1-(7H-pyrrolo[2,3-d]pyrimidin-4-yl)octahydro-4H-pyrrolo[3,2-b]pyridine-4-carboxylate

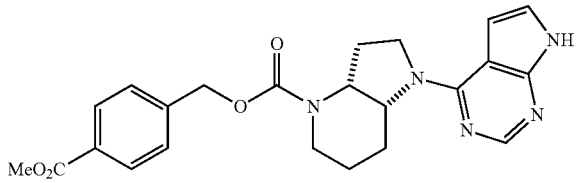

To a stirred solution of methyl 4-(hydroxymethyl)benzoate (68.3 mg, 0.411 mmol) in DCM (1.25 mL) was added DIPEA (0.144 mL, 0.822 mmol), followed by triphosgene (36.6 mg, 0.123 mmol) at 0° C. The resulting suspension was stirred for 2.5 hours at 0° C., then enantiomer 2 of Example 2 (100 mg, 0.411 mmol) was added. The resulting reaction mixture was stirred for 3 hours at ambient temperature. The reaction mixture was partitioned between EtOAc (50 mL) and saturated sodium bicarbonate (50 mL). The layers were separated, and the organic layer was collected, dried over sodium sulfate and concentrated in vacuo to afford a crude oil. The crude oil was purified by column chromatography on silica gel eluting with EtOAc/hexane (0-100%) followed by DCM:MeOH:Et$_3$N (88:10:2). The product fractions were concentrated in vacuo to afford the desired product as a yellow oil. LRMS calc'd for $C_{23}H_{26}N_5O_4$ [M+H]$^+$, 436; found 436.

Step 2: 4-[({[3aR,7aR)-1-(7H-pyrrolo[2,3-d]pyrimidin-4-yl)octahydro-4H-pyrrolo[3,2-b]-pyridine-4-yl]carbonyl}oxy)methyl]benzoic acid (TFA salt)

To a stirred solution of the product of Step 1 (11 mg, 0.025 mmol) in MeOH (0.13 mL) was added 0.5 M aqueous LiOH (0.51 mL, 0.25 mmol) and the reaction mixture was stirred for 48 hours at ambient temperature. The reaction mixture was concentrated in vacuo and purified by mass triggered reverse phase HPLC. Lyophilization of the desired fractions afforded the title product (TFA salt) as a white solid. LRMS calc'd for $C_{22}H_{24}N_5O_4$ [M+H]$^+$, 422; found 422. Jak1 activity: +.

Example 7-1

4-(dimethylcarbamoyl)benzyl (3aR,7aR)-1-(7H-pyrrolo[2,3-d]pyrimidin-4-yl)octahydro-4H-pyrrolo[3,2-b]pyrindine-4-carboxylate (TFA salt)

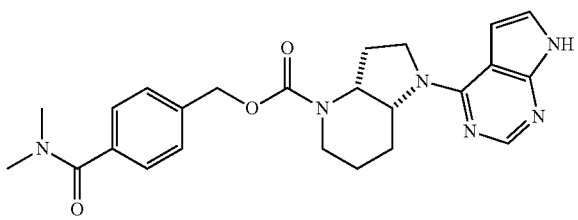

To the product from Example 6, (4-[({[(3aR,7aR)-1-(7H-pyrrolo[2,3-d]pyrimidin-4-yl)octahydro-4H-pyrrolo[3,2-b]pyridine-4-yl]carbonyl}oxy)methyl]benzoic acid), in DMF (0.42 mL) was added DIPEA (0.073 mL, 0.42 mmol), HATU (34 mg, 0.10 mmol) followed by dimethylamine (7.5 mg, 0.17 mmol). The resulting suspension was allowed to stir for 3 hours at ambient temperature and was then concentrated in vacuo, dissolved in DMSO (2.0 mL) and purified by reverse phase HPLC. Lyophilization of the desired fractions afforded the title compound (TFA salt) as a white solid. LRMS calc'd for $C_{24}H_{28}N_6O_3$ [M+H]+, 449; found 449. Jak1 activity: +.

The following examples in Table 2 were prepared in analogy to the preparation of Example 7-1 above, by substituting dimethylamine with the appropriately functionalized amines. The compounds were isolated by mass-triggered reverse-phase HPLC using a Waters X-bridge Prep C18 column (5 micron, 19×100 mm), eluting with an ACN/water gradient (using 0.1% trifluoroacetic acid as modifier).

TABLE 2

| Compound # | R3 | Exact Mass [M + H]+ | JAK1 Activity |
|---|---|---|---|
| 7-2 | H₂N— | Calc'd 421, found 421 | ++ |
| 7-3 | MeHN— | Calc'd 435, found 435 | + |
| 7-4 | Me₂N-CH₂CH₂-NH— | Calc'd 492, found 492 | + |
| 7-5 | Me₂N-CH₂CH₂-NMe— | Calc'd 506, found 506 | + |

Example 8-1

4-{[(tert-butoxycarbonyl)amino]methyl}benzyl(3aR,7aR)-1-(7H-pyrrolo[2,3-d]pyrimidin-4-yl)octahydro-4-pyrrolo[3,2-b]pyridine-4-carboxylate

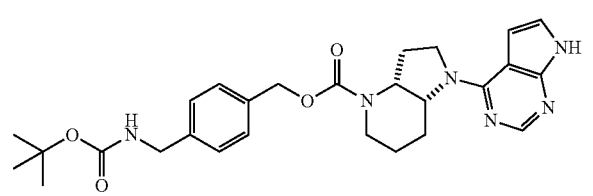

To a stirred solution of CDI (20 mg, 0.12 mmol) in THF (0.20 mL) was added (4-hydroxymethyl-benzyl)-carbamic acid tert-butyl ester (29 mg, 0.12 mmol) in THF (0.20 mL) at −10° C. The resulting suspension was allowed to stir for 1 hour at ambient temperature. In a separate flask, enantiomer 2 of Example 2 was dissolved in THF (0.20 mL) and DBU (0.019 mL, 0.12 mmol) followed by Et₃N (0.017 mL, 0.12 mmol) was added and allowed to stir at ambient temperature for 5 minutes. The activated alcohol solution was added to the suspension of amine in DBU and the resulting suspension was allowed to stir at ambient temperature for 18 hours. The reaction mixture was partitioned between EtOAc (25 mL) and saturated aqueous sodium bicarbonate (25 mL). The layers were separated, and the organic layer was collected, dried over sodium sulfate, and concentrated in vacuo. The crude reaction mixture was purified by column chromatography on silica gel eluting with EtOAc/hexane (0-100%) followed by DCM:MeOH (90:10). The product fractions were concentrated in vacuo to afford the desired product. LRMS calc'd for $C_{27}H_{34}N_6O_4$ [M+H]+, 507; found 507. Jak1 activity: +.

The following compounds below in Table 3 were prepared in analogy to the preparation of Example 8-1 above, by substituting (4-hydroxymethyl-benzyl)-carbamic acid tert-butyl ester with the appropriately functionalized alcohols. The compounds were isolated by mass-triggered reverse-phase HPLC using a Waters X-bridge Prep C18 column (5 micron, 19×100 mm), eluting with an ACN/water gradient (using 0.1% trifluoroacetic acid as modifier).

TABLE 3

| Compound # | R³ | Exact Mass [M + H]+ | JAK1 Activity |
|---|---|---|---|
| 8-2 | (1-phenylethyl), Single enantiomer | Calc'd 392, found 392 | ++ |
| 8-3 | morpholinyl-CH₂CH₂-CH(Ph)—, Mixture of diastereomers (racemic alcohol used) | Calc'd 491, found 491 | + |

Example 9

4-(aminomethyl)benzyl (3aR,7aR)-1-(7H-pyrrolo[2,3-d]pyrimidin-4-yl)octahydro-4H-pyrrolo[3,2-b]pyridine-4-carboxylate (TFA salt)

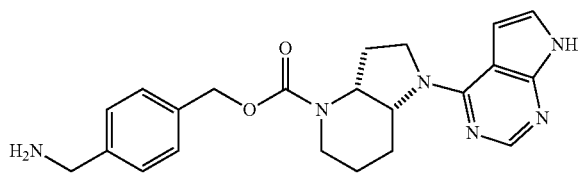

The product from Example 8-1 (4-{[(tert-butoxycarbonyl)amino]methyl}benzyl(3aR, 7aR)-1-(7H-pyrrolo[2,3-d]pyrimidin-4-yl)octahydro-4-pyrrolo[3,2-b]pyridine-4-carboxylate) was dissolved in DCM (0.20 mL) and TFA (0.048 mL, 0.62 mmol) was added. The mixture was allowed to stir at ambient temperature for 30 minutes and the resulting mixture was concentrated in vacuo A 1:1 mixture of water and acetonitrile was added, the resulting mixture was frozen and lyophilized to afford the title compound (TFA salt) as a white solid. LRMS calc'd for $C_{22}H_{26}N_6O_2$ [M+H]$^+$, 407; found 407. Jak1 activity: +.

Example 10

4-(hydroxymethyl)benzyl (3aR,7aR)-1-(7H-pyrrolo[2,3-d]pyrimidin-4-yl)octahydro-4H-pyrrolo[3,2-b]pyridine-4-carboxylate (TFA salt)

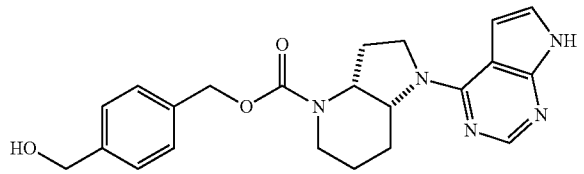

Step 1: 4-({[tert-butyl(dimethyl)silyl]oxy}methyl)benzyl (3aR,7aR)-1-(7H-pyrrolo[2,3-d]pyrimidin-4-yl)octahydro-4H-pyrrolo[3,2-b]pyridine-4-carboxylate

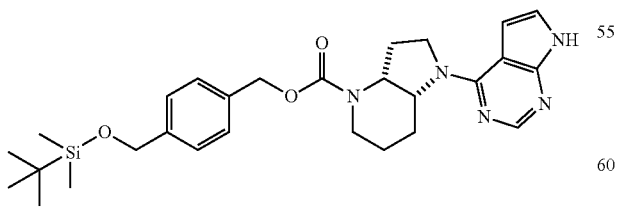

This intermediate was prepared in analogy to that described for the preparation of Example 8-1 above. The crude resulting mixture was carried on without purification. LRMS calc'd for $C_{28}H_{39}N_5O_3Si$ [M+H]$^+$, 522; found 522.

Step 2: 4-hydroxymethyl)benzyl (3aR,7aR)-1-(7H pyrrolo[2,3-d]pyrimidin-4-1 octahydro-4H-pyrrolo[3,2-b]pyridine-4-carboxylate (TFA salt)

To a stirred solution of the product of Step 1 above (43 mg, 0.082 mmol) in THF (0.82 mL) at 0° C. was added TBAF (0.49 mL, 0.49 mmol). The resulting mixture was allowed to stir at ambient temperature for 18 hours. The reaction mixture was partitioned between EtOAc (25 mL) and water (25 mL). The layers were separated, collected and washed with saturated aqueous ammonium chloride followed by saturated aqueous sodium chloride. The organic layer was collected, dried over sodium sulfate, and concentrated in vacuo to a crude oil. The crude oil was dissolved in DMSO (2.0 mL) and purified by mass-triggered reverse-phase HPLC. Lyophilization of the desired fractions afforded the title product (TFA salt) as a white solid. LRMS calc'd for $C_{22}H_{25}N_5O_3$ [M+H]$^+$, 407; found 407. Jak1 activity: +.

Example 11 tert-butyl (3aR,7aR)-1-(7H-pyrrolo[2,3-d]pyrimidin-4-yl)octahydro-4H-pyrrolo[3,2-b]pyridin-4-carboxylate

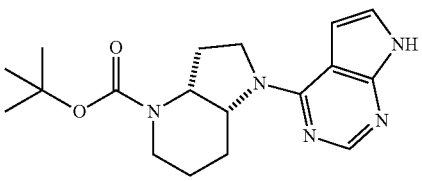

To a stirred solution of enantiomer 2 of Example 2 (20 mg, 0.082 mmol) in acetonitrile (0.82 mL) was added Boc$_2$O (0.019 mL, 0.082 mmol) and DMAP (1.0 mg, 0.008 mmol). The resulting mixture was allowed to stir at ambient temperature for 18 hours. The reaction mixture was partitioned between EtOAc (25 mL) and saturated aqueous sodium bicarbonate (25 mL). The organic layer was collected, dried over sodium sulfate, and concentrated in vacuo. The crude reaction mixture was purified by column chromatography on silica gel eluting with EtOAc/hexane (0-100%) followed by DCM:MeOH (90:10). The product fractions were concentrated in vacuo to afford the desired product as a white solid. LRMS calc'd for $C_{18}H_{25}N_5O_2$ [M+H]$^+$, 344; found 344. Jak1 activity: +.

Example 12

(3aS,7aS and 3aR,7aR) 3-oxo-3-[1-(7H-pyrrolo[2,3-d]pyrimidin-4-yl)octahydro-4H-pyrrolo[3,2-b]pyridin-4-yl]propanenitrile (TFA salt)

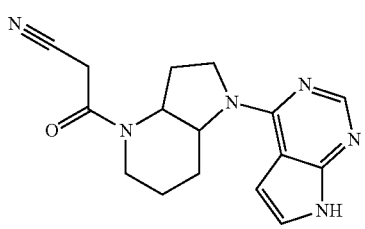 [SMILES: N#CCC(=O)N1CCCC2C1CCN2c1ncnc2[nH]ccc12]

DBU (90 μL, 0.60 mmol) was added to a stirred room temperature mixture of the product of Example 2, Step 1 (50 mg, 0.12 mmol) in 2-methyltetrahydrofuran (123 μL) and NMP (123 μL) in a sealed vial. The mixture was heated to 40° C. and methyl cyanoacetate (22 μL, 0.25 mmol) was then added, and the mixture was stirred at 40° C. for 16 hours. The mixture was concentrated to a crude solid/liquid mixture and the residue was purified by mass triggered reverse phase HPLC. The product containing fractions were lyophilized to afford the title product (TFA salt) as a white solid. LRMS calc'd for $C_{16}H_{19}N_6O$ [M+H]$^+$, 311; found 311. Jak1 activity: ++.

Example 13 methyl 4-{3-[(3aR,7aR)-1-(7H-pyrrolo[2,3-d]pyrimidin-4-yl)octahydro-4H-pyrrolo[3,2-b]pyridin-4-yl]propyl}benzoate (TFA salt)

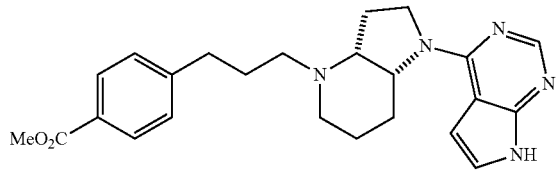

Sodium triacetoxyborohydride (44 mg, 0.21 mmol) was added to a stirred room temperature solution of enantiomer 2 of Example 2 (25 mg, 0.10 mmol) and methyl 4-(3-oxopropyl)benzoate (59 mg, 0.31 mmol) in THF (1.0 mL) in a sealed vial under nitrogen. The mixture was stirred for 72 hours at room temperature before being concentrated in vacuo to a crude solid/liquid mixture that was purified by mass triggered reverse phase HPLC. The product containing fractions were lyophilized to give the title product (TFA salt) as a white solid. LRMS calc'd for $C_{24}H_{30}N_5O_2$ [M+H]$^+$, 421; found 420. Jak1 activity: +.

Example 14

4-{3-[(3aR,7aR)-1-(7H-pyrrolo[2,3-d]pyrimidin-4-yl)octahydro-4H-pyrrolo[3,2-b]pyridin-4-yl]propyl}benzoic acid (TFA salt)

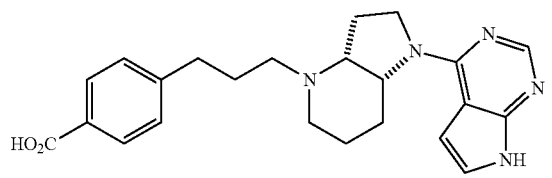

An aqueous 0.5 M solution of lithium hydroxide (625 μL, 0.081 mmol) was added to a stirred room temperature solution of the product of Example 13 (11 mg, 0.026 mmol) in methanol (100 μL). The mixture was stirred for 16 hours at room temperature and was then concentrated in vacuo to a crude solid/liquid mixture. The residue was purified by mass triggered reverse phase HPLC. The product containing fractions were lyophilized to give the title compound (TFA salt) as a white solid. LRMS calc'd for $C_{23}H_{28}N_5O_2$ [M+H]$^+$, 407; found 406. Jak1 activity: +.

Example 15

(3aS,7aS and 3aR,7aR) benzyl 1-(6-methyl-7H-pyrrolo[2,3-d]pyrimidin-4-yl)octahydro-4H-pyrrolo[3,2-b]pyridine-4-carboxylate

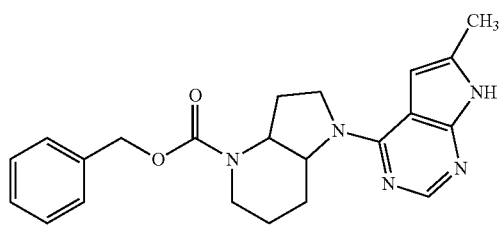 [SMILES: Cc1cc2c(N3CCC4C3CCCN4C(=O)OCc3ccccc3)ncnc2[nH]1]

Step 1: 4-chloro-6-methyl-7-{[2-(trimethylsilyl)ethoxy]methyl}-7H-pyrrolo[2,3-d]pyrimidine

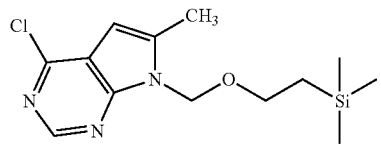 [SMILES: Cc1cc2c(Cl)ncnc2n1COCC[Si](C)(C)C]

To a stirred solution of Intermediate 2a (100 mg, 0.352 mmol) in THF (1 mL) was added LDA (2.0M; 0.19 mL, 0.39 mmol) dropwise at −78° C. The reaction mixture was stirred at this temperature for 40 minutes, then MeI (0.11 mL, 1.8 mmol) was added and the reaction was stirred at −78° C. for an additional 40 minutes before being quenched with EtOAc and poured into a mixture of EtOAc and silica gel. The resulting mixture was concentrated in vacuo to afford a crude solid that was purified by column chromatography on silica gel, eluting with EtOAc/hexane (2-20%) to afford the desired product as a colorless oil. LRMS calc'd for $C_{13}H_{21}ClN_3OSi$ [M+H]$^+$, 298; found 298. $^1$H NMR (500 MHz, CDCl$_3$) δ 8.60 (s, 1H), 6.40 (s, 1H), 5.65 (s, 2H), 3.51 (t, 2H), 2.56 (s, 3H), 0.90 (t, 2H), 0.06 (s, 9H).

Step 2: (3aS,7aS and 3aR,7aR) benzyl 1-(6-methyl-7-{[2-(trimethylsilyl)ethoxy]methyl}-7H-pyrrolo[2,3-d]pyrimidin-4-yl)octahydro-4H-pyrrolo[3,2-b]pyridine-4-carboxylate

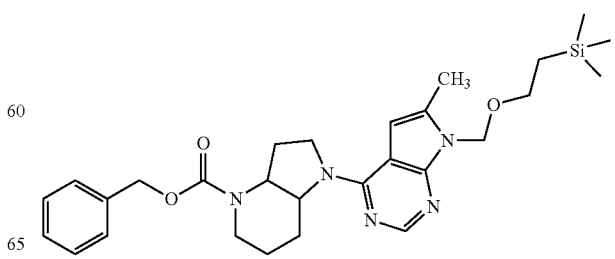

This intermediate was prepared in analogy to that which was described for the preparation of Example 1. LRMS calc'd for $C_{28}H_{40}N_5O_3Si$ [M+H]+, 522; found 522.

Step 3: (3aS,7aS and 3aR,7aR) benzyl 1-(6-methyl-7H-pyrrolo[2,3-d]-pyrimidin-4-yl)octahydro-4H-pyrrolo[3,2-b]pyridine-4-carboxylate This example was prepared in analogy to that which was described for the preparation of Example 1. LRMS calc'd for $C_{22}H_{26}N_5O_2$ [M+H]+, 392; found 392. $^1$H NMR (500 MHz, DMSO-$D_6$) δ 11.4 (s, 1H), 7.99 (s, 1H), 7.40-7.26 (br m, 5H), 6.20 (s, 1H), 5.10 (m, 2H), 4.59 (br s, 1H), 4.28 (br s, 1H), 3.97-3.62 (br m, 3H), 2.99-2.80 (br m, 1H), 2.30-2.14 (overlapping s, m, 5H), 2.02 (br m, 1H), 1.63 (br m, 1H), 1.43 (br m, 1H), 1.30 (br m, 11-1). Jak1 activity: ++.

Example 16

(3aS,7aS and 3aR,7aR) benzyl 4-(7H-pyrrolo[2,3-d]pyrimidin-4-yl)octahydro-1H-pyrrolo[3,2-b]pyridine-1-carboxylate

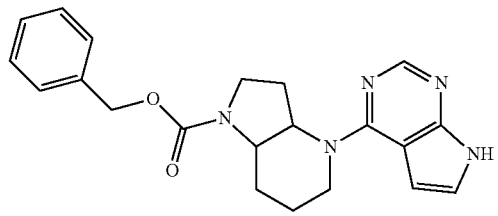 [SMILES: O=C(OCc1ccccc1)N1CCC2C1CCCN2c1ncnc2[nH]ccc12]

Step 1: (3aS,7aS and 3aR,7aR) tert-butyl 4-(7-{[2-(trimethylsilyl)ethoxy]methyl}-7H-pyrrolo[2,3-d]-pyrimidin-4-yl)octahydro-1H-pyrrolo[3,2-b]pyridine-1-carboxylate

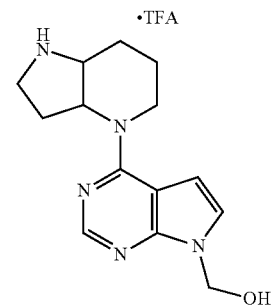 [SMILES: OCn1ccc2c(N3CCCC4NCCC43)ncnc21]

To a stirred solution of Intermediate 2a (0.700 g, 2.47 mmol) and (3aS,7aS and 3aR,7aR) text-butyl octahydro-1H-pyrrolo[3,2-b]pyridine-1-carboxylate (HOAc salt; 0.918 g, 3.21 mmol; Intermediate 1a process, Step 4) in DMF (14 mL) was added TEA (1.03 mL, 7.40 mmol). The resulting reaction mixture was stirred at 90° C. overnight. The reaction mixture was partitioned between EtOAc and 10% aqueous sodium chloride and the organic layer was washed with additional 10% aqueous sodium chloride. The first aqueous layer was extracted with additional EtOAc and the combined organic washings were dried over sodium sulfate and filtered. Silica gel was added to the filtrate and the mixture was concentrated in vacuo to a crude solid. The resulting solid was purified by column chromatography on silica gel, eluting with EtOAc/hexane (12-100%) to afford the desired product. LRMS calc'd for $C_{24}H_{40}N_5O_3Si$ [M+H]+, 474; found 474. $^1$H NMR (500 MHz, DMSO-$D_6$) δ 8.20 (s, 1H), 7.35 (d, 1H), 6.69 (d, 1H), 5.50 (s, 2H), 5.13 (br m, 1H), 4.59 (br d, 1H), 3.80-3.68 (br m, 1H), 3.47 (t, 2H), 3.41-3.32 (br m, 2H), 3.05 (br t, 1H), 2.09 (br m, 2H), 1.99 (br m, 1H), 1.75 (br m, 1H), 1.39 (overlapping s, m, 11H), 0.80 (t, 2H), −0.10 (s, 9H).

Step 2: (3aS,7aS and 3aR,7aR) 4-[7-(hydroxymethyl)-7H-pyrrolo[2,3-d]pyrimidin-4-yl]-octahydro-1H-pyrrolo[3,2-b]pyridin-1-yl (TFA salt)

To a stirred solution of the product of Step 1 (0.170 g, 0.359 mmol) in DCM (1.3 mL) was added TFA (1.3 mL). The resulting solution was stirred at ambient temperature for 30 minutes and then concentrated in vacuo. The resulting oil was azeotroped with DCM several times to afford the desired product that was carried on without further purification. LRMS calc'd for $C_{14}H_{20}N_5O$ [M+H]+, 274; found 274.

Step 3: (3aS,7aS and 3aR,7aR) benzyl 4-(7H-pyrrolo[2,3-d]pyrimidin-4-yl)octahydro-1H-pyrrolo[3,2-b]pyridine-1-carboxylate To a stirred solution of the product of Step 2 (0.070 g, 0.14 mmol) in THF (0.6 mL) was added 2M aqueous sodium carbonate (0.70 mL, 1.4 mmol). The resulting biphasic mixture was cooled to 0° C., then benzyl chloroformate (0.024 mL, 0.17 mmol) was added. The reaction mixture was allowed to stir while the bath naturally warmed to ambient temperature. A white precipitate formed and the reaction was diluted with ethyl acetate and water and allowed to stir for 16 hours at room temperature. The reaction mixture was partitioned between EtOAc and water, and the organic layer was separated, dried over sodium sulfate, filtered, and concentrated in vacuo to a crude oil. The resulting oil was purified by silica gel with a 12-100% EtOAc/hexanes gradient to afford the title compound. LRMS calc'd for $C_{21}H_{24}N_5O_2$ [M+H]+, 378; found 378. $^1$H NMR (500 MHz, DMSO-$D_6$) δ 11.7 (s, 1H), 8.13 (s, 1H), 7.39-7.26 (m, 5H), 6.59 (m, 1H), 5.18 (m, 1H), 5.13-5.02 (m, 2H), 4.59 (br d, 1H), 3.84 (br septet, 1H), 3.54-3.36 (m, 3H), 3.04 (br m, 1H), 2.13 (br in, 1H), 2.10-1.97 (br m, 2H), 1.75 (br m, 1H), 1.43 (br m, 2H). Jak1 activity: ++.

Example 17

(3aS,7aS and 3aR,7aR) 2-hydroxy-1-[1-(7H-pyrrolo [2,3-d]pyrimidin-4-yl)octahydro-4H-pyrrolo[3,2-b] pyridine-4-yl]ethanone

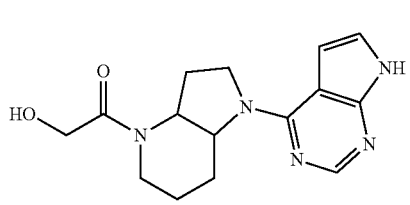 [SMILES: O=C(CO)N1CCCC2C1CCN2c1ncnc2[nH]ccc12]

To the product of Example 2, Step 1 (100 mg, 0.247 mmol), was added toluene (617 µL) and THF (617 µL) and 2,2-dimethyl-1,3-dioxolan-4-one (43.5 µL, 0.370 mmol). The reaction was refluxed overnight, then cooled and concentrated in vacuo. The reaction was purified by column chromatography using silica, eluting with 2-8% CH$_2$Cl$_2$/MeOH. The product was collected and concentrated to afford the desired product as a colorless solid. LRMS calc'd for C$_{15}$H$_{20}$N$_5$O$_2$ [M+H]$^+$, 302; found 302. Jak1 activity: +.

Example 18

(2S)-3,3,3-trifluoro-2-methoxy-2-phenyl-1-[(3aR, 7aR)-1-(7H-pyrrolo[2,3-d]pyrimidin-4-yl)octahydro-4H-pyrrolo[3,2-b]pyridine-4-yl]propan-1 one (TFA salt)

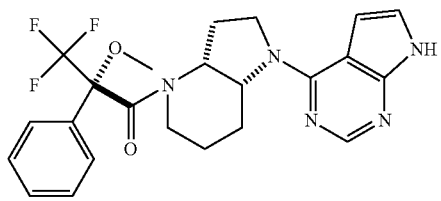

To enantiomer 2 of Example 2 (20 mg, 0.084 mmol) in DCM (168 µL), was added DIPEA (17.6 µL, 0.101 mmol) and (R)-(−)-α-methoxy-α-(trifluoromethyl)phenylacetyl chloride (15 mg, 0.057 mmol). The reaction was stirred for 16 hours, then concentrated in vacuo and the residue was purified by mass triggered reverse phase HPLC. Lyophilization afforded the title product (TFA salt) as a white solid. LRMS calc'd for C$_{23}$H$_{25}$F$_3$N$_5$O$_2$ [M+H]$^+$, 460; found 460. Jak1 activity: +.

Example 19

(2R)-3,3,3-trifluoro-2-methoxy-2-phenyl-1-[(3aR, 7aR)-1-(7H-pyrrolo[2,3-d]pyrimidin-4-yl)octahydro-4H-pyrrolo[3,2-b]pyridine-4-yl]propan-1-one (TFA salt)

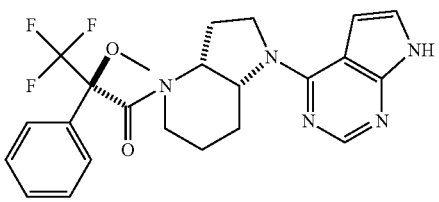

Following a similar procedure to Example 18 above using enantiomer 2 of Example 2 and (S)-(+)-α-methoxy-α-(trifluoromethyl)phenylacetyl chloride gave the title compound (TFA salt) as a white solid. LRMS calc'd for C$_{23}$H$_{25}$F$_3$N$_5$O$_2$ [M+H]$^+$, 460; found 460. Jak1 activity: ++.

Example 20

(3aS,7S,7aS and 3aR,7R,7aR) benzyl 7-methyl-1-(7H-pyrrolo[2,3-d]pyrimidin-4-yl)octahydro-4H-pyrrolo[3,2-b]pyridine-4-carboxylate

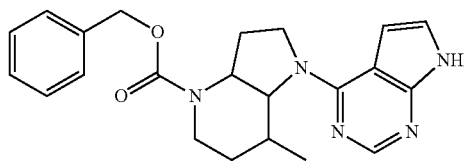 [SMILES: CC1CCN(C(=O)OCc2ccccc2)C2CCN(c3ncnc4[nH]ccc34)C12]

Step 1: tert-butyl 5-chloro-7-methyl-1H-pyrrolo[3,2-b]pyridine-1-carboxylate

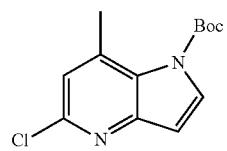 [SMILES: Cc1cc(Cl)nc2ccn(C(=O)OC(C)(C)C)c12]

To 5-chloro-7-methyl-1H-pyrrolo[3,2-b]pyridine (500 mg, 3.00 mmol) in THF (3.0 mL), was added TEA (418 µL, 3.00 mmol) and DMAP (367 mg, 3.00 mmol) and Boc$_2$O (766 µL, 3.30 mmol) at 0° C. The reaction was stirred at room temperature for 16 hours, concentrated in vacuo and purified by column chromatography on silica gel using 5-40% ethyl acetate/hexanes to afford desired product as a white solid. LRMS calc'd for C$_{13}$H$_{16}$N$_2$O$_2$Cl [M+H]$^+$, 267; found 267.

¹H NMR (500 MHz, CDCl₃) δ 7.78 (d, J' 3.9Hz, 1H), 7.05 (s, 1H), 6.67 (d, J=3.8Hz), 2.70 (s, 3H), 1.65 (s, 9H).

Step. 2: (3aS,7S,7aS and 3aR,7R,7aR) tert-butyl 7-methyloctahydro-1H-pyrrolo[3,2-b]pyridine-1-carboxylate

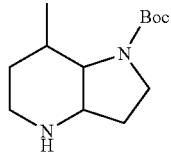 [SMILES: CC1CCNC2CCN(C(=O)OC(C)(C)C)C12]

To the product of Step 1 (361 mg, 1.35 mmol) was added platinum(IV) oxide (310 mg, 1.37 mmol) in a Parr pressure flask. The flask was purged with nitrogen by successive evacuation/nitrogen backfills and then acetic acid (15 mL) was added. The reaction mixture was placed under hydrogen atmosphere by successive evacuation/hydrogen backfills and the reaction was shaken at 40 psi for 5 days. The reaction was then filtered through Celite and washed with AcOH and concentrated in vacuo to afford a crude oil that was taken onto the next step without further purification. LRMS calc'd for $C_{13}H_{25}N_2O_2$ [M+H]⁺, 241; found 241.

Step 3: (3aS,7S,7aS and 3aR,7R,7aR) 4-benzyl 1-tert-butyl 7-methylhexahydro-1H-pyrrolo[3,2-b]pyridine-1,4(2H)-dicarboxylate

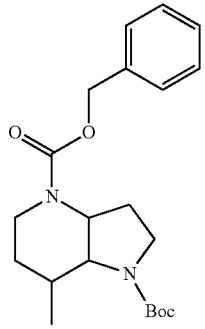 [SMILES: CC1CCN(C(=O)OCc2ccccc2)C2CCN(C(=O)OC(C)(C)C)C12]

To the product of Step 2 (888 mg, 2.96 mmol), was added THF (13.4 mL), aqueous sodium carbonate (2M, 7.39 mL, 14.8 mmol) solution, and CBZ-Cl (633 μL, 4.43 mmol) at 0° C. The reaction was allowed to warm to 25° C. for 3 hours before being quenched with water and extracted with ethyl acetate (3×50 mL). The organic washings were combined and dried with Na₂SO₄, filtered, and evapourated in vacuo. The crude product was then purified by silica chromatography eluting with 5-40% EtOAc/hexane. The product was collected and concentrated in vacuo to afford the cis fused product as a colorless oil. LRMS calc'd for $C_{16}H_{23}N_2O_2$ [{M-Boc+H}+H]⁺, 275; found 275.

Step 4: (3aS,7S,7aS and 3aR,7R,7aR) 4-benzyl 1-tert-butyl 7-methylhexahydro-1H-pyrrolo[3,2-b]pyridine-1,4(2H)-dicarboxylate (TFA salt)

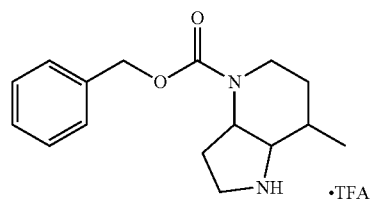 [SMILES: CC1CCN(C(=O)OCc2ccccc2)C2CCNC12]

To the product of Step 3 (657 mg, 1.75 mmol) was added DCM (5.8 mL) and TFA (4.73 mL, 61.4 mmol). The reaction was stirred at 25° C. for 3 hours and then reduced in vacuo and azeotroped with heptanes (×3) to afford a slightly, brown oil (as the TFA salt) that was used without further purification.

Step 5: (3aS,7S,7aS and 3aR,7R,7aR) benzyl 7-methyl-1-(7-{[2-(trimethylsilyl)ethoxy]methyl}-7H-pyrrolo[2,3-d]pyrimidin-4-yl)octahydro-4H-pyrrolo[3,2-b]pyridine-4-carboxylate

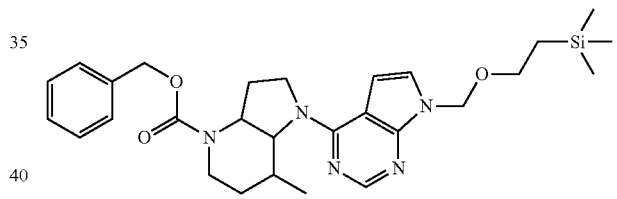

Following a similar procedure to that used in Example 1, Step 2, using the product of Step 4 and Intermediate 2a gave the desired product as a yellow oil. LRMS calc'd for $C_{28}H_{40}N_5O_3Si$ [M+H]⁺, 522; found 522. ¹H NMR (500 MHz, CDCl₃) δ 8.31 (m, 1H), 8.02 (s, 1H), 7.42-7.28 (m, 4H), 7.05 (m, 1H), 6.52-6.63 (m, 1H), 5.58 (s, 2H), 5.18 (s, 2H), 4.74-4.50 (m, 2H), 4.05-3.86 (m, 2H), 3.53 (AB, 2H), 3.39 (s, 2H), 3.13 (m, 1H), 2.51-2.25 (m, 1H), 2.05 (m, 1H), 1.88-1.60 (m, 3H), 0.93 (m, 4H), −0.05 (s, 9H).

Step 6: (3aS,7S,7aS and 3aR,7R,7aR) benzyl 7-methyl-1-(7H-pyrrolo[2,3-d]pyrimidin-4-yl)octahydro-4H-pyrrolo[3,2-b]pyridine-4-carboxylate Following a similar procedure to that used in Example 1, Step 3, using the product of Step 5, gave the title product as a white solid (as the all cis product, (3aS,7S,7aS and 3aR,7R, 7aR)). LRMS calc'd for $C_{22}H_{26}N_5O_2$ [M+H]⁺, 392; found 392. ¹H NMR (600 MHz, DMSO-D₆ at 60° C.) δ 11.51 (s, 1H), 8.13 (s, 1H), 7.43-7.35 (m, 5H), 7.13 (s, 1H), 6.61 (s, 1H), 5.18 (AB, 2H), 4.61-4.53 (m, 2H), 4.01-3.84 (m, 2H), 3.21 (m, 4H), 2.81 (m, 1H), 2.33-2.07 (m, 2H), 1.82-1.60 (m, 2H), 0.89 (d, J—7.8Hz, 3H). Jak1 activity: ++.

Example 21

(3aS,7S,7aS and 3aR,7R,7aR) 4-(4-benzyl-7-methyloctahydro-1H-pyrrolo[3,2-b]pyridin-1-yl)-7H-pyrrolo[2,3-d]pyrimidine (TFA salt)

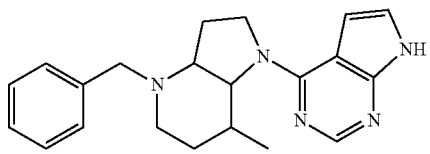 [SMILES: CC1CCN(Cc2ccccc2)C2CCN(c3ncnc4[nH]ccc34)C12]

To the product of Example 20 (40 mg, 0.102 mmol), was added HBr in acetic acid (1.5 mL, 0.102 mmol) and the reaction was stirred at room temperature for 2 hours before being concentrated in vacuo and azeotroped with heptanes (×2) and MeOH/heptanes (×1). The residue was taken up in methanol and passed through a Varian StratoSpheres™ SPE PL-HCO₃ MP SPE resin. The solution was concentrated in vacuo and taken back up in MeOH (0.10 mL) and an additional amount of benzyl bromide (12.2 mg, 0.0714 mmol) was added and the reaction was stirred at 40° C. for 16 hours. The reaction was concentrated in vacuo and purified by mass triggered reverse phase HPLC. Lyophilization of the desired fractions gave the title product (TFA salt) as a white solid. LRMS calc'd for $C_{21}H_{26}N_5$ [M+H]$^+$, 348; found 348. Jak1 activity: ++.

Example 22

(3aS,7S,7aS and 3aR,7R,7aR) 3-[7-methyl-1-(7H-pyrrolo[2,3-d]pyrimidin-4-yl)octahydro-4H-pyrrolo[3,2-b]pyridin-4-yl]-3-oxopropanenitrile (TFA salt)

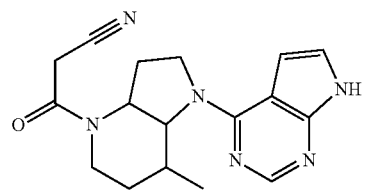 [SMILES: CC1CCN(C(=O)CC#N)C2CCN(c3ncnc4[nH]ccc34)C12]

To the product of Example 20 (30 mg, 0.077 mmol), was added HBr in acetic acid (1.5 mL, 0.10 mmol) and the reaction was stirred at room temperature for 2 hours before being concentrated in vacuo and azeotroped with heptanes (×4) and MeOH/heptanes (×3). The solid was dried under high vacuum and was then dissolved in methanol and passed through a Varian StratoSpheres™ SPE PL-HCO₃ MP SPE resin and concentrated in vacuo. The solid was dissolved in MeOH (0.4 mL) and DBU (5.8 μL, 0.038 mmol) and methyl cyanoacetate (15.2 mg, 0.153 mmol) were added and the reaction was stirred at 40° C. for 16 hours. The reaction was concentrated in vacuo and the residue was purified by mass triggered reverse phase HPLC. Lyophilization of the desired fractions gave the title product (TFA salt) as a off-white solid. LRMS calc'd for $C_{17}H_{21}N_6O$ [M+H]$^+$, 325; found 325. Jak1 activity: +.

Example 23 methyl 4-[({[(3aR,7aR)-1-(7H-pyrrolo[2,3-d]pyrimidin-4-yl)octahydro-4H-pyrrolo[3,2-b]-pyridine-4-yl]carbonyl}amino)methyl]benzoate (TFA salt)

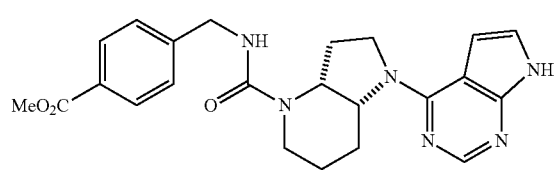

To methyl 4-(aminomethyl)benzoate (25 mg, 0.12 mmol), was added DCM (376 μL), DIPEA (43 μL, 0.25 mmol) and triphosgene (11 mg, 0.037 mmol) at 0° C. The reaction was stirred for 2.5 hours before 4-[(3aR,7aR)-octahydro-1H-pyrrolo[3,2-b]pyridin-1-yl]-7H-pyrrolo[2,3-d]pyrimidine (30.2 mg, 0.124 mmol) was added. The resulting solution was stirred for an additional 3 hours before being concentrated in vacuo and purified by mass triggered reverse phase HPLC. Lyophilization of the desired fractions gave the title compound (TFA salt) as a white solid. LRMS calc'd for $C_{23}H_{27}N_6O_3$ [M+H]$^+$, 435; found 435. Jak1 activity: ++.

Example 24 methyl 4-[(methyl{[(3aR,7aR)-1-(7H-pyrrolo[2,3-d]pyrimidin-4-yl)octahydro-4H-pyrrolo[3,2-b]-pyridin-4-yl]carbonyl}amino)methyl]benzoate (TFA salt)

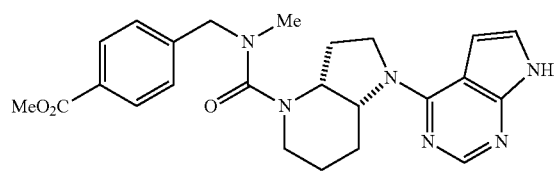

The title compound was prepared in an analogous manner to Example 23 above, using methyl 4-[(methylamino)methyl]benzoate. LRMS calc'd for $C_{24}H_{29}N_6O_3$ [M+H]$^+$, 449; found 449. Jak1 activity: +++.

Example 25

4-[({[(3aR,7aR)-1-(7H-pyrrolo[2,3-d]pyrimidin-4-yl)octahydro-4H-pyrrolo[3,2-b]pyridin-4-yl]carbonyl}amino)methyl]benzoic acid (TFA salt)

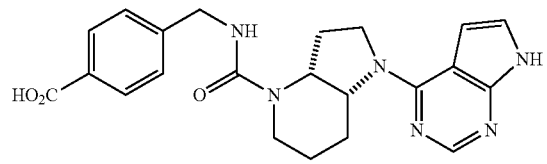

To methyl 4-[({[(3aR,7aR)-1-(7H-pyrrolo[2,3-d]pyrimidin-4-yl)octahydro-4H-pyrrolo[3,2-b]pyridine-4-yl]carbonyl}amino)methyl]benzoate (TFA salt) from Example 23 (8.2 mg, 0.015 mmol) was added MeOH (75 µL) and aqueous lithium hydroxide (299 µL, 0.149 mmol, 2.0 M) solution at 22° C. The reaction was stirred for 18 hours before being concentrated and dissolved in DMSO (2.0 mL). The resulting solution was purified by mass triggered reverse phase HPLC. Lyophilization of the desired fractions gave the title compound (TFA salt). LRMS calc'd for $C_{22}H_{25}N_6O_3$ [M+H]$^+$, 421; found 421. Jak1 activity: +.

Example 26 methyl 4-{3-oxo-3-[(3aR,7aR)-1-(7H-pyrrolo[2,3-d]pyrimidin-4-yl)octahydro-4H-pyrrolo[3,2-b]pyridine-4-yl]propyl}benzoate (TFA salt)

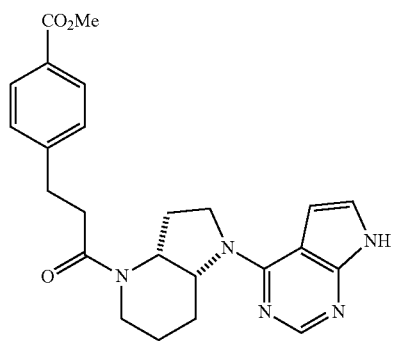

To enantiomer 2 of Example 2 (20 mg, 0.082 mmol), was added 3-[4-(methoxy-carbonyl)phenyl]propanoic acid (19 mg, 0.090 mmol), TEA (46 µL, 0.33 mmol), DMF (822 µL) and 3-(diethoxyphosphoryloxy)-1,2,3-benzotriazin-4(3H)-one (DEPBT) (49 mg, 0.16 mmol). The reaction was stirred at 25° C. for 60 hours and was then concentrated in vacuo and purified by mass triggered reverse phase HPLC. Lyphilization of the desired fractions afforded the title compound (TFA salt) as a white solid. LRMS calc'd for $C_{24}H_{28}N_5O_3$ [M+H]$^+$, 434; found 434. Jak1 activity: ++.

Example 27

4-{3-oxo-3-[(3aR,7aR)-1-(7H-pyrrolo[2,3-d]pyrimidin-4-yl)octahydro-4H-pyrrolo[3,2-b]pyridin-4-yl]propyl}benzoic acid (TFA salt)

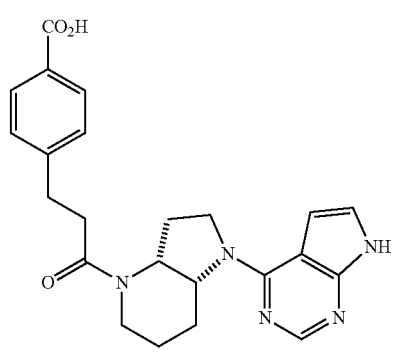

The title compound was prepared in an analogous manner to Example 25 above, using methyl 4-{3-oxo-3-[(3aR,7aR)-1-(7H-pyrrolo[2,3-d]pyrimidin-4-yl)octahydro-4H-pyrrolo[3,2-b]pyridine-4-yl]propyl}benzoate (TFA salt) from Example 26 (13 mg, 0.024 mmol). LRMS calc'd for $C_{23}H_{26}N_5O_3$ [M+H]$^+$, 420; found 420. Jak1 activity: ++.

Example 28

4-[2-({[(3aR,7aR)-1-(7H-pyrrolo[2,3-d]pyrimidin-4-yl)octahydro-4H-pyrrolo[3,2-b]pyridin-4-yl]carbonyl}oxy)ethyl]benzoic acid (TFA salt)

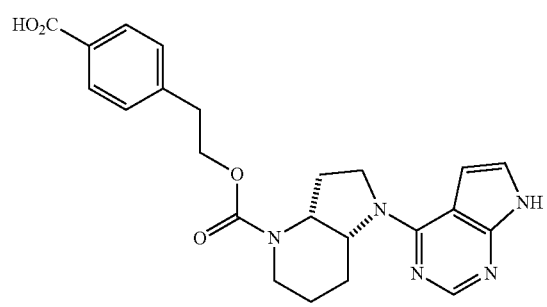

The title compound was prepared in an analogous manner to Example 25 above, using 2-[4-(methoxycarbonyl)phenyl]ethyl (3aR,7aR)-1-(7H-pyrrolo[2,3-d]pyrimidin-4-yl)octahydro-4H-pyrrolo[3,2-b]pyridine-4-carboxylate (TFA salt)

from Example 3-21 (8.1 mg, 0.014 mmol). LRMS calc'd for $C_{23}H_{26}N_5O_4$ [M+H]$^+$, 436; found 436. Jak1 activity: +.

Example 29-1

(3aS,7aS and 3aR,7aR) 4-{4-[(4-morpholin-4-ylphenyl)carbonyl]octahydro-1H-pyrrolo[3,2-b]pyridin-1-yl}-7H-pyrrolo[2,3-d]pyrimidine

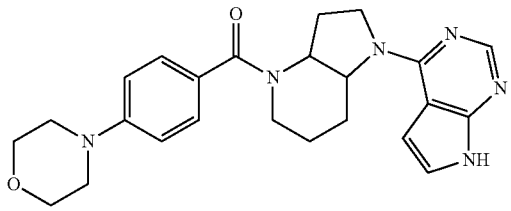 [SMILES: O=C(c1ccc(N2CCOCC2)cc1)N1CCCC2C1CCN2c1ncnc2[nH]ccc12]

To a solution of the product of Example 2, step 1 (20 mg, 0.049 mmol), 4-(morpholin-4-yl)benzoic acid (10 mg, 0.049 mmol), and 3-(diethoxyphosphoryloxy)-1,2,3-benzotriazin-4(3H)-one (DEPBT) (30 mg, 0.099 mmol) in DMF (0.49 mL) was added triethylamine (28 µL, 0.20 mmol) at room temperature. The solution was stirred for 20 hours. The reaction mixture was purified by mass-triggered reverse-phase HPLC using 0.1% formic acid modifier. Lyophilization of the desired fractions afforded the title compound as a white solid. LRMS calc'd for $C_{24}H_{29}N_6O_2$ [M+H]$^+$, 433; found 433. $^1$H NMR (500 MHz, DMSO-D$_6$) δ 11.6 (s, 1H), 8.03 (s, 1H), 7.64 (dd, 2H), 7.43 (dd, 2H), 7.08 (s, 1H), 6.51 (s, 1H), 4.89 (br s, 0.5H), 4.61 (br s, 0.5H), 4.35-4.24 (m, 2H), 4.00-3.68 (br m, 5H), 3.02 (t, 0.5H), 2.63 (t, 0.5H), 2.35-1.91 (br m, 4H), 1.62 (br t, 2H), 1.34 (br m, 3H). Jak1 activity: +.

The following compounds below in Table 4 were prepared in analogy to the preparation of Example 29-1 above, by substituting 4-(morpholin-4-yl)benzoic acid with the appropriately functionalized carboxylic acids and either racemic or 4-[(3aR,7aR)-octahydro-1H-pyrrolo[3,2-b]pyridin-1-yl]-7H-pyrrolo[2,3-d]pyrimidine. The compounds were isolated by mass-triggered reverse-phase HPLC using a Waters X-bridge Prep C18 column (5 micron, 19×100 mm), eluting with an ACN/water gradient (using 0.1% NH$_4$OH as a basic modifier, or alternatively 0.1% formic acid or 0.1% trifluoroacetic acid as modifier).

TABLE 4

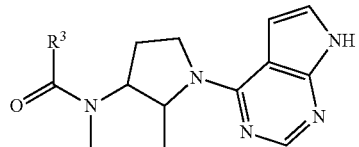

| Compound # | R3 | Exact Mass [M + H]+ | JAK1 Activity |
|---|---|---|---|
| 29-2 | n-butyl racemate | Calc'd 328, found 328 | ++ |
| 29-3 | Phenyl racemate | Calc'd 348, found 348 | ++ |

TABLE 4-continued

| Compound # | R3 | Exact Mass [M + H]+ | JAK1 Activity |
|---|---|---|---|
| 29-4 | 4-methoxybenzyl racemate | Calc'd 392, found 392 | ++ |
| 29-5 | 4-trifluoromethylbenzyl racemate | Calc'd 430, found 430 | ++ |
| 29-6 | 4-(4-methylpiperazin-1-yl)phenyl racemate | Calc'd 446, found 446 | + |
| 29-7 | Ethyl Single enantiomer | Calc'd 300, found 300 | + |
| 29-8 | —CH$_2$OCH$_3$ Single enantiomer | Calc'd 316, found 316 | + |
| 29-9 | 2-furyl | Calc'd 338, found 338 | ++ |
| 29-10 | 3-pyridyl Single enantiomer | Calc'd 349, found 349 | ++ |
| 29-11 | 2-pyridyl Single enantiomer | Calc'd 349, found 349 | + |
| 29-12 | 4-pyridyl Single enantiomer | Calc'd 349, found 349 | ++ |
| 29-13 | pyrazinyl Single enantiomer | Calc'd 350, found 350 | ++ |

TABLE 4-continued

| Compound # | R3 | Exact Mass [M + H]+ | JAK1 Activity |
|---|---|---|---|
| 29-14 | 5-methylisoxazol-3-yl Single enantiomer | Calc'd 353, found 353 | + |
| 29-15 | cyclohexyl Single enantiomer | Calc'd 354, found 354 | ++ |
| 29-16 | (2-oxopyrrolidin-1-yl)methyl Single enantiomer | Calc'd 369, found 369 | + |
| 29-17 | 2-chlorophenyl Single enantiomer | Calc'd 382, found 382 | ++ |
| 29-18 | 3-chlorophenyl Single enantiomer | Calc'd 382, found 382 | ++ |
| 29-19 | 1H-indol-2-yl Single enantiomer | Calc'd 387, found 387 | + |
| 29-20 | naphthalen-1-yl Single enantiomer | Calc'd 398, found 398 | ++ |
| 29-21 | 1-methyl-1H-indol-2-yl Single enantiomer | Calc'd 401, found 401 | ++ |
| 29-22 | 3-morpholinophenyl Single enantiomer | Calc'd 433, found 433 | + |
| 29-23 | biphenyl-2-yl Single enantiomer | Calc'd 424, found 424 | + |
| 29-24 | diphenylmethyl Single enantiomer | Calc'd 438, found 438 | + |
| 29-25 | imidazo[1,2-a]pyridin-2-yl Single enantiomer | Calc'd 388, found 338 | + |
| 29-26 | naphthalen-2-yl Single enantiomer | Calc'd 398, found 398 | ++ |

TABLE 4-continued

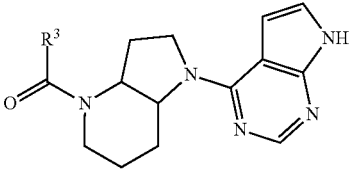

| Compound # | R3 | Exact Mass [M + H]+ | JAK1 Activity |
|---|---|---|---|
| 29-27 | 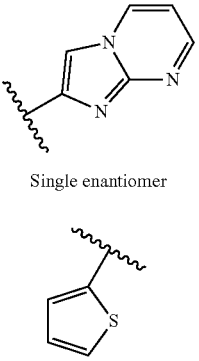  Single enantiomer | Calc'd 389, found 389 | ++ |
| 29-28 | 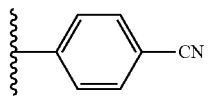  Single enantiomer | Calc'd 354, found 354 | +++ |
| 29-29 |   Single enantiomer | Calc'd 373, found 373 | ++ |
| 29-30 | 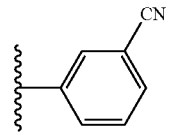  Single enantiomer | Calc'd 354, found 354 | ++ |
| 29-31 | 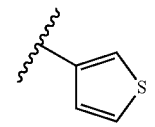  Single enantiomer | Calc'd 373, found 373 | ++ |
| 29-32 | 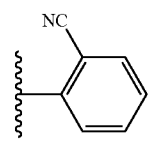  Single enantiomer | Calc'd 354, found 354 | ++ |
| 29-33 | 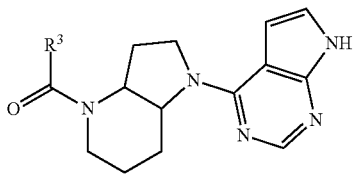  Single enantiomer | Calc'd 373, found 373 | ++ |
| 29-34 | Phenyl  Single enantiomer | Calc'd 348, found 348 | ++ |

TABLE 4-continued

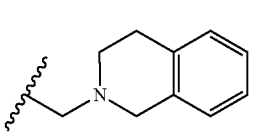

| Compound # | R3 | Exact Mass [M + H]+ | JAK1 Activity |
|---|---|---|---|
| 29-35 | 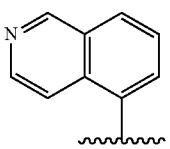  Single enantiomer | Calc'd 426, found 426 | ++ |
| 29-36 | 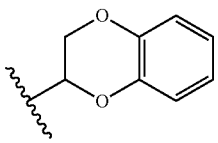  Single enantiomer | Calc'd 417, found 417 | ++ |
| 29-37 | 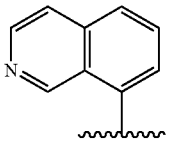  Single enantiomer | Calc'd 399, found 399 | ++ |
| 29-38 | 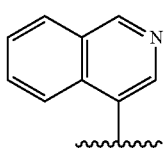  Single enantiomer | Calc'd 406, found 406 | ++ |
| 29-39 | 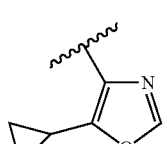  Single enantiomer | Calc'd 399, found 399 | ++ |
| 29-40 | 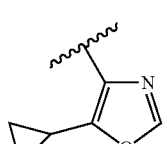  Single enantiomer | Calc'd 399, found 399 | ++ |
| 29-41 | 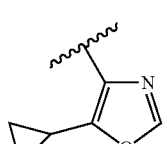  Single enantiomer | Calc'd 379, found 379 | ++ |

TABLE 4-continued

| Compound # | R3 | Exact Mass [M + H]+ | JAK1 Activity |
|---|---|---|---|
| 29-42 | benzyl with CH3 (Mixture of diastereomers (racemic acid used)) | Calc'd 390, found 390 | ++ |
| 29-43 | 1-morpholinoethyl (Mixture of diastereomers (racemic acid used)) | Calc'd 385, found 385 | ++ |
| 29-44 | quinolin-3-yl (Single enantiomer) | Calc'd 399, found 399 | ++ |
| 29-45 | 1H-pyrrolo[3,2-c]pyridin-3-yl (Single enantiomer) | Calc'd 388, found 388 | ++ |
| 29-46 | hydroxy(phenyl)methyl (Mixture of diastereomers (racemic acid used)) | Calc'd 378, found 378 | ++ |
| 29-47 | isoquinolin-1-yl (Single enantiomer) | Calc'd 399, found 399 | ++ |
| 29-48 | thieno[3,2-b]pyrrol-5-yl (Single enantiomer) | Calc'd 393, found 393 | + |
| 29-49 | imidazo[1,2-a]pyrimidin-2-yl (Single enantiomer) | Calc'd 389, found 389 | + |
| 29-50 | 1-methyl-1H-pyrrolo[2,3-b]pyridin-5-yl (Single enantiomer) | Calc'd 402, found 402 | + |
| 29-51 | quinolin-8-yl (Single enantiomer) | Calc'd 399, found 399 | + |
| 29-52 | indolizin-2-yl (Single enantiomer) | Calc'd 387, found 387 | + |
| 29-53 | 1H-benzo[d]imidazol-1-ylmethyl (Single enantiomer) | Calc'd 402, found 402 | + |
| 29-54 | 2H-indazol-2-ylmethyl (Single enantiomer) | Calc'd 402, found 402 | + |

TABLE 4-continued

| Compound # | R3 | Exact Mass [M + H]+ | JAK1 Activity |
|---|---|---|---|
| 29-55 | (3-methylpiperidin-1-yl)ethyl; Single enantiomer | Calc'd 397, found 397 | + |
| 29-56 | 1-phenylpropan-2-yl; Mixture of diastereomers (racemic acid used) | Calc'd 390, found 390 | ++ |
| 29-57 | 3-(3-fluorophenyl)isoxazol-5-yl; Single enantiomer | Calc'd 433, found 433 | + |
| 29-58 | 1-methyl-1H-pyrrolo[2,3-b]pyridin-5-yl; Single enantiomer | Calc'd 402, found 402 | + |
| 29-59 | (1-methyl-1H-indazol-5-yl)methyl; Single enantiomer | Calc'd 416, found 416 | + |
| 29-60 | 7-chloroimidazo[1,2-a]pyridin-2-yl; Single enantiomer | Calc'd 422, found 422 | + |
| 29-61 | quinolin-4-yl; Single enantiomer | Calc'd 399, found 399 | ++ |
| 29-62 | 3-oxoisoindolin-5-yl; Single enantiomer | Calc'd 403, found 403 | ++ |

Example 30

(3aS,7aS and 3aR,7aR) benzyl 1-(1H-pyrrolo[2,3-b]pyridine-4-yl)octahydro-4H-pyrrolo[3,2-b]pyridine-4-carboxylate (TFA salt)

To a stirred solution of the product of Example 1, Step 1 (136 mg, 0.524 mmol) in NMP (0.262 mL), in a microwave vial, was added Et₃N (0.073 mL, 0.52 mmol) and 4-chloro-1H-pyrrolo[2,3-b]pyridine (16 mg, 0.11 mmol). The resulting solution was heated at 160° C. for 2 hours in a Biotage Initiator microwave. An additional 4 equivalents of 4-chloro-1H-pyrrolo[2,3-b]pyridine (64 mg, 0.42 mmol) was added to the reaction mixture and the resulting solution was stirred at 160° C. for another 2 hours in a Biotage Initiator microwave. The reaction mixture was cooled to ambient temperature and partitioned between EtOAc (50 mL) and saturated sodium bicarbonate (50 mL). The layers were separated, and the organic layer was collected, dried over sodium sulfate and concentrated in vacuo to afford a crude oil that was purified by reverse phase HPLC. Lyophilization of the product fractions afforded the title compound (TFA salt) as a white solid. LRMS calc'd for $C_{22}H_{25}N_4O_2$ [M+H]+, 377; found 377. Jak1 activity: +.

Example 31

(3aS,7aS and 3aR,7aR) 4-[4-(5-phenyl-1,3,4-oxadiazol-2-yl)octahydro-1H-pyrrolo[3,2-b]pyridin-1-yl]-7H-pyrrolo[2,3-d]pyrimidine

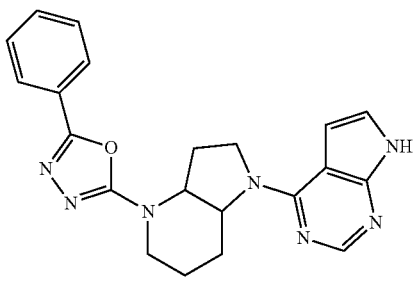 [SMILES: c1ccc(-c2nnc(N3CCCC4C3CCN4c3ncnc4[nH]ccc34)o2)cc1]

To a stirred solution of the product of Example 2, Step 1 (40 mg, 0.099 mmol) and 2-bromo-5-phenyl-1,3,4-oxadiazole (22 mg, 0.099 mmol) in THF (395 µL) was added 1,8-diazabicyclo[5.4.0]undec-7-ene (45 µL, 0.30 mmol). The resulting slurry was sealed and heated at 80° C. for 90 minutes, at which point additional solvent (dioxane, 500 µL) was added. The resulting mixture was stirred at 80° C. for 18 hours, then cooled to 23° C., and purified by mass-triggered reverse-phase HPLC. Lyophilization of the desired fractions gave the title compound (TFA salt) as a solid. LCMS calc'd for $C_{21}H_{22}N_7O$ [M+H]+, 388; found 388. Jak1 activity: +.

Example 32-1

4-{(3aR,7aR)-4-[(1-methylethyl)sulfonyl]octahydro-1H-pyrrolo[3,2-b]pyridin-1-yl}-7H-pyrrolo[2,3-d]pyrimidine

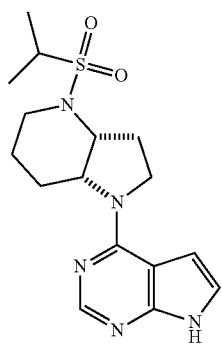

To a solution of 4-[(3aR,7aR)-octahydro-1H-pyrrolo[3,2-b]pyridin-1-yl]-7H-pyrrolo[2,3-d]pyrimidine (12 mg, 0.049 mmol) in acetonitrile (493 tip was added DMAP (9.0 mg, 0.074 mmol) and DIPEA (17 µL, 0.099 mmol) followed by isopropylsulfonyl chloride (12 mg, 0.049 mmol). The reaction mixture was stirred for 20 hours at room temperature before being diluted with 1.0 mL DMSO and purified by mass-triggered reverse-phase HPLC using a Waters X-bridge Prep C18 column (5 micron, 19×100 mm), eluting with an ACN/water gradient (0.1% formic acid as modifier) to afford 4-{(3aR,7aR)-4-[(1-methylethyl)sulfonyl]octahydro-1H-pyrrolo[3,2-b]pyridin-1-yl}-7H-pyrrolo[2,3-d]pyrimidine. LRMS calc'd for $C_{16}H_{24}N_5O_2S$ [M+H]+, 350.2; found 350.2. $^1$H NMR (500 MHz, DMSO-$D_6$) δ 11.6 (s, 1H); 8.04 (s, 1H); 7.09 (s, 1H), 6.51 (s, 2H); 4.29 (br s, 2H); 3.97-3.64 (br m, 21-1); 3.53 (d, 2H, J=11Hz); 3.38-3.34 (m, 1H); 3.02 (t, 1H. J=10Hz); 2.01 (br s, 1H); 1.64 (s, 1H), 1.62 (br s, 1H), 1.24-1.54 (br m, 2H). 1.21 (t, 6H, J=5.5Hz). Jak1 activity: ++

The following compounds below in Table 5 were prepared in analogy to the preparation of 4-{(3aR,7aR)-4-[(1-methylethyl)sulfonyl]octahydro-1H-pyrrolo[3,2-b]pyridin-1-yl}-7H-pyrrolo[2,3-o]pyrimidine, by substituting isopropylsulfonylchloride with the appropriately functionalized sulfonyl chloride. The compounds were isolated by mass-triggered reverse-phase HPLC using a Waters X-bridge Prep C18 column (5 micron, 19×100 mm), eluting with an ACN/water gradient (using 0.1% formic acid as modifier).

TABLE 5

| Compound # | R³ | Exact Mass [M + H]+ | JAK1 Activity |
|---|---|---|---|
| 32-2 | -CH₂CH₂-phenyl<br>Single enantiomer | Calc'd 412, found 412 | +++ |
| 32-3 | Ethyl<br>Single enantiomer | Calc'd 336, found 336 | ++ |
| 32-4 | furan-2-yl<br>Single enantiomer | Calc'd 374, found 374 | ++ |
| 32-5 | Trifluoromethyl<br>Single enantiomer | Calc'd 376, found 376 | + |
| 32-6 | Phenyl<br>Single enantiomer | Calc'd 384, found 384 | ++ |
| 32-7 | Benzyl<br>Single enantiomer | Calc'd 398, found 398 | ++ |

What is claimed is:

1. A compound of formula I:

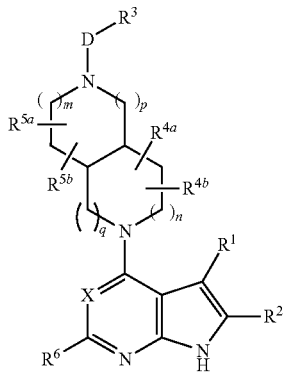

I or a pharmaceutically acceptable salt thereof; wherein:

X is N or CH;

m and n are each independently 1, 2 or 3;

p and q are each independently 0 or 1;

D is a bond, —C(O)—, —C(O)$NR^b$—, —C(O)O— or —$SO_2$—;

$R^1$ and R2 are independently H, halogen or $C_{1-3}$alkyl;

$R^3$ is selected from the group consisting of (1) hydrogen, (2) $C_{1-6}$alkyl, (3) $C_{2-10}$alkenyl, (4) $C_{2-10}$alkynyl, (5) -L-$C_{3-10}$cycloalkyl, (6) -L-aryl, (7) -L-heteroaryl, (8) -L-heterocyclyl, wherein alkyl, alkenyl and alkynyl are optionally substituted with 1 to 5 groups independently selected from $R^x$; cycloalkyl and heterocyclyl are optionally substituted with 1 to 5 groups independently selected from $R^y$; and aryl and heteroaryl are optionally substituted with 1 to 5 groups independently selected from $R^z$;

L is a bond, $C_{1-6}$alkylene, $C_{2-6}$alkenylene, $C_{2-6}$alkynylene, arylene, heteroarylene, $C_{3-10}$cycloalkylene or heterocyclyene; wherein alkylene, alkenylene and alkynylene are optionally substituted with 1 to 5 groups independently selected from $R^x$, aryl and heteroaryl wherein aryl and heteroaryl are optionally substituted with 1 to 3 groups independently selected from $R^z$; cycloalkylene or heterocyclyene are optionally substituted with 1 to 5 groups independently selected from $R^y$; and arylene and heteroarylene are optionally substituted with 1 to 5 groups independently selected from $R^z$;

$R^{4a}$, $R^{4b}$, $R^{5a}$ and $R^{5b}$ and are each independently selected from the group consisting of (1) hydrogen, (2) $OR^a$, (3) cyano, (4) halogen, (5) $C_{1-6}$alkyl, (6) $C_{2-10}$alkenyl, (7) C(O)$R^a$, (8) $CO_2R^a$, (9) $NR^bR^c$, and (10) CONR$^b$R$^c$, wherein alkyl, alkenyl and alkylcarbonyl are optionally substituted with 1 to 5 groups independently selected from $R^x$;

$R^6$ is H or NHR$^b$;

$R^a$ is selected from the group consisting of H, $C_{1-6}$alkyl, $C_{1-6}$haloalkyl, $C_{2-6}$hydroxyalkyl, $C_{2-6}$($C_{1-3}$alkoxy)alkyl, $C_{2-6}$cyanoalkyl, $C_{2-6}$aminoalkyl, $C_{2-6}$(mono$C_{1-3}$alkylamino)alkyl, $C_{2-6}$(di$C_{1-3}$alkylamino)alkyl, $C_{3-6}$cycloalkyl, aryl, heteroaryl and heterocyclyl;

$R^b$ and $R^c$ are each independently selected from H, $C_{1-6}$alkyl, $C_{1-6}$haloalkyl, $C_{3-6}$cycloalkyl, $C_{2-6}$cyanoalkyl, $C_{2-6}$hydroxyalkyl, $C_{2-6}$aminoalkyl, —COR$^a$, aryl and heteroaryl; or $R^b$, $R^c$ and the nitrogen atom to which they are attached together form a 4- to 7-membered ring optionally having an additional heteroatom selected from NR$^d$, O and S(O)r, wherein said ring being optionally substituted with 1 to 4 groups independently selected from halogen, cyano and $C_{1-6}$cyanoalkyl;

r is 0, 1 or 2, $R^d$ is selected from the group consisting of (1) H, (2) $C_{1-6}$alkyl, (3) C(O)$C_{1-6}$alkyl, $R^x$ is selected from the group consisting of (1) oxo, (2) $OR^a$, (3) cyano, (4) halogen, (5) NR$^b$R$^c$, (6) $CO_2R^a$, (7) CONR$^b$R$^c$; (8) —COR$^a$, (9) —$C_{0-6}$alkylaryl, (10) —$C_{0-6}$ alkylheteroaryl, and (11) S(O)$_r$R$^a$;

$R^y$ is selected from the group consisting of (1) a member of $R^z$, and (2) oxo;

$R^z$ is selected from the group consisting of (1) OR$^a$, (2) cyano, (3) halogen, (4) COR$^a$, (5) $CO_2R^a$, (6) nitro, (7) NR$^b$R$^c$, and (8) CONR$^b$R$^c$; (9) $C_{1-6}$alkyl, (10) $C_{1-6}$haloalkyl, (11) $C_{1-6}$hydroxyalkyl, (12) $C_{1-6}$cyanoalkyl, (13) $C_{1-6}$($C_{1-3}$alkoxy)alkyl, (14) $C_{1-6}$aminoalkyl, (15) $C_{1-6}$ mono($C_{1-3}$alkylamino)alkyl, (16) $C_{1-6}$di($C_{1-3}$alkylamino)alkyl, (17) $C_{2-6}$alkenyl, (18) $C_{2-6}$alkynyl, (19) —$SO_2NR^bR^c$, (20) —NR$^b$$SO_2$$C_{1-6}$alkyl, (21) —NR$^b$$SO_2$aryl (22) —$C_{0-6}$alkylNC(O)(O$C_{1-6}$ alkyl).

2. A compound of claim 1 wherein X is N.

3. A compound of claim 1 wherein $R^6$ is H, $R^1$ and $R^2$ are each independently H or methyl.

4. A compound of claim 1 wherein $R^6$ is H, and $R^{4a}$, $R^{4b}$, $R^{5a}$ and $R^{5b}$ are each independently H or methyl.

5. A compound of claim 1 having the formula Ie

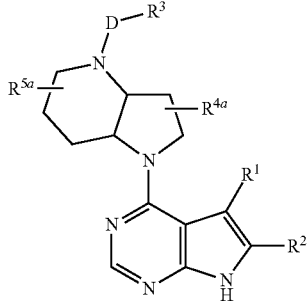

or a pharmaceutically acceptable salt thereof, wherein all the variables are as defined in claim 1.

6. A compound of claim 5 wherein D is —C(O)O—, and $R^1$, $R^2$, $R^{4a}$ and $R^{5a}$ are each independently H or methyl.

7. A compound of claim 5 wherein D is —C(O)—, and $R^1$, $R^2$, $R^{4a}$ and $R^{5a}$ are each independently H or methyl.

8. A compound of claim 5 D is —SO2—, and $R^1$, $R^2$, $R^{4a}$ and $R^{5a}$ are each independently H or methyl.

9. A compound of claim 5 D is —CONR$^b$—, and $R^1$, $R^2$, $R^{4a}$, and $R^{5a}$ are each independently H or methyl.

10. A compound of claim 5 wherein $R^3$ is (1) $C_{1-6}$alkyl, (2) -L-$C_{3-10}$cycloalkyl, (3) -L-aryl, (4) -L-heteroaryl, (5) -L-heterocyclyl, wherein alkyl is optionally substituted with 1 to 5 groups independently selected from $R^x$; cycloalkyl and heterocyclyl are optionally substituted with 1 to 5 groups independently selected from $R^y$; and aryl and heteroaryl are optionally substituted with 1 to 5 groups independently selected from $R^z$; L is a bond, $C_{1-6}$alkylene, arylene, heteroarylene, cycloalkylene or heterocyclyene; wherein alkylene is optionally substituted with 1 to 5 groups independently selected from $R^x$, aryl and heteroaryl wherein aryl and heteroaryl are optionally substituted with 1 to 3 groups independently selected from $R^z$; cycloalkylene or heterocyclyene are optionally substituted with 1 to 5 groups independently selected from $R^y$; and arylene and heteroarylene are optionally substituted with 1 to 5 groups independently selected from $R^z$.

11. A compound of claim 10 wherein $R^1$, $R^2$, $R^{4a}$, and $R^{5a}$ are each independently H or methyl.

12. A compound of claim 1 having the formula Ig

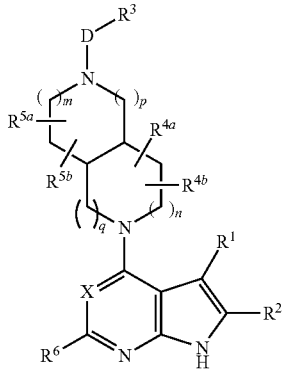

or a pharmaceutically acceptable salt thereof; wherein:
X is N or CH;
m and n are each independently 1, 2 or 3;
p and q are each independently 0 or 1;
D is a bond, —C(O)—, —C(O)NR$^b$—, —C(O)O— or —SO$_2$—;
$R^1$ and $R^2$ are independently H, halogen or $C_{1-3}$alkyl;
$R^3$ is selected from the group consisting of (1) hydrogen, (2) $C_{1-6}$alkyl, (3) $C_{2-10}$alkenyl, (4) $C_{2-10}$alkynyl, (5) -L-$C_{3-10}$cycloalkyl, (6) -L-aryl, (7) -L-heteroaryl, (8) -L-heterocyclyl, wherein alkyl, alkenyl and alkynyl are optionally substituted with 1 to 5 groups independently selected from $R^x$; cycloalkyl and heterocyclyl are optionally substituted with 1 to 5 groups independently selected from $R^y$; and aryl and heteroaryl are optionally substituted with 1 to 5 groups independently selected from $R^z$;
L is a bond, $C_{1-6}$alkylene, $C_{2-6}$alkenylene, $C_{2-6}$alkynylene, arylene, heteroarylene, $C_{3-10}$cycloalkylene or heterocyclyene; wherein alkylene, alkenylene and alkynylene are optionally substituted with 1 to 5 groups independently selected from $R^x$, aryl and heteroaryl wherein aryl and heteroaryl are optionally substituted with 1 to 3 groups independently selected from $R^z$; cycloalkylene or heterocyclyene are optionally substituted with 1 to 5 groups independently selected from $R^y$; and arylene and heteroarylene are optionally substituted with 1 to 5 groups independently selected from $R^z$;
$R^{4a}$, $R^{4b}$, $R^{5a}$ and $R^{5b}$ and are each independently selected from the group consisting of (1) hydrogen, (2) OR$^a$, (3) cyano, (4) halogen, (5) $C_{1-6}$alkyl, (6) $C_{2-10}$alkenyl, (7) C(O)R$^a$, (8) CO$_2$R$^a$, (9) NR$^b$R$^c$, and (10) CONR$^b$R$^c$, wherein alkyl, alkenyl and alkylcarbonyl are optionally substituted with 1 to 5 groups independently selected from $R^x$;
$R^6$ is H or NHR$^b$;
$R^a$ is selected from the group consisting of H, $C_{1-6}$alkyl, $C_{1-6}$haloalkyl, $C_{2-6}$hydroxyalkyl, $C_{2-6}$($C_{1-3}$alkoxy)alkyl, $C_{2-6}$cyanoalkyl, $C_{2-6}$aminoalkyl, $C_{2-6}$(mono$C_{1-3}$alkylamino)alkyl, $C_{2-6}$(di$C_{1-3}$alkylamino)alkyl, $C_{3-6}$cycloalkyl, aryl, heteroaryl and heterocyclyl;
$R^b$ and $R^c$ are each independently selected from H, $C_{1-6}$alkyl, $C_{1-6}$haloalkyl, $C^{3-6}$cycloalkyl, $C_{2-6}$cyanoalkyl, $C_{2-6}$hydroxyalkyl, $C_{2-6}$aminoalkyl, -COR$^a$, aryl and heteroaryl; or $R^b$, $R^c$ and the nitrogen atom to which they are attached together form a 4- to 7-membered ring optionally having an additional heteroatom selected from NR$^d$, O and S(O)r, wherein said ring being optionally substituted with 1 to 4 groups independently selected from halogen, cyano and $C_{1-6}$cyanoalkyl;
r is 0, 1 or 2,
$R^d$ is selected from the group consisting of (1) H, (2) $C_{1-6}$alkyl, (3) C(O)$C_{1-6}$alkyl,
$R^x$ is selected from the group consisting of (1) oxo, (2) OR$^a$, (3) cyano, (4) halogen, (5) NR$^b$R$^c$, (6) CO$_2$R$^a$, (7) CONR$^b$R$^c$; (8) -COR$^a$ and (9) S(O)$_r$R$^a$;
$R^y$ is selected from the group consisting of (1) a member of $R^z$, and (2) oxo;
$R^z$ is selected from the group consisting of (1) OR$^a$, (2) cyano, (3) halogen, (4) COR$^a$, (5) CO$_2$R$^a$, (6) nitro, (7) NR$^b$R$^c$, and (8) CONR$^b$R$^c$; (9) $C_{1-6}$alkyl, (10) $C_{1-6}$haloalkyl, (11) $C_{1-6}$hydroxyalkyl, (12) $C_{1-6}$cyanoalkyl, (13) $C_{1-6}$($C_{1-3}$alkoxy)alkyl, (14) $C_{1-6}$-aminoalkyl, (15) $C_{1-6}$ mono($C_{1-3}$alkylamino)alkyl, (16) $C_{1-6}$di($C_{1-3}$alkylamino)alkyl, (17) C$_{2-6}$alkenyl, (18) C$_{2-6}$alkynyl, (19) —SO$_2$NR$^b$R$^c$, (20) —NR$^b$SO$_2$C$_{1-6}$alkyl and (21) —NR$^b$SO$_2$aryl.

13. A compound according to claim 1, selected from the group consisting of:

benzyl 1-(7H-pyrrolo[2,3-d]pyrimidin-4-yl)octahydro-4H-pyrrolo[3,2-b]pyridine-4-carboxylate;
[3aS,7aS]-4-(octahydro-1H-pyrrolo[3,2-b]pyridin-1-yl)-7H-pyrrolo[2,3-d]pyrimidine;
[3aR,7aR]-4-(octahydro-1H-pyrrolo[3,2-b]pyridin-1-yl)-7H-pyrrolo[2,3-d]pyrimidine;
pyridin-3-ylmethyl 1-(7H-pyrrolo[2,3-d]pyrimidin-4-yl)octahydro-4H-pyrrolo[3,2-b]pyridine-4-carboxylate;
4-fluorobenzyl 1-(7H-pyrrolo[2,3-d]pyrimidin-4-yl)octahydro-4H-pyrrolo[3,2-b]pyridine-4-carboxylate;
butyl 1-(7H-pyrrolo[2,3-d]pyrimidin-4-yl)octahydro-4H-pyrrolo[3,2-b]pyridine-4-carboxylate;
3-methoxybenzyl 1-(7H-pyrrolo[2,3-d]pyrimidin-4-yl)octahydro-4H-pyrrolo[3,2-b]pyridine-4-carboxylate;
3-pyridin-3-ylpropyl 1-(7H-pyrrolo[2,3-d]pyrimidin-4-yl)octahydro-4H-pyrrolo[3,2-b]pyridine-4-carboxylate;
4-chlorobenzyl 1-(7H-pyrrolo[2,3-d]pyrimidin-4-yl)octahydro-4H-pyrrolo[3,2-b]pyridine-4-carboxylate;
3-phenylpropyl 1-(7H-pyrrolo[2,3-d]pyrimidin-4-yl)octahydro-4H-pyrrolo[3,2-b]pyridine-4-carboxylate;
2-phenylethyl 1-(7H-pyrrolo[2,3-d]pyrimidin-4-yl)octahydro-4H-pyrrolo[3,2-b]pyridine-4-carboxylate;
3-fluorobenzyl 1-(7H-pyrrolo[2,3-d]pyrimidin-4-yl)octahydro-4H-pyrrolo[3,2-b]pyridine-4-carboxylate;
tetrahydro-2H-pyran-4-yl 1-(7H-pyrrolo[2,3-d]pyrimidin-4-yl)octahydro-4H-pyrrolo[3,2-b]-pyridine-4-carboxylate;
2,3-dihydro-1H-inden-2-yl 1-(7H-pyrrolo[2,3-d]pyrimidin-4-yl)octahydro-4H-pyrrolo[3,2-b]pyridine-4-carboxylate;
pyridin-2-ylmethyl 1-(7H-pyrrolo[2,3-d]pyrimidin-4-yl)octahydro-4H-pyrrolo[3,2-b]pyridine-4-carboxylate;
pyridin-4-ylmethyl 1-(7H-pyrrolo[2,3-d]pyrimidin-4-yl)octahydro-4H-pyrrolo[3,2-b]pyridine-4-carboxylate;
4-methoxybenzyl 1-(7H-pyrrolo[2,3-d]pyrimidin-4-yl)octahydro-4H-pyrrolo[3,2-b]pyridine-4-carboxylate;
naphthalen-2-ylmethyl 1-(7H-pyrrolo[2,3-d]pyrimidin-4-yl)octahydro-4H-pyrrolo[3,2-b]-pyridine-4-carboxylate;
3-methylbenzyl 1-(7H-pyrrolo[2,3-d]pyrimidin-4-yl)octahydro-4H-pyrrolo[3,2-b]pyridine-4-carboxylate;
4-methylbenzyl 1-(7H-pyrrolo[2,3-d]pyrimidin-4-yl)octahydro-4H-pyrrolo[3,2-b]pyridine-4-carboxylate;
pyrazin-2-ylmethyl 1-(7H-pyrrolo[2,3-d]pyrimidin-4-yl)octahydro-4H-pyrrolo[3,2-b]pyridine-4-carboxylate;
pyridin-3-ylmethyl (3aR,7aR)-1-(7H-pyrrolo[2,3-d]pyrimidin-4-yl)octahydro-4H-pyrrolo[3,2-b]-pyridine-4-carboxylate;
3-(methoxycarbonyl)benzyl (3aR,7aR)-1-(7H-pyrrolo[2,3-d]pyrimidin-4-yl)octahydro-4H-pyrrolo[3,2-b]pyridine-4-carboxylate;
2-[4-(methoxycarbonyl)phenyl]ethyl (3aR,7aR)-1-(7H-pyrrolo[2,3-d]pyrimidin-4-yl)octahydro-4H-pyrrolo[3,2-b]pyridine-4-carboxylate;
3-[4-(methoxycarbonyl)phenyl]propyl (3aR,7aR)-1-(7H-pyrrolo[2,3-d]pyrimidin-4-yl)octahydro-4H-pyrrolo[3,2-b]pyridine-4-carboxylate;
(1R)-1-phenylethyl 1-(7H-pyrrolo[2,3-d]pyrimidin-4-yl)octahydro-4H-pyrrolo[3,2-b]pyridine-4-carboxylate;
(1S)-1-phenylethyl 1-(7H-pyrrolo[2,3-d]pyrimidin-4-yl)octahydro-4H-pyrrolo[3,2-b]pyridine-4-carboxylate;
4-(methoxycarbonyl)benzyl 1-(7H-pyrrolo[2,3-d]pyrimidin-4-yl)octahydro-4H-pyrrolo[3,2-b]-pyridine-4-carboxylate;
3-(methoxycarbonyl)phenyl 1-(7H-pyrrolo[2,3-d]pyrimidin-4-yl)octahydro-4H-pyrrolo[3,2-b]-pyridine-4-carboxylate;
2-(1,1-dioxidothiomorpholin-4-yl)ethyl (3aR,7aR)-1-(7H-pyrrolo[2,3-d]pyrimidin-4-yl)octahydro-4H-pyrrolo[3,2-b]pyridine-4-carboxylate;
2-(2,3-dihydro-1-benzofuran-5-yl)ethyl (3aR,7aR)-1-(7H-pyrrolo[2,3-d]pyrimidin-4-yl)octahydro-4H-pyrrolo[3,2-b]pyridine-4-carboxylate;
2-[2-(methoxycarbonyl)cyclopropyl]ethyl (3aR,7aR)-1-(7H-pyrrolo[2,3-d]pyrimidin-4-yl)octahydro-4H-pyrrolo[3,2-b]pyridine-4-carboxylate;
2-fluoroethyl (3aR,7aR)-1-(7H-pyrrolo[2,3-d]pyrimidin-4-yl)octahydro-4H-pyrrolo[3,2-b]pyridine-4-carboxylate;
cyclopropylmethyl (3aR,7aR)-1-(7H-pyrrolo[2,3-d]pyrimidin-4-yl)octahydro-4H-pyrrolo[3,2-b]-pyridine-4-carboxylate;
cyclohexyl (3aR,7aR)-1-(7H-pyrrolo[2,3-d]pyrimidin-4-yl)octahydro-4H-pyrrolo[3,2-b]pyridine-4-carboxylate;
2-fluorobenzyl (3aR,7aR)-1-(7H-pyrrolo[2,3-d]pyrimidin-4-yl)octahydro-4H-pyrrolo[3,2-b]-pyridine-4-carboxylate;
2-naphthalen-1-ylethyl (3aR,7aR)-1-(7H-pyrrolo[2,3-d]pyrimidin-4-yl)octahydro-4H-pyrrolo[3,2-b]pyridine-4-carboxylate;
2-methoxyethyl (3aR,7aR)-1-(7H-pyrrolo[2,3-d]pyrimidin-4-yl)octahydro-4H-pyrrolo[3,2-b]-pyridine-4-carboxylate;
2-(2-oxopyrrolidin-1-yl)ethyl (3aR,7aR)-1-(7H-pyrrolo[2,3-d]pyrimidin-4-yl)octahydro-4H-pyrrolo[3,2-b]pyridine-4-carboxylate;
2-pyridin-2-ylethyl (3aR,7aR)-1-(7H-pyrrolo[2,3-d]pyrimidin-4-yl)octahydro-4H-pyrrolo[3,2-b]-pyridine-4-carboxylate;
2-(dimethylamino)ethyl (3aR,7aR)-1-(7H-pyrrolo[2,3-d]pyrimidin-4-yl)octahydro-4H-pyrrolo[3,2-b]pyridine-4-carboxylate;
2-morpholin-4-ylethyl (3aR,7aR)-1-(7H-pyrrolo[2,3-d]pyrimidin-4-yl)octahydro-4H-pyrrolo[3,2-b]pyridine-4-carboxylate;
2-pyrrolidin-1-ylethyl (3aR,7aR)-1-(7H-pyrrolo[2,3-d]pyrimidin-4-yl)octahydro-4H-pyrrolo[3,2-b]pyridine-4-carboxylate;
2-(4-methylpiperazin-1-yl)ethyl (3aR,7aR)-1-(7H-pyrrolo[2,3-d]pyrimidin-4-yl)octahydro-4H-pyrrolo[3,2-b]pyridine-4-carboxylate;
(1-methylpiperidin-4-yl)methyl (3aR,7aR)-1-(7H-pyrrolo[2,3-d]pyrimidin-4-yl)octahydro-4H-pyrrolo[3,2-b]pyridine-4-carboxylate;
2-(2,2,2-trifluoroethoxy)ethyl (3aR,7aR)-1-(7H-pyrrolo[2,3-d]pyrimidin-4-yl)octahydro-4H-pyrrolo[3,2-b]pyridine-4-carboxylate;
2-(3,5-difluorophenyl)ethyl (3aR,7aR)-1-(7H-pyrrolo[2,3-d]pyrimidin-4-yl)octahydro-4H-pyrrolo[3,2-b]pyridine-4-carboxylate;
2-(1H-indol-1-yl)ethyl (3aR,7aR)-1-(7H-pyrrolo[2,3-d]pyrimidin-4-yl)octahydro-4H-pyrrolo[3,2-b]pyridine-4-carboxylate;
cyclohexylmethyl (3aR,7aR)-1-(7H-pyrrolo[2,3-d]pyrimidin-4-yl)octahydro-4H-pyrrolo[3,2-b]pyridine-4-carboxylate;

3-phenylpropyl (3aR,7aR)-1-(7H-pyrrolo[2,3-d]pyrimidin-4-yl)octahydro-4H-pyrrolo[3,2-b]-pyridine-4-carboxylate;

3-pyridin-3-ylpropyl (3aR,7aR)-1-(7H-pyrrolo[2,3-d]pyrimidin-4-yl)octahydro-4H-pyrrolo[3,2-b]pyridine-4-carboxylate;

4-(methoxycarbonyl)benzyl (3aR,7aR)-1-(7H-pyrrolo[2,3-d]pyrimidin-4-yl)octahydro-4H-pyrrolo[3,2-b]pyridine-4-carboxylate;

4-(methoxycarbonyl)benzyl (3aS,7aS)-1-(7H-pyrrolo[2,3-d]pyrimidin-4-yl)octahydro-4H-pyrrolo[3,2-b]pyridine-4-carboxylate;

4-[({[(3aR,7aR)-1-(7H-pyrrolo[2,3-d]pyrimidin-4-yl)octahydro-4H-pyrrolo[3,2-b]pyridin-4-yl]-carbonyl}oxy)methyl]benzoic acid;

4-(dimethylcarbamoyl)benzyl (3aR,7aR)-1-(7H-pyrrolo[2,3-d]pyrimidin-4-yl)octahydro-4H-pyrrolo[3,2-b]pyrindine-4-carboxylate;

4-carbamoylbenzyl (3aR,7aR)-1-(7H-pyrrolo[2,3-d]pyrimidin-4-yl)octahydro-4H-pyrrolo[3,2-b]pyridine-4-carboxylate;

4-(methylcarbamoyl)benzyl (3aR,7aR)-1-(7H-pyrrolo[2,3-d]pyrimidin-4-yl)octahydro-4H-pyrrolo[3,2-b]pyridine-4-carboxylate;

4-{[2-(dimethylamino)ethyl]carbamoyl}benzyl (3aR,7aR)-1-(7H-pyrrolo[2,3-d]pyrimidin-4-yl)octahydro-4H-pyrrolo[3,2-b]pyridine-4-carboxylate;

4-{[2-(dimethylamino)ethyl](methyl)carbamoyl}benzyl (3aR,7aR)-1-(7H-pyrrolo[2,3-d]pyrimidin-4-yl)octahydro-4H-pyrrolo[3,2-b]pyridine-4-carboxylate;

4-{[(tert-butoxycarbonyl)amino]methyl}benzyl (3aR,7aR)-1-(7H-pyrrolo[2,3-d]pyrimidin-4-yl)octahydro-4-pyrrolo[3,2-b]pyridine-4-carboxylate;

(1S)-1-phenylethyl (3aR, 7aR)-1-(7H-pyrrolo[2,3-d]pyrimidin-4-yl)octahydro-4-pyrrolo[3,2-b]pyridine-4-carboxylate;

(1R and 1S)-3-(morpholin-4-yl)-1-phenylpropyl (3aR,7aR)-1-(7H-pyrrolo[2,3-d]pyrimidin-4-yl)octahydro-4-pyrrolo[3,2-b]pyridine-4-carboxylate;

4-(aminomethyl)benzyl (3aR,7aR)-1-(7H-pyrrolo[2,3-d]pyrimidin-4-yl)octahydro-4H-pyrrolo[3,2-b]pyridine-4-carboxylate;

4-(hydroxymethyl)benzyl (3aR,7aR)-1-(7H-pyrrolo[2,3-d]pyrimidin-4-yl)octahydro-4H-pyrrolo[3,2-b]pyridine-4-carboxylate;

tert-butyl (3aR,7aR)-1-(7H-pyrrolo[2,3-d]pyrimidin-4-yl)octahydro-4H-pyrrolo[3,2-b]pyridine-4-carboxylate;

3-oxo-3-[(3aR,7aR)-1-(7H-pyrrolo[2,3-d]pyrimidin-4-yl)octahydro-4H-pyrrolo[3,2-b]pyridin-4-yl]propanenitrile;

methyl 4-{3-[(3aR,7aR)-1-(7H-pyrrolo[2,3-d]pyrimidin-4-yl)octahydro-4H-pyrrolo[3,2-b]pyridin-4-yl]propyl}benzoate;

4-{3-[(3aR,7aR)-1-(7H-pyrrolo[2,3-d]pyrimidin-4-yl)octahydro-4H-pyrrolo[3,2-b]pyridin-4-yl]-propyl}benzoic acid;

benzyl 1-(6-methyl-7H-pyrrolo[2,3-d]pyrimidin-4-yl)octahydro-4H-pyrrolo[3,2-b]pyridine-4-carboxylate;

benzyl 4-(7H-pyrrolo[2,3-d]pyrimidin-4-yl)octahydro-1H-pyrrolo[3,2-b]pyridine-1-carboxylate;

2-hydroxy-1-[1-(7H-pyrrolo[2,3-d]pyrimidin-4-yl)octahydro-4H-pyrrolo[3,2-b]pyridin-4-yl]ethanone;

(2S)-3,3,3-trifluoro-2-methoxy-2-phenyl-1-[(3aR,7aR)-1-(7H-pyrrolo[2,3-d]pyrimidin-4-yl)-octahydro-4H-pyrrolo[3,2-b]pyridine-4-yl]propan-1-one;

(2R)-3,3,3-trifluoro-2-methoxy-2-phenyl-1-[(3aR,7aR)-1-(7H-pyrrolo[2,3-d]pyrimidin-4-yl)-octahydro-4H-pyrrolo[3,2-b]pyridine-4-yl]propan-1-one;

benzyl 7-methyl-1-(7H-pyrrolo[2,3 -d]pyrimidin-4-yl)octahydro-4H-pyrrolo[3,2-b]pyridine-4-carboxylate;

4-(4-benzyl-7-methyloctahydro-1H-pyrrolo[3,2-b]pyridin-1-yl)-7H-pyrrolo[2,3 -d]pyrimidine;

3-[7-methyl-1-(7H-pyrrolo[2,3-d]pyrimidin-4-yl)octahydro-4H-pyrrolo[3,2-b]pyridin-4-yl]-3-oxopropanenitrile;

methyl 4-[({[(3aR,7aR)-1-(7H-pyrrolo[2,3-d]pyrimidin-4-yl)octahydro-4H-pyrrolo[3,2-b]-pyridine-4-yl]carbonyl}amino)methyl]benzoate;

methyl 4-[(methyl{[(3aR,7aR)-1-(7H-pyrrolo[2,3-d]pyrimidin-4-yl)octahydro-4H-pyrrolo[3,2-b]pyridin-4-yl]carbonyl}amino)methyl]benzoate;

4-[({[(3aR,7aR)-1-(7H-pyrrolo[2,3-d]pyrimidin-4-yl)octahydro-4H-pyrrolo[3,2-b]pyridin-4-yl]carbonyl}amino)methyl]benzoic acid;

methyl 4-{3-oxo-3-[(3aR,7aR)-1-(7H-pyrrolo[2,3-d]pyrimidin-4-yl)octahydro-4H-pyrrolo[3,2-b]pyridin-4-yl]propyl}benzoate;

4-{3-oxo-3-[(3aR,7aR)-1-(7H-pyrrolo[2,3-d]pyrimidin-4-yl)octahydro-4H-pyrrolo[3,2-b]pyridin-4-yl]propyl}benzoic acid;

4-[2-({[(3aR,7aR)-1-(7H-pyrrolo[2,3-d]pyrimidin-4-yl)octahydro-4H-pyrrolo[3,2-b]pyridin-4-yl]carbonyl}oxy)ethyl]benzoic acid;

4-{4-[(4-morpholin-4-ylphenyl)carbonyl]octahydro-1H-pyrrolo[3,2-b]pyridin-1-yl}-7H-pyrrolo[2,3 -d]pyrimidine;

4-(4-pentanoyloctahydro-1H-pyrrolo[3,2-b]pyridin-1-yl)-7H-pyrrolo[2,3-d]pyrimidine;

4-[4-(phenylcarbonyl)octahydro-1H-pyrrolo[3,2-b]pyridin-1-yl]-7H-pyrrolo[2,3-d]pyrimidine;

4-{4-[(4-methoxyphenyl)acetyl]octahydro-1H-pyrrolo[3,2-b]pyridin-1-yl}-7H-pyrrolo[2,3-d]-pyrimidine;

4-(4-{[4-(trifluoromethyl)phenyl]acetyl}octahydro-1H-pyrrolo[3,2-b]pyridin-1-yl)-7H-pyrrolo[2,3-d]pyrimidine;

4-(4-{[4-(4-methylpiperazin-1-yl)phenyl]carbonyl}octahydro-1H-pyrrolo[3,2-b]pyridin-1-yl)-7H-pyrrolo[2,3-d]pyrimidine;

4-[(3aR,7aR)-4-propanoyloctahydro-1H-pyrrolo[3,2-b]pyridin-1-yl]-7H-pyrrolo[2,3-d]-pyrimidine;

4-[(3aR,7aR)-4-(methoxyacetyl)octahydro-1H-pyrrolo[3,2-b]pyridin-1-yl]-7H-pyrrolo[2,3-d]-pyrimidine;

4-[(3aR,7aR)-4-(furan-2-ylcarbonyl)octahydro-1H-pyrrolo[3,2-b]pyridin-1-yl]-7H-pyrrolo[2,3-d]-pyrimidine;

4-[(3aR,7aR)-4-(pyridin-3-ylcarbonyl)octahydro-1H-pyrrolo[3,2-b]pyridin-1-yl]-7H-pyrrolo[2,3-d]pyrimidine;

4-[(3aR,7aR)-4-(pyridin-2-ylcarbonyl)octahydro-1H-pyrrolo[3,2-b]pyridin-1-yl]-7H-pyrrolo[2,3-d]pyrimidine;

p1  4-[(3aR,7aR)-4-(pyridin-4-ylcarbonyl)octahydro-1H-pyrrolo[3,2-b]pyridin-1-yl]-7H-pyrrolo[2,3-d]pyrimidine;

4-[(3aR,7aR)-4-(pyrazin-2-ylcarbonyl)octahydro-1H-pyrrolo[3,2-b]pyridin-1-yl]-7H-pyrrolo[2,3-d]pyrimidine;

4-{(3aR,7aR)-4-[(5-methylisoxazol-3-yl)carbonyl]octahydro-1H-pyrrolo[3,2-b]pyridin-1-yl}-7H-pyrrolo[2,3-d]pyrimidine;

4-[(3aR,7aR)-4-(cyclohexylcarbonyl)octahydro-1H-pyrrolo[3,2-b]pyridin-1-yl]-7H-pyrrolo[2,3-d]pyrimidine;

1-{2-oxo-2-[(3aR,7aR)-1-(7H-pyrrolo[2,3-d]pyrimidin-4-yl)octahydro-4H-pyrrolo[3,2-b]pyridin-4-yl]ethyl}pyrrolidin-2-one;

4-{(3aR,7aR)-4-[(2-chlorophenyl)carbonyl]octahydro-1H-pyrrolo[3,2-b]pyridin-1-yl}-7H-pyrrolo[2,3-d]pyrimidine;

4-{(3aR,7aR)-4-[(3-chlorophenyl)carbonyl]octahydro-1H-pyrrolo[3,2-b]pyridin-1-yl}-7H-pyrrolo[2,3-d]pyrimidine;

4-[(3aR,7aR)-4-(1H-indol-2-ylcarbonyl)octahydro-1H-pyrrolo[3,2-b]pyridin-1-yl]-7H-pyrrolo[2,3-d]pyrimidine;

4-[(3aR,7aR)-4-(naphthalen-1-ylcarbonyl)octahydro-1H-pyrrolo[3,2-b]pyridin-1-yl]-7H-pyrrolo[2,3-d]pyrimidine;

4-{(3aR,7aR)-4-[(1-methyl-1H-indol-2-yl)carbonyl]octahydro-1H-pyrrolo[3,2-b]pyridin-1-yl}-7H-pyrrolo[2,3-d]pyrimidine;

4-{(3aR,7aR)-4-[(3-morpholin-4-ylphenyl)carbonyl]octahydro-1H-pyrrolo[3,2-b]pyridin-1-yl}-7H-pyrrolo[2,3-d]pyrimidine;

4-[(3aR,7aR)-4-(biphenyl-2-ylcarbonyl)octahydro-1H-pyrrolo[3,2-b]pyridin-1-yl]-7H-pyrrolo[2,3-d]pyrimidine;

4-[(3aR,7aR)-4-(diphenylacetyl)octahydro-1H-pyrrolo[3,2-b]pyridin-1-yl]-7H-pyrrolo[2,3-d]-pyrimidine;

4-[(3aR,7aR)-4-(imidazo[1,2-a]pyridin-2-ylcarbonyl)octahydro-1H-pyrrolo[3,2-b]pyridin-1-yl]-7H-pyrrolo[2,3-d]pyrimidine;

4-[(3aR,7aR)-4-(naphthalen-2-ylcarbonyl)octahydro-1H-pyrrolo[3,2-b]pyridin-1-yl]-7H-pyrrolo[2,3-d]pyrimidine;

4-[(3aR,7aR)-4-(imidazo[1,2-a]pyrimidin-2-ylcarbonyl)octahydro-1H-pyrrolo[3,2-b]pyridin-1-yl1]-7H-pyrrolo[2,3-d]pyrimidine;

4-[(3aR,7aR)-4-(thiophen-2-ylcarbonyl)octahydro-1H-pyrrolo[3,2-b]pyridin-1-yl]-7H-pyrrolo[2,3-d]pyrimidine;

4-{[(3aR,7aR)-1-(7H-pyrrolo[2,3-d]pyrimidin-4-yl)octahydro-4H-pyrrolo[3,2-b]pyridin-4-yl]carbonyl}benzonitrile;

4-[(3aR,7aR)-4-{[(1R,2S)-2-propylcyclopropyl]carbonyl}octahydro-1H-pyrrolo[3,2-b]pyridin-1-yl]-7H-pyrrolo[2,3-d]pyrimidine;

3-{[(3aR,7aR)-1-(7H-pyrrolo[2,3-d]pyrimidin-4-yl)octahydro-4H-pyrrolo[3,2-b]pyridin-4-yl]carbonyl}benzonitrile;

4-[(3aR,7aR)-4-(thiophen-3-ylcarbonyl)octahydro-1H-pyrrolo[3,2-b]pyridin-1-yl]-7H-pyrrolo[2,3-d]pyrimidine;

2-{[(3aR,7aR)-1-(7H-pyrrolo[2,3-d]pyrimidin-4-yl)octahydro-4H-pyrrolo[3,2-b]pyridin-4-yl]carbonyl}benzonitrile;

4-[(3aR,7aR)-4-(phenylcarbonyl)octahydro-1H-pyrrolo[3,2-b]pyridin-1-yl]-7H-pyrrolo[2,3-d]-pyrimidine;

N,N-dimethyl-4-{[(3aR,7aR)-1-(7H-pyrrolo[2,3-d]pyrimidin-4-yl)octahydro-4H-pyrrolo[3,2-b]-pyridin-4-yl]carbonyl}piperidine-1-carboxamide;

2-{2-oxo-2-[(3aR,7aR)-1-(7H-pyrrolo[2,3-d]pyrimidin-4-yl)octahydro-4H-pyrrolo[3,2-b]pyridin-4-yl]ethyl}-1,2,3,4-tetrahydroisoquinoline;

5-{[(3aR,7aR)-1-(7H-pyrrolo[2,3-d]pyrimidin-4-yl)octahydro-4H-pyrrolo[3,2-b]pyridin-4-yl]carbonyl}isoquinoline;

4-[(3aR,7aR)-4-(2,3-dihydro-1,4-benzodioxin-2-ylcarbonyl)octahydro-1H-pyrrolo[3,2-b]pyridin-1-yl]-7H-pyrrolo[2,3-d]pyrimidine;

8-{[(3aR,7aR)-1-(7H-pyrrolo[2,3-d]pyrimidin-4-yl)octahydro-4H-pyrrolo[3,2-b]pyridin-4-yl]carbonyl}isoquinoline;

4-{[(3aR,7aR)-1-(7H-pyrrolo[2,3-d]pyrimidin-4-yl)octahydro-4H-pyrrolo[3,2-b]pyridin-4-yl]carbonyl}isoquinoline;

4-{(3aR,7aR)-4-[(5-cyclopropyl-1,3-oxazol-4-yl)carbonyl]octahydro-1H-pyrrolo[3,2-b]pyridin-1-yl}-7H-pyrrolo[2,3-d]pyrimidine;

4-[(3aR,7aR)-4-(2-methyl-3-phenylpropanoyl)octahydro-1H-pyrrolo[3,2-b]pyridin-1-yl]-7H-pyrrolo[2,3-d]pyrimidine;

4-[(3aR,7aR)-4-(2-morpholin-4-ylpropanoyl)octahydro-1H-pyrrolo[3,2-b]pyridin-1-yl]-7H-pyrrolo[2,3-d]pyrimidine;

3-{[(3aR,7aR)-1-(7H-pyrrolo[2,3-d]pyrimidin-4-yl)octahydro-4H-pyrrolo[3,2-b]pyridin-4-yl]carbonyl}quinoline;

4-[(3aR,7aR)-4-(1H-pyrrolo[3,2-b]pyridin-3-ylcarbonyl)octahydro-1H-pyrrolo[3,2-b]pyridin-1-yl]-7H-pyrrolo[2,3-d]pyrimidine;

2-oxo-1-phenyl-2-[(3aR,7aR)-1-(7H-pyrrolo[2,3-d]pyrimidin-4-yl)octahydro-4H-pyrrolo[3,2-b]-pyridin-4-yl]ethanol;

1-{[(3aR,7aR)-1-(7H-pyrrolo[2,3-d]pyrimidin-4-yl)octahydro-4H-pyrrolo[3,2-b]pyridin-4-yl]carbonyl}isoquinoline;

4-[(3aR,7aR)-4-(6H-thieno[2,3-b]pyrrol-5-ylcarbonyl)octahydro-1H-pyrrolo[3,2-b]pyridin-1-yl]-7H-pyrrolo[2,3-d]pyrimidine;

4-[(3aR,7aR)-4-(imidazo[1,2-a]pyrimidin-2-ylcarbonyl)octahydro-1H-pyrrolo[3,2-b]pyridin-1-yl]-7H-pyrrolo[2,3-d]pyrimidine;

4-{(3aR,7aR)-4-[(1-methyl-1H-pyrrolo[2,3-b]pyridin-5-yl)carbonyl]octahydro-1H-pyrrolo[3,2-b]pyridin-1-yl}-7H-pyrrolo[2,3-d]pyrimidine;

8-{[(3aR,7aR)-1-(7H-pyrrolo[2,3-d]pyrimidin-4-yl)octahydro-4H-pyrrolo[3,2-b]pyridin-4-yl]carbonyl}quinoline;

4-[(3aR,7aR)-4-(indolizin-2-ylcarbonyl)octahydro-1H-pyrrolo[3,2-b]pyridin-1-yl]-7H-pyrrolo[2,3-d]pyrimidine;

4-[(3aR,7aR)-4-(1H-benzimidazol-1-ylacetyl)octahydro-1H-pyrrolo[3,2-b]pyridin-1-yl]-7H-pyrrolo[2,3-d]pyrimidine;

4-[(3aR,7aR)-4-(2H-indazol-2-ylacetyl)octahydro-1H-pyrrolo[3,2-b]pyridin-1-yl]-7H-pyrrolo[2,3-d]pyrimidine;

4-{(3aR,7aR)-4-[3-(1-methylpiperidin-3-yl)propanoyl]octahydro-1H-pyrrolo[3,2-b]pyridin-1-yl}-7H-pyrrolo[2,3-d]pyrimidine;

(2S and 2R)-2-methyl-3-phenyl-1-[(3aR,7aR)-1-(7H-pyrrolo[2,3-d]pyrimidin-4-yl)octahydro-4H-pyrrolo[3,2-b]pyridine-4-yl]propan-1-one;

4-[(3aR,7aR)-4-{[3-(3-fluorophenyl)isoxazol-5-yl]carbonyl}octahydro-1H-pyrrolo[3,2-b]pyridin-1-yl]-7H-pyrrolo[2,3-d]pyrimidine;

4-{(3aR,7aR)-4-[(1-methyl-1H-pyrrolo[2,3-b]pyridin-5-yl)carbonyl]octahydro-1H-pyrrolo[3,2-b]pyridin-1-yl}-7H-pyrrolo[2,3-d]pyrimidine;

4-{(3aR,7aR)-4-[(1-methyl-1H-indazol-5-yl)acetyl]octahydro-1H-pyrrolo[3,2-b]pyridin-1-yl}-7H-pyrrolo[2,3-d]pyrimidine;

4-{(3aR,7aR)-4-[(7-chloroimidazo[1,2-a]pyridin-2-yl)carbonyl]octahydro-1H-pyrrolo[3,2-b]pyridin-1-yl}-7H-pyrrolo[2,3-d]pyrimidine;

4-{[(3aR,7aR)-1-(7H-pyrrolo[2,3-d]pyrimidin-4-yl)octahydro-4H-pyrrolo[3,2-b]pyridin-4-yl]carbonyl}quinoline;

6-{[(3aR,7aR)-1-(7H-pyrrolo[2,3-d]pyrimidin-4-yl)octahydro-4H-pyrrolo[3,2-b]pyridin-4-yl]carbonyl}-2,3-dihydro-1H-isoindol-1-one;

benzyl1-(1H-pyrrolo[2,3-b]pyridine-4-yl)octahydro-4H-pyrrolo[3,2-b]pyridine-4-carboxylate;

4-[4-(5-phenyl-1,3,4-oxadiazol-2-yl)octahydro-1H-pyrrolo[3,2-b]pyridin-1-yl]-7H-pyrrolo[2,3-d]pyrimidine;

4-{(3aR,7aR)-4-[(1-methylethyl)sulfonyl]octahydro-1H-pyrrolo[3,2-b]pyridin-1-yl}-7H-pyrrolo[2,3-d]pyrimidine;

4-{(3aR,7aR)-4-[(2-phenylethyl)sulfonyl]octahydro-1H-pyrrolo[3,2-b]pyridin-1-yl}-7H-pyrrolo[2,3-d]pyrimidine;

4-[(3aR,7aR)-4-(ethylsulfonyl)octahydro-1H-pyrrolo[3,2-b]pyridin-1-yl]-7H-pyrrolo[2,3-d]pyrimidine;

4-[(3aR,7aR)-4-(furan-2-ylsulfonyl)octahydro-1H-pyrrolo[3,2-b]pyridin-1-yl]-7H-pyrrolo[2,3-d]pyrimidine;

4-{(3aR,7aR)-4-[(trifluoromethyl)sulfonyl]octahydro-1H-pyrrolo[3,2-b]pyridin-1-yl}-7H-pyrrolo[2,3-d]pyrimidine;

4-[(3aR,7aR)-4-(phenylsulfonyl)octahydro-1H-pyrrolo[3,2-b]pyridin-1-yl]-7H-pyrrolo[2,3-d]pyrimidine; and 4-[(3aR,7aR)-4-(benzylsulfonyl)octahydro-1H-pyrrolo[3,2-b]pyridin-1-yl]-7H-pyrrolo[2,3-d]pyrimidine, or a pharmaceutically acceptable salt thereof.

14. A pharmaceutical composition comprising a compound of claim 1 or a pharamceutically acceptable salt thereof and a pharmaceutically acceptable carrier.

\* \* \* \* \*